(12) United States Patent
Weber et al.

(10) Patent No.: US 8,048,150 B2
(45) Date of Patent: Nov. 1, 2011

(54) ENDOPROSTHESIS HAVING A FIBER MESHWORK DISPOSED THEREON

(75) Inventors: Jan Weber, Maple Grove, MN (US); James Q. Feng, Maple Grove, MN (US); Liliana Atanasoska, Edina, MN (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 1555 days.

(21) Appl. No.: 11/403,344

(22) Filed: Apr. 12, 2006

(65) Prior Publication Data

US 2007/0244569 A1 Oct. 18, 2007

(51) Int. Cl.
A61F 2/06 (2006.01)

(52) U.S. Cl. .................. 623/1.42; 623/1.15; 623/1.43

(58) Field of Classification Search .............. 623/1.15, 623/1.38–1.54; A61F 2/06
See application file for complete search history.

(56) References Cited

U.S. PATENT DOCUMENTS

| | | |
|---|---|---|
| 2,950,187 A | 8/1960 | Ototani |
| 3,560,362 A | 2/1971 | Kasamatsu et al. |
| 3,569,660 A | 3/1971 | Houldcroft |
| 3,687,135 A | 8/1972 | Stroganov et al. |
| 3,758,396 A | 9/1973 | Vieth et al. |
| 3,868,578 A | 2/1975 | Oldham |
| 3,910,819 A | 10/1975 | Rembaum et al. |
| 3,948,254 A | 4/1976 | Zaffaroni |
| 3,952,334 A | 4/1976 | Bokros et al. |
| 3,993,072 A | 11/1976 | Zaffaroni |
| 4,002,877 A | 1/1977 | Banas |
| 4,101,984 A | 7/1978 | MacGregor |
| 4,143,661 A | 3/1979 | LaForge et al. |
| 4,202,055 A | 5/1980 | Reiner et al. |
| 4,237,559 A | 12/1980 | Borom |
| 4,308,868 A | 1/1982 | Jhabvala |
| 4,334,327 A | 6/1982 | Lyman et al. |
| 4,401,546 A | 8/1983 | Nakamura et al. |
| 4,532,929 A | 8/1985 | Mattei et al. |
| 4,539,061 A | 9/1985 | Sagiv |
| 4,542,539 A | 9/1985 | Rowe et al. |

(Continued)

FOREIGN PATENT DOCUMENTS

AU 739 507 11/1998

(Continued)

OTHER PUBLICATIONS

U.S. Appl. No. 10/849,742, filed Nov. 10, 2004, Chen et al.

(Continued)

*Primary Examiner* — Thomas J Sweet
*Assistant Examiner* — Jason-Dennis Stewart
(74) *Attorney, Agent, or Firm* — Fish & Richardson P.C.

(57) ABSTRACT

The present invention comprises a medical device having an underlying structure on which is disposed a fiber meshwork composed of one or more fibers of substantially uniform diameter. The fiber meshwork may optionally have a multi-layer structure disposed upon it. Either or both of the fiber meshwork or the multi-layer structure may have one or more therapeutic agents absorbed within it. The fiber meshwork is permeable to body fluids and thereby permits body fluids to contact the underlying structure to facilitate its controlled disintegration. The fiber meshwork degrades more slowly than the underlying structure thereby permitting release of the therapeutic agent over a timescale longer than that of the lifetime of the underlying structure, while also ensuring that the support function of the underlying structure is not abrogated by the disintegration of the underlying structure.

39 Claims, 8 Drawing Sheets

U.S. PATENT DOCUMENTS

| | | | |
|---|---|---|---|
| 4,585,652 A | 4/1986 | Miller et al. | |
| 4,634,502 A | 1/1987 | Callahan et al. | |
| 4,655,771 A | 4/1987 | Wallsten | |
| 4,657,544 A | 4/1987 | Pinchuk | |
| 4,665,896 A | 5/1987 | LaForge et al. | |
| 4,705,502 A | 11/1987 | Patel | |
| 4,713,070 A | 12/1987 | Mano | |
| 4,725,273 A | 2/1988 | Kira | |
| 4,733,665 A | 3/1988 | Palmaz | |
| 4,767,418 A | 8/1988 | Deininger et al. | |
| 4,784,659 A | 11/1988 | Fleckenstein et al. | |
| 4,800,882 A | 1/1989 | Gianturco | |
| 4,804,382 A | 2/1989 | Turina et al. | |
| 4,886,062 A | 12/1989 | Wiktor | |
| 4,954,126 A | 9/1990 | Wallsten | |
| 4,976,692 A | 12/1990 | Atad | |
| 4,994,071 A | 2/1991 | MacGregor | |
| 5,024,671 A | 6/1991 | Tu et al. | |
| 5,059,211 A | 10/1991 | Stack et al. | |
| 5,061,275 A | 10/1991 | Wallsten et al. | |
| 5,061,914 A | 10/1991 | Busch et al. | |
| 5,073,365 A | 12/1991 | Katz et al. | |
| 5,079,203 A | 1/1992 | Pinnavaia | |
| 5,091,024 A | 2/1992 | DeBold et al. | |
| 5,091,205 A | 2/1992 | Fan | |
| 5,102,403 A | 4/1992 | Alt | |
| 5,120,322 A | 6/1992 | Davis et al. | |
| 5,125,971 A | 6/1992 | Nonami et al. | |
| 5,147,370 A | 9/1992 | McNamara et al. | |
| 5,163,958 A | 11/1992 | Pinchuk | |
| 5,195,969 A | 3/1993 | Wang et al. | |
| 5,205,921 A | 4/1993 | Shirkanzadeh | |
| 5,234,457 A | 8/1993 | Andersen | |
| 5,236,413 A | 8/1993 | Feiring | |
| 5,236,447 A | 8/1993 | Kubo et al. | |
| 5,270,086 A | 12/1993 | Hamlin | |
| 5,279,292 A | 1/1994 | Baumann et al. | |
| 5,290,585 A | 3/1994 | Elton | |
| 5,292,558 A | 3/1994 | Heller et al. | |
| 5,302,414 A | 4/1994 | Alkhimov et al. | |
| 5,304,121 A | 4/1994 | Sahatjian | |
| 5,304,195 A | 4/1994 | Twyford, Jr. et al. | |
| 5,306,286 A | 4/1994 | Stack et al. | |
| 5,314,453 A | 5/1994 | Jeutter | |
| 5,322,520 A | 6/1994 | Milder | |
| 5,342,348 A | 8/1994 | Kaplan | |
| 5,348,553 A | 9/1994 | Whitney | |
| 5,356,433 A | 10/1994 | Rowland et al. | |
| 5,360,440 A | 11/1994 | Andersen | |
| 5,366,504 A | 11/1994 | Andersen et al. | |
| 5,380,298 A | 1/1995 | Zabetakis et al. | |
| 5,383,935 A | 1/1995 | Shirkhanzadeh | |
| 5,385,776 A | 1/1995 | Maxfield et al. | |
| 5,397,307 A | 3/1995 | Goodin | |
| 5,405,367 A | 4/1995 | Schulman et al. | |
| 5,421,955 A | 6/1995 | Lau et al. | |
| 5,439,446 A | 8/1995 | Barry | |
| 5,443,458 A | 8/1995 | Eury | |
| 5,443,496 A | 8/1995 | Schwartz et al. | |
| 5,443,500 A | 8/1995 | Sigwart | |
| 5,449,373 A | 9/1995 | Pinchasik et al. | |
| 5,449,382 A | 9/1995 | Dayton | |
| 5,458,627 A | 10/1995 | Baranowski, Jr. et al. | |
| 5,462,575 A | 10/1995 | Del Corso | |
| 5,464,450 A | 11/1995 | Buscemi et al. | |
| 5,464,650 A | 11/1995 | Berg et al. | |
| 5,468,574 A | 11/1995 | Ehrenberg et al. | |
| 5,474,797 A | 12/1995 | Sioshansi et al. | |
| 5,500,013 A | 3/1996 | Buscemi et al. | |
| 5,514,154 A | 5/1996 | Lau et al. | |
| 5,527,337 A | 6/1996 | Stack et al. | |
| 5,536,573 A | 7/1996 | Rubner et al. | |
| 5,545,208 A | 8/1996 | Wolff et al. | |
| 5,549,664 A | 8/1996 | Hirata et al. | |
| 5,551,954 A | 9/1996 | Buscemi et al. | |
| 5,578,075 A | 11/1996 | Dayton | |
| 5,587,200 A | 12/1996 | Lorenz et al. | |
| 5,587,507 A | 12/1996 | Kohn et al. | |
| 5,591,222 A | 1/1997 | Susawa et al. | |
| 5,591,224 A | 1/1997 | Schwartz et al. | |
| 5,599,352 A | 2/1997 | Dinh et al. | |
| 5,603,556 A | 2/1997 | Klink | |
| 5,605,696 A | 2/1997 | Eury et al. | |
| 5,607,463 A | 3/1997 | Schwartz et al. | |
| 5,609,629 A | 3/1997 | Fearnot et al. | |
| 5,614,549 A | 3/1997 | Greenwald et al. | |
| 5,624,411 A | 4/1997 | Tuch | |
| 5,628,787 A | 5/1997 | Mayer | |
| 5,629,077 A | 5/1997 | Turnlund et al. | |
| 5,632,771 A | 5/1997 | Boatman et al. | |
| 5,632,840 A | 5/1997 | Campbell | |
| 5,649,951 A | 7/1997 | Davidson | |
| 5,658,327 A | 8/1997 | Altman et al. | |
| 5,672,242 A | 9/1997 | Jen | |
| 5,674,192 A | 10/1997 | Sahatjian et al. | |
| 5,674,242 A | 10/1997 | Phan | |
| 5,676,685 A | 10/1997 | Razavi | |
| 5,679,440 A | 10/1997 | Kubota | |
| 5,690,670 A | 11/1997 | Davidson | |
| 5,693,085 A | 12/1997 | Buirge et al. | |
| 5,693,928 A | 12/1997 | Egitto et al. | |
| 5,697,967 A | 12/1997 | Dinh et al. | |
| 5,700,286 A | 12/1997 | Tartaglia et al. | |
| 5,716,981 A | 2/1998 | Hunter et al. | |
| 5,721,049 A | 2/1998 | Marcolongo et al. | |
| 5,725,570 A | 3/1998 | Heath | |
| 5,733,925 A | 3/1998 | Kunz et al. | |
| 5,741,331 A | 4/1998 | Pinchuk | |
| 5,744,515 A | 4/1998 | Clapper | |
| 5,749,809 A | 5/1998 | Lin | |
| 5,749,880 A | 5/1998 | Banas et al. | |
| 5,758,562 A | 6/1998 | Thompson | |
| 5,759,192 A | 6/1998 | Saunders | |
| 5,761,775 A | 6/1998 | Legome et al. | |
| 5,769,883 A | 6/1998 | Buscemi et al. | |
| 5,769,884 A | 6/1998 | Solovay | |
| 5,773,925 A | 6/1998 | Kimura et al. | |
| 5,776,184 A | 7/1998 | Tuch | |
| 5,779,904 A | 7/1998 | Ruderman et al. | |
| 5,780,807 A | 7/1998 | Saunders | |
| 5,788,626 A | 8/1998 | Thompson | |
| 5,788,687 A | 8/1998 | Batich et al. | |
| 5,788,979 A | 8/1998 | Alt et al. | |
| 5,797,898 A | 8/1998 | Santini, Jr. et al. | |
| 5,800,511 A | 9/1998 | Mayer | |
| 5,815,904 A | 10/1998 | Clubb et al. | |
| 5,817,046 A | 10/1998 | Glickman | |
| 5,824,045 A | 10/1998 | Alt | |
| 5,824,048 A | 10/1998 | Tuch | |
| 5,824,077 A | 10/1998 | Mayer | |
| 5,830,217 A | 11/1998 | Ryan | |
| 5,833,715 A | 11/1998 | Vachon et al. | |
| 5,837,007 A | 11/1998 | Altman et al. | |
| 5,837,275 A | 11/1998 | Burrell et al. | |
| 5,840,387 A | 11/1998 | Berlowitz-Tarrant et al. | |
| 5,843,089 A | 12/1998 | Sahatjian et al. | |
| 5,843,172 A | 12/1998 | Yan | |
| 5,852,277 A | 12/1998 | Gustafson | |
| 5,854,382 A | 12/1998 | Loomis | |
| 5,858,556 A | 1/1999 | Eckert et al. | |
| 5,869,140 A | 2/1999 | Blohowiak et al. | |
| 5,873,904 A | 2/1999 | Ragheb et al. | |
| 5,876,756 A | 3/1999 | Takada et al. | |
| 5,879,697 A | 3/1999 | Ding et al. | |
| 5,880,661 A | 3/1999 | Davidson et al. | |
| 5,882,335 A | 3/1999 | Leone et al. | |
| 5,891,108 A | 4/1999 | Leone et al. | |
| 5,891,191 A | 4/1999 | Stinson | |
| 5,899,935 A | 5/1999 | Ding | |
| 5,902,266 A | 5/1999 | Leone et al. | |
| 5,906,759 A | 5/1999 | Richter | |
| 5,907,893 A | 6/1999 | Zadno-Azizi et al. | |
| 5,922,005 A | 7/1999 | Richter et al. | |
| 5,922,021 A | 7/1999 | Jang | |
| 5,928,247 A | 7/1999 | Barry et al. | |
| 5,935,506 A | 8/1999 | Schmitz et al. | |
| 5,938,903 A | 8/1999 | Broderick | |

| | | |
|---|---|---|
| 5,941,843 A | 8/1999 | Atanasoska et al. |
| 5,951,458 A | 9/1999 | Hastings et al. |
| 5,951,881 A | 9/1999 | Rogers et al. |
| 5,954,706 A | 9/1999 | Sahatjian |
| 5,957,975 A | 9/1999 | Lafont et al. |
| 5,958,440 A | 9/1999 | Burrell et al. |
| 5,961,547 A | 10/1999 | Razavi |
| 5,968,091 A | 10/1999 | Pinchuk et al. |
| 5,968,092 A | 10/1999 | Buscemi et al. |
| 5,972,027 A | 10/1999 | Johnson |
| 5,972,192 A | 10/1999 | Dubin et al. |
| 5,976,169 A | 11/1999 | Imran |
| 5,976,454 A | 11/1999 | Sterzel et al. |
| 5,977,204 A | 11/1999 | Boyan et al. |
| 5,980,554 A | 11/1999 | Lenker et al. |
| 5,980,564 A | 11/1999 | Stinson |
| 5,980,566 A | 11/1999 | Alt et al. |
| 6,001,125 A | 12/1999 | Golds et al. |
| 6,013,591 A | 1/2000 | Ying et al. |
| 6,017,553 A | 1/2000 | Burrell et al. |
| 6,017,577 A | 1/2000 | Hostettler et al. |
| 6,021,347 A | 2/2000 | Herbst et al. |
| 6,025,036 A | 2/2000 | McGill et al. |
| 6,027,742 A | 2/2000 | Lee et al. |
| 6,034,295 A | 3/2000 | Rehberg et al. |
| 6,056,776 A | 5/2000 | Lau et al. |
| 6,063,101 A | 5/2000 | Jacobsen et al. |
| 6,071,305 A | 6/2000 | Brown et al. |
| 6,080,190 A | 6/2000 | Schwartz |
| 6,086,773 A | 7/2000 | Dufresne et al. |
| 6,096,070 A | 8/2000 | Ragheb et al. |
| 6,096,175 A | 8/2000 | Roth |
| 6,099,561 A | 8/2000 | Alt |
| 6,099,562 A | 8/2000 | Ding et al. |
| 6,106,473 A | 8/2000 | Violante et al. |
| 6,107,004 A | 8/2000 | Donadio, III |
| 6,117,592 A | 9/2000 | Hoshino et al. |
| 6,120,260 A | 9/2000 | Jirele |
| 6,120,535 A | 9/2000 | McDonald et al. |
| 6,120,660 A | 9/2000 | Chu et al. |
| 6,123,861 A | 9/2000 | Santini, Jr. et al. |
| 6,132,463 A | 10/2000 | Lee et al. |
| 6,139,573 A | 10/2000 | Sogard et al. |
| 6,139,574 A | 10/2000 | Vacanti et al. |
| 6,139,913 A | 10/2000 | Van Steenkiste et al. |
| 6,140,740 A | 10/2000 | Porat et al. |
| 6,143,370 A | 11/2000 | Panagiotou et al. |
| 6,153,252 A | 11/2000 | Hossainy et al. |
| 6,159,142 A | 12/2000 | Alt |
| 6,162,238 A | 12/2000 | Kaplan et al. |
| 6,164,284 A | 12/2000 | Schulman et al. |
| 6,165,211 A | 12/2000 | Thompson |
| 6,167,307 A | 12/2000 | Hess |
| 6,168,602 B1 | 1/2001 | Ryan |
| 6,174,329 B1 | 1/2001 | Callol et al. |
| 6,174,330 B1 | 1/2001 | Stinson |
| 6,180,222 B1 | 1/2001 | Schulz et al. |
| 9,170,488 | 1/2001 | Spillman, Jr et al. |
| 6,185,455 B1 | 2/2001 | Loeb et al. |
| 6,185,457 B1 | 2/2001 | Kroll et al. |
| 6,190,404 B1 | 2/2001 | Palmaz et al. |
| 6,192,271 B1 | 2/2001 | Hayman |
| 6,201,991 B1 | 3/2001 | Chekanov |
| 6,203,536 B1 | 3/2001 | Berg et al. |
| 6,206,914 B1 | 3/2001 | Soykan et al. |
| 6,206,915 B1 | 3/2001 | Fagan et al. |
| 6,206,916 B1 | 3/2001 | Furst |
| 6,212,434 B1 | 4/2001 | Scheiner |
| 6,214,037 B1 | 4/2001 | Mitchell et al. |
| 6,214,042 B1 | 4/2001 | Jacobsen et al. |
| 6,217,607 B1 | 4/2001 | Alt |
| 6,231,597 B1 | 5/2001 | Deem et al. |
| 6,240,616 B1 | 6/2001 | Yan |
| 6,241,762 B1 | 6/2001 | Shanley |
| 6,245,103 B1 | 6/2001 | Stinson |
| 6,245,104 B1 | 6/2001 | Alt |
| 6,249,952 B1 | 6/2001 | Ding |
| 6,251,136 B1 | 6/2001 | Guruwaiya et al. |
| 6,251,980 B1 | 6/2001 | Lan et al. |
| 6,253,252 B1 | 6/2001 | Schofield |
| 6,253,443 B1 | 7/2001 | Johnson |
| 6,254,632 B1 | 7/2001 | Wu et al. |
| 6,258,117 B1 | 7/2001 | Camrud et al. |
| 6,264,687 B1 | 7/2001 | Tomonto |
| 6,270,831 B2 | 8/2001 | Kumar et al. |
| 6,273,908 B1 | 8/2001 | Ndondo-Lay |
| 6,273,913 B1 | 8/2001 | Wright et al. |
| 6,277,078 B1 | 8/2001 | Porat et al. |
| 6,280,385 B1 | 8/2001 | Melzer et al. |
| 6,280,411 B1 | 8/2001 | Lennox |
| 6,283,386 B1 | 9/2001 | Van Steenkiste et al. |
| 6,287,331 B1 | 9/2001 | Heath |
| 6,287,332 B1 | 9/2001 | Bolz et al. |
| 6,287,335 B1 | 9/2001 | Drasler et al. |
| 6,287,628 B1 | 9/2001 | Hossainy et al. |
| 6,290,721 B1 | 9/2001 | Heath |
| 6,290,722 B1 | 9/2001 | Wang |
| 6,291,076 B1 | 9/2001 | Nakatsugawa |
| 6,299,604 B1 | 10/2001 | Ragheb et al. |
| 6,299,755 B1 | 10/2001 | Richter |
| 6,306,144 B1 | 10/2001 | Sydney et al. |
| 6,309,414 B1 | 10/2001 | Rolando et al. |
| 6,312,463 B1 | 11/2001 | Rourke et al. |
| 6,315,708 B1 | 11/2001 | Salmon et al. |
| 6,323,146 B1 | 11/2001 | Pugh et al. |
| 6,325,825 B1 | 12/2001 | Kula et al. |
| 6,327,504 B1 | 12/2001 | Dolgin et al. |
| 6,331,312 B1 | 12/2001 | Lee et al. |
| 6,335,029 B1 | 1/2002 | Kamath et al. |
| 6,337,076 B1 | 1/2002 | Studin |
| 6,338,739 B1 | 1/2002 | Datta et al. |
| 6,342,507 B1 | 1/2002 | Naicker et al. |
| 6,344,055 B1 | 2/2002 | Shukov |
| 6,348,960 B1 | 2/2002 | Etori et al. |
| 6,358,276 B1 | 3/2002 | Edwin |
| 6,364,823 B1 | 4/2002 | Garibaldi et al. |
| 6,364,856 B1 | 4/2002 | Ding et al. |
| 6,364,903 B2 | 4/2002 | Tseng et al. |
| 6,366,808 B1 | 4/2002 | Schroeppel et al. |
| 6,368,658 B1 | 4/2002 | Schwarz et al. |
| 6,369,355 B1 | 4/2002 | Saunders |
| 6,375,826 B1 | 4/2002 | Wang et al. |
| 6,379,382 B1 | 4/2002 | Yang et al. |
| 6,379,383 B1 | 4/2002 | Palmaz et al. |
| 6,379,392 B1 | 4/2002 | Walak |
| 6,383,214 B1 | 5/2002 | Banas et al. |
| 6,387,121 B1 | 5/2002 | Alt |
| 6,387,124 B1 | 5/2002 | Buscemi et al. |
| 6,390,967 B1 | 5/2002 | Forman et al. |
| 6,391,033 B2 | 5/2002 | Ryan |
| 6,391,052 B2 | 5/2002 | Buirge et al. |
| 6,395,326 B1 | 5/2002 | Castro et al. |
| 6,398,806 B1 | 6/2002 | You |
| 6,409,754 B1 | 6/2002 | Smith et al. |
| 6,423,092 B2 * | 7/2002 | Datta et al. .................. 623/1.15 |
| 6,425,855 B2 | 7/2002 | Tomonto |
| 6,436,133 B1 | 8/2002 | Furst et al. |
| 6,440,166 B1 | 8/2002 | Kolluri |
| 6,440,487 B1 | 8/2002 | Delfino et al. |
| 6,440,503 B1 | 8/2002 | Merdan et al. |
| 6,447,540 B1 | 9/2002 | Fontaine et al. |
| 6,458,153 B1 | 10/2002 | Bailey et al. |
| 6,468,304 B1 | 10/2002 | Dubois-Rande et al. |
| 6,471,721 B1 | 10/2002 | Dang |
| 6,471,980 B2 | 10/2002 | Sirhan et al. |
| 6,475,477 B1 | 11/2002 | Kohn et al. |
| 6,478,815 B1 | 11/2002 | Alt |
| 6,479,146 B1 | 11/2002 | Caruso et al. |
| 6,486,588 B2 | 11/2002 | Doron |
| 6,488,702 B1 | 12/2002 | Besselink |
| 6,491,666 B1 | 12/2002 | Santini, Jr. et al. |
| 6,491,720 B1 | 12/2002 | Vallana et al. |
| 6,492,096 B1 | 12/2002 | Liu et al. |
| 6,503,556 B2 | 1/2003 | Harish et al. |
| 6,503,921 B2 | 1/2003 | Naicker et al. |
| 6,506,437 B1 | 1/2003 | Harish et al. |
| 6,506,972 B1 | 1/2003 | Wang |
| 6,514,283 B2 | 2/2003 | DiMatteo et al. |

| Patent | Date | Inventors |
|---|---|---|
| 6,517,571 B1 | 2/2003 | Brauker et al. |
| 6,517,888 B1 | 2/2003 | Weber |
| 6,524,274 B1 | 2/2003 | Rosenthal et al. |
| 6,524,334 B1 | 2/2003 | Thompson |
| 6,527,801 B1 | 3/2003 | Dutta |
| 6,527,938 B2 | 3/2003 | Bales et al. |
| 6,530,949 B2 | 3/2003 | Konya et al. |
| 6,530,951 B1 | 3/2003 | Bates et al. |
| 6,537,310 B1 | 3/2003 | Palmaz et al. |
| 6,537,312 B2 | 3/2003 | Datta et al. |
| 6,544,582 B1 | 4/2003 | Yoe |
| 6,545,097 B2 | 4/2003 | Pinchuk et al. |
| 6,549,811 B2 | 4/2003 | Stewart et al. |
| 6,554,854 B1 | 4/2003 | Flanagan |
| 6,558,422 B1 | 5/2003 | Baker et al. |
| 6,558,733 B1 | 5/2003 | Hossainy et al. |
| 6,565,602 B2 | 5/2003 | Rolando et al. |
| 6,569,489 B1 | 5/2003 | Li |
| 6,584,349 B1 | 6/2003 | Sage et al. |
| 6,585,764 B2 | 7/2003 | Wright et al. |
| 6,585,765 B1 | 7/2003 | Hossainy et al. |
| 6,586,705 B1 | 7/2003 | Schell |
| 6,589,286 B1 | 7/2003 | Litner |
| 6,599,558 B1 | 7/2003 | Al-Lamee et al. |
| 6,602,287 B1 | 8/2003 | Millare et al. |
| 6,607,598 B2 | 8/2003 | Schwarz et al. |
| 6,613,077 B2 | 9/2003 | Gilligan et al. |
| 6,613,083 B2 | 9/2003 | Alt |
| 6,613,432 B2 | 9/2003 | Zamora et al. |
| 6,616,765 B1 | 9/2003 | Castro et al. |
| 6,626,933 B1 | 9/2003 | Lau et al. |
| 6,626,936 B2 | 9/2003 | Stinson |
| 6,626,939 B1 * | 9/2003 | Burnside et al. ............ 623/1.38 |
| 6,627,321 B1 | 9/2003 | Ellingsen et al. |
| 6,628,989 B1 | 9/2003 | Penner |
| 6,629,992 B2 | 10/2003 | Bigus et al. |
| 6,635,082 B1 | 10/2003 | Hossainy et al. |
| 6,638,302 B1 | 10/2003 | Curcio et al. |
| 6,641,607 B1 | 11/2003 | Hossainy et al. |
| 6,652,575 B2 | 11/2003 | Wang |
| 6,652,578 B2 | 11/2003 | Bailey et al. |
| 6,652,581 B1 | 11/2003 | Ding |
| 6,652,582 B1 | 11/2003 | Stinson |
| 6,660,034 B1 | 12/2003 | Mandrusov et al. |
| 6,663,662 B2 | 12/2003 | Pacetti et al. |
| 6,663,664 B1 | 12/2003 | Pacetti |
| 6,669,980 B2 | 12/2003 | Hansen |
| 6,673,105 B1 | 1/2004 | Chen |
| 6,673,385 B1 | 1/2004 | Ding et al. |
| 6,673,999 B1 | 1/2004 | Wang et al. |
| 6,676,987 B2 | 1/2004 | Zhong |
| 6,676,989 B2 | 1/2004 | Kirkpatrick et al. |
| 6,689,160 B1 | 2/2004 | Okuda et al. |
| 6,689,803 B2 | 2/2004 | Hunter |
| 6,695,865 B2 | 2/2004 | Boyle et al. |
| 6,696,666 B2 | 2/2004 | Merdan et al. |
| 6,696,667 B1 | 2/2004 | Flanagan |
| 6,699,281 B2 | 3/2004 | Vallana et al. |
| 6,699,282 B1 | 3/2004 | Sceusa |
| 6,709,379 B1 | 3/2004 | Brandau et al. |
| 6,709,397 B2 | 3/2004 | Taylor |
| 6,709,451 B1 | 3/2004 | Noble et al. |
| 6,710,053 B2 | 3/2004 | Naicker et al. |
| 6,712,844 B2 | 3/2004 | Pacetti |
| 6,712,845 B2 | 3/2004 | Hossainy |
| 6,713,671 B1 | 3/2004 | Wang et al. |
| 6,716,444 B1 | 4/2004 | Castro et al. |
| 6,719,987 B2 | 4/2004 | Burrell et al. |
| 6,720,402 B2 | 4/2004 | Langer et al. |
| 6,723,120 B2 | 4/2004 | Yan |
| 6,723,350 B2 | 4/2004 | Burrell et al. |
| 6,725,901 B1 | 4/2004 | Kramer et al. |
| 6,726,712 B1 | 4/2004 | Raeder-Devens |
| 6,730,117 B1 | 5/2004 | Tseng et al. |
| 6,730,120 B2 | 5/2004 | Berg et al. |
| 6,730,699 B2 | 5/2004 | Li et al. |
| 6,733,513 B2 | 5/2004 | Boyle et al. |
| 6,740,077 B1 | 5/2004 | Brandau et al. |
| 6,743,388 B2 | 6/2004 | Sridharan et al. |
| 6,752,826 B2 | 6/2004 | Holloway et al. |
| 6,752,829 B2 | 6/2004 | Kocur et al. |
| 6,753,071 B1 | 6/2004 | Pacetti |
| 6,758,859 B1 | 7/2004 | Dang et al. |
| 6,764,505 B1 | 7/2004 | Hossainy et al. |
| 6,764,579 B2 | 7/2004 | Veerasamy et al. |
| 6,764,709 B2 | 7/2004 | Flanagan |
| 6,765,144 B1 | 7/2004 | Wang et al. |
| 6,767,360 B1 | 7/2004 | Alt et al. |
| 6,770,086 B1 | 8/2004 | Girton |
| 6,770,729 B2 | 8/2004 | Van Antwerp |
| 6,774,278 B1 | 8/2004 | Ragheb et al. |
| 6,776,022 B2 | 8/2004 | Kula et al. |
| 6,776,094 B1 | 8/2004 | Whitesides et al. |
| 6,776,793 B2 | 8/2004 | Brown et al. |
| 6,780,424 B2 | 8/2004 | Claude |
| 6,783,543 B2 | 8/2004 | Jang |
| 6,790,228 B2 | 9/2004 | Hossainy et al. |
| 6,793,877 B1 | 9/2004 | Pettersen et al. |
| 6,796,435 B2 | 9/2004 | Izumi |
| 6,803,070 B2 | 10/2004 | Weber |
| 6,805,709 B1 | 10/2004 | Schaldach et al. |
| 6,805,898 B1 | 10/2004 | Wu et al. |
| 6,807,440 B2 | 10/2004 | Weber |
| RE38,653 E | 11/2004 | Igaki et al. |
| 6,815,609 B1 | 11/2004 | Wang et al. |
| 6,820,676 B2 | 11/2004 | Palmaz et al. |
| 6,827,737 B2 | 12/2004 | Hill et al. |
| 6,827,966 B2 | 12/2004 | Qiu et al. |
| 6,833,004 B2 | 12/2004 | Ishii et al. |
| 6,846,323 B2 | 1/2005 | Yip et al. |
| 6,846,841 B2 | 1/2005 | Hunter et al. |
| 6,847,837 B1 | 1/2005 | Melzer et al. |
| 6,849,085 B2 | 2/2005 | Marton |
| 6,849,089 B2 | 2/2005 | Stoll |
| 6,852,122 B2 | 2/2005 | Rush |
| 6,854,172 B2 | 2/2005 | Kaese et al. |
| 6,861,088 B2 | 3/2005 | Weber et al. |
| 6,865,810 B2 | 3/2005 | Stinson |
| 6,866,805 B2 | 3/2005 | Hong et al. |
| 6,869,443 B2 | 3/2005 | Buscemi et al. |
| 6,869,701 B1 | 3/2005 | Aita et al. |
| 6,875,227 B2 | 4/2005 | Yoon |
| 6,878,249 B2 | 4/2005 | Kouyama et al. |
| 6,884,429 B2 | 4/2005 | Koziak et al. |
| 6,887,270 B2 | 5/2005 | Miller et al. |
| 6,887,857 B2 | 5/2005 | Naimark et al. |
| 6,896,697 B1 | 5/2005 | Yip et al. |
| 6,899,731 B2 | 5/2005 | Li et al. |
| 6,899,914 B2 | 5/2005 | Schaldach et al. |
| 6,904,658 B2 | 6/2005 | Hines |
| 6,908,506 B2 | 6/2005 | Zimmermann |
| 6,908,622 B2 | 6/2005 | Barry et al. |
| 6,908,624 B2 | 6/2005 | Hossainy et al. |
| 6,913,617 B1 | 7/2005 | Reiss |
| 6,913,765 B2 | 7/2005 | Li et al. |
| 6,918,869 B2 | 7/2005 | Shaw et al. |
| 6,918,927 B2 | 7/2005 | Bates et al. |
| 6,921,390 B2 | 7/2005 | Bucay-Couto et al. |
| 6,923,996 B2 | 8/2005 | Epstein et al. |
| 6,926,735 B2 | 8/2005 | Henderson |
| 6,932,930 B2 | 8/2005 | DeSimone et al. |
| 6,936,066 B2 | 8/2005 | Palmaz et al. |
| 6,939,320 B2 | 9/2005 | Lennox |
| 6,945,993 B2 | 9/2005 | Kveen et al. |
| 6,951,053 B2 | 10/2005 | Padilla et al. |
| 6,953,560 B1 | 10/2005 | Castro et al. |
| 6,953,594 B2 | 10/2005 | Lee et al. |
| 6,954,977 B2 | 10/2005 | Maguire et al. |
| 6,955,661 B1 | 10/2005 | Herweck et al. |
| 6,955,685 B2 | 10/2005 | Escamilla et al. |
| 6,962,822 B2 | 11/2005 | Hart et al. |
| 6,964,817 B2 | 11/2005 | Date et al. |
| 6,971,813 B2 | 12/2005 | Shekalim et al. |
| 6,972,130 B1 | 12/2005 | Lee et al. |
| 6,973,718 B2 | 12/2005 | Sheppard, Jr. et al. |
| 6,979,346 B1 | 12/2005 | Hossainy et al. |
| 6,979,347 B1 | 12/2005 | Wu et al. |
| 6,979,348 B2 | 12/2005 | Sundar |

| | | |
|---|---|---|
| 6,981,986 B1 | 1/2006 | Brown et al. |
| 6,984,404 B1 | 1/2006 | Talton et al. |
| 6,986,899 B2 | 1/2006 | Hossainy et al. |
| 6,989,156 B2 | 1/2006 | Gillis |
| 6,991,709 B2 | 1/2006 | Gopalraja et al. |
| 7,001,421 B2 | 2/2006 | Cheng et al. |
| 7,004,968 B2 | 2/2006 | Lootz et al. |
| 7,011,670 B2 | 3/2006 | Radisch, Jr. |
| 7,011,678 B2 | 3/2006 | Tenerz et al. |
| 7,011,680 B2 | 3/2006 | Alt |
| 7,018,408 B2 | 3/2006 | Bailey et al. |
| 7,022,334 B1 | 4/2006 | Ding et al. |
| 7,041,130 B2 | 5/2006 | Santini, Jr. |
| 7,048,767 B2 | 5/2006 | Namavar |
| 7,048,939 B2 | 5/2006 | Elkins et al. |
| 7,052,488 B2 | 5/2006 | Uhland |
| 7,056,338 B2 | 6/2006 | Shanley et al. |
| 7,056,339 B2 | 6/2006 | Elkins et al. |
| 7,060,051 B2 | 6/2006 | Palasis |
| 7,060,240 B2 | 6/2006 | Costa et al. |
| 7,063,748 B2 | 6/2006 | Talton |
| 7,067,606 B2 | 6/2006 | Mather et al. |
| 7,070,576 B2 | 7/2006 | O'Brien et al. |
| 7,078,108 B2 | 7/2006 | Zhang et al. |
| 7,099,091 B2 | 8/2006 | Taniguchi et al. |
| 7,101,391 B2 | 9/2006 | Scheuermann et al. |
| 7,101,394 B2 | 9/2006 | Hamm et al. |
| 7,105,018 B1 | 9/2006 | Yip et al. |
| 7,105,199 B2 | 9/2006 | Blinn et al. |
| 7,108,716 B2 | 9/2006 | Burnside et al. |
| 7,157,096 B2 | 1/2007 | Zhang et al. |
| 7,160,592 B2 | 1/2007 | Rypacek et al. |
| 7,163,715 B1 | 1/2007 | Kramer |
| 7,169,173 B2 | 1/2007 | Hossainy et al. |
| 7,169,178 B1 | 1/2007 | Santos et al. |
| 7,195,640 B2 | 3/2007 | Falotico et al. |
| 7,195,641 B2 | 3/2007 | Palmaz et al. |
| 7,198,675 B2 | 4/2007 | Fox et al. |
| 7,208,011 B2 | 4/2007 | Shanley et al. |
| 7,208,172 B2 | 4/2007 | Birdsall et al. |
| 7,220,816 B2 | 5/2007 | Pacetti |
| 7,226,475 B2 | 6/2007 | Lenz et al. |
| 7,229,471 B2 | 6/2007 | Gale et al. |
| 7,235,096 B1 | 6/2007 | Van Tassel et al. |
| 7,235,098 B2 | 6/2007 | Palmaz |
| 7,238,199 B2 | 7/2007 | Feldman et al. |
| 7,241,295 B2 | 7/2007 | Maguire |
| 7,244,272 B2 | 7/2007 | Dubson et al. |
| 7,261,732 B2 | 8/2007 | Justino |
| 7,261,735 B2 | 8/2007 | Llanos et al. |
| 7,267,960 B2 | 9/2007 | Galibert et al. |
| 7,279,174 B2 | 10/2007 | Pacetti |
| 7,279,175 B2 | 10/2007 | Chen et al. |
| 7,294,409 B2 | 11/2007 | Lye et al. |
| 7,311,727 B2 | 12/2007 | Mazumder et al. |
| 7,323,189 B2 | 1/2008 | Pathak |
| RE40,122 E | 2/2008 | Thompson |
| 7,331,993 B2 | 2/2008 | White |
| 7,335,375 B2 | 2/2008 | Li et al. |
| 7,344,560 B2 | 3/2008 | Gregorich et al. |
| 7,344,563 B2 | 3/2008 | Vallana et al. |
| 7,393,589 B2 | 7/2008 | Aharonov et al. |
| 7,402,173 B2 | 7/2008 | Scheuermann et al. |
| 7,416,558 B2 | 8/2008 | Yip et al. |
| 7,432,327 B2 | 10/2008 | Glasgow et al. |
| 7,462,366 B2 | 12/2008 | Lanphere |
| 7,498,385 B2 | 3/2009 | Swetlin et al. |
| 7,507,433 B2 | 3/2009 | Weber |
| 7,537,610 B2 | 5/2009 | Reiss |
| 7,547,445 B2 | 6/2009 | Chudzik et al. |
| 7,563,277 B2 | 7/2009 | Case et al. |
| 7,637,941 B1 | 12/2009 | Manicka et al. |
| 7,651,527 B2 | 1/2010 | Krivoruchko et al. |
| 7,691,401 B2 | 4/2010 | Castro et al. |
| 7,713,297 B2 | 5/2010 | Alt |
| 7,749,264 B2 | 7/2010 | Gregorich et al. |
| 7,758,635 B2 | 7/2010 | Parsonage |
| 7,771,773 B2 | 8/2010 | Namavar |
| 7,776,926 B1 | 8/2010 | Claude et al. |
| 2001/0001834 A1 | 5/2001 | Palmaz et al. |
| 2001/0002000 A1 | 5/2001 | Kumar et al. |
| 2001/0002435 A1 | 5/2001 | Berg et al. |
| 2001/0013166 A1 | 8/2001 | Yan |
| 2001/0021871 A1 | 9/2001 | Stinson |
| 2001/0021873 A1 | 9/2001 | Stinson |
| 2001/0027299 A1 | 10/2001 | Yang et al. |
| 2001/0029398 A1 | 10/2001 | Jadhav |
| 2001/0029660 A1 | 10/2001 | Johnson |
| 2001/0032011 A1 | 10/2001 | Stanford |
| 2001/0032013 A1 | 10/2001 | Marton |
| 2001/0032014 A1 | 10/2001 | Yang et al. |
| 2001/0044650 A1* | 11/2001 | Simso et al. ............... 623/1.16 |
| 2002/0000175 A1 | 1/2002 | Hintermaier et al. |
| 2002/0000406 A1 | 1/2002 | Izumi |
| 2002/0004060 A1 | 1/2002 | Heublein et al. |
| 2002/0007102 A1 | 1/2002 | Salmon et al. |
| 2002/0007209 A1 | 1/2002 | Schearder et al. |
| 2002/0010505 A1 | 1/2002 | Richter |
| 2002/0016623 A1 | 2/2002 | Kula et al. |
| 2002/0016624 A1 | 2/2002 | Patterson et al. |
| 2002/0028827 A1 | 3/2002 | Naicker et al. |
| 2002/0032477 A1 | 3/2002 | Helmus et al. |
| 2002/0035394 A1 | 3/2002 | Fierens et al. |
| 2002/0038146 A1 | 3/2002 | Harry |
| 2002/0042039 A1 | 4/2002 | Kim et al. |
| 2002/0049495 A1 | 4/2002 | Kutryk et al. |
| 2002/0051730 A1 | 5/2002 | Bodnar et al. |
| 2002/0051846 A1 | 5/2002 | Kirkpatrick et al. |
| 2002/0065553 A1 | 5/2002 | Weber |
| 2002/0082679 A1* | 6/2002 | Sirhan et al. ............... 623/1.15 |
| 2002/0087123 A1 | 7/2002 | Hossainy et al. |
| 2002/0091375 A1 | 7/2002 | Sahatjian et al. |
| 2002/0098278 A1 | 7/2002 | Bates et al. |
| 2002/0099434 A1 | 7/2002 | Buscemi et al. |
| 2002/0099438 A1 | 7/2002 | Furst |
| 2002/0103527 A1 | 8/2002 | Kocur et al. |
| 2002/0103528 A1 | 8/2002 | Schaldach et al. |
| 2002/0111694 A1 | 8/2002 | Ellingsen et al. |
| 2002/0121497 A1 | 9/2002 | Tomonto |
| 2002/0123801 A1 | 9/2002 | Pacetti et al. |
| 2002/0133222 A1 | 9/2002 | Das |
| 2002/0133224 A1 | 9/2002 | Bajgar et al. |
| 2002/0138100 A1 | 9/2002 | Stoll et al. |
| 2002/0138131 A1 | 9/2002 | Solovay et al. |
| 2002/0138136 A1 | 9/2002 | Chandresekaran et al. |
| 2002/0138154 A1 | 9/2002 | Li et al. |
| 2002/0144757 A1 | 10/2002 | Craig et al. |
| 2002/0155212 A1 | 10/2002 | Hossainy |
| 2002/0165265 A1 | 11/2002 | Hunter et al. |
| 2002/0165578 A1 | 11/2002 | Sawitowski et al. |
| 2002/0165600 A1 | 11/2002 | Banas et al. |
| 2002/0165607 A1 | 11/2002 | Alt |
| 2002/0169493 A1 | 11/2002 | Widenhouse et al. |
| 2002/0178570 A1 | 12/2002 | Sogard et al. |
| 2002/0182241 A1 | 12/2002 | Borenstein et al. |
| 2002/0183581 A1 | 12/2002 | Yoe et al. |
| 2002/0187260 A1 | 12/2002 | Sheppard, Jr. et al. |
| 2002/0193336 A1 | 12/2002 | Elkins et al. |
| 2002/0193682 A1 | 12/2002 | Torchia et al. |
| 2002/0193869 A1 | 12/2002 | Dang |
| 2002/0197178 A1 | 12/2002 | Yan |
| 2002/0198601 A1 | 12/2002 | Bales et al. |
| 2003/0003127 A1 | 1/2003 | Brown et al. |
| 2003/0003220 A1 | 1/2003 | Zhong et al. |
| 2003/0004563 A1 | 1/2003 | Jackson et al. |
| 2003/0004564 A1 | 1/2003 | Elkins et al. |
| 2003/0009214 A1 | 1/2003 | Shanley |
| 2003/0018380 A1 | 1/2003 | Craig et al. |
| 2003/0018381 A1 | 1/2003 | Whitcher et al. |
| 2003/0023300 A1 | 1/2003 | Bailey et al. |
| 2003/0028242 A1 | 2/2003 | Vallana et al. |
| 2003/0028243 A1 | 2/2003 | Bates et al. |
| 2003/0032892 A1 | 2/2003 | Erlach et al. |
| 2003/0033007 A1 | 2/2003 | Sirhan et al. |
| 2003/0044446 A1 | 3/2003 | Moro et al. |
| 2003/0044596 A1 | 3/2003 | Lazarov et al. |
| 2003/0050687 A1 | 3/2003 | Schwade et al. |
| 2003/0059640 A1 | 3/2003 | Marton et al. |

| | | | | | | |
|---|---|---|---|---|---|---|
| 2003/0060871 A1 | 3/2003 | Hill et al. | | 2004/0098119 A1 | 5/2004 | Wang |
| 2003/0060873 A1 | 3/2003 | Gertner et al. | | 2004/0106975 A1 | 6/2004 | Solovay et al. |
| 2003/0064095 A1 | 4/2003 | Martin et al. | | 2004/0106984 A1 | 6/2004 | Stinson |
| 2003/0068355 A1 | 4/2003 | Shanley et al. | | 2004/0106985 A1 | 6/2004 | Jang |
| 2003/0069631 A1 | 4/2003 | Stoll | | 2004/0111150 A1 | 6/2004 | Berg et al. |
| 2003/0074053 A1 | 4/2003 | Palmaz et al. | | 2004/0116999 A1 | 6/2004 | Ledergerber |
| 2003/0077200 A1 | 4/2003 | Craig et al. | | 2004/0117005 A1 | 6/2004 | Gadde et al. |
| 2003/0077310 A1 | 4/2003 | Pathak et al. | | 2004/0117008 A1 | 6/2004 | Wnendt et al. |
| 2003/0083614 A1 | 5/2003 | Eisert | | 2004/0122504 A1 | 6/2004 | Hogendijk |
| 2003/0083646 A1 | 5/2003 | Sirhan et al. | | 2004/0126566 A1 | 7/2004 | Axen et al. |
| 2003/0083731 A1 | 5/2003 | Kramer et al. | | 2004/0133270 A1 | 7/2004 | Grandt |
| 2003/0087024 A1 | 5/2003 | Flanagan | | 2004/0134886 A1 | 7/2004 | Wagner et al. |
| 2003/0088307 A1 | 5/2003 | Shulze et al. | | 2004/0137039 A1 | 7/2004 | Sukhishvili et al. |
| 2003/0088312 A1 | 5/2003 | Kopia et al. | | 2004/0138738 A1 | 7/2004 | Stinson |
| 2003/0099684 A1 | 5/2003 | Domb | | 2004/0142014 A1 | 7/2004 | Litvack et al. |
| 2003/0100815 A1 | 5/2003 | Da Silva et al. | | 2004/0143317 A1 | 7/2004 | Stinson et al. |
| 2003/0100830 A1 | 5/2003 | Zhong et al. | | 2004/0143321 A1 | 7/2004 | Litvack et al. |
| 2003/0104030 A1 | 6/2003 | Igaki et al. | | 2004/0148010 A1 | 7/2004 | Rush |
| 2003/0105511 A1 | 6/2003 | Welsh et al. | | 2004/0148015 A1 | 7/2004 | Lye et al. |
| 2003/0108659 A1 | 6/2003 | Bales et al. | | 2004/0153138 A1 | 8/2004 | Murphy |
| 2003/0114917 A1 | 6/2003 | Holloway et al. | | 2004/0157073 A1 | 8/2004 | Burrell et al. |
| 2003/0114921 A1 | 6/2003 | Yoon | | 2004/0158308 A1 | 8/2004 | Hogendijk et al. |
| 2003/0118692 A1 | 6/2003 | Wang et al. | | 2004/0158310 A1 | 8/2004 | Weber et al. |
| 2003/0120339 A1 | 6/2003 | Banik et al. | | 2004/0167572 A1 | 8/2004 | Roth et al. |
| 2003/0124055 A1 | 7/2003 | Li et al. | | 2004/0167612 A1 | 8/2004 | Grignani et al. |
| 2003/0125803 A1 | 7/2003 | Vallana | | 2004/0172124 A1 | 9/2004 | Vallana et al. |
| 2003/0130718 A1 | 7/2003 | Palmas et al. | | 2004/0181252 A1 | 9/2004 | Boyle et al. |
| 2003/0139799 A1 | 7/2003 | Ley et al. | | 2004/0181275 A1 | 9/2004 | Noble et al. |
| 2003/0143330 A1 | 7/2003 | Loomis et al. | | 2004/0181276 A1 | 9/2004 | Brown et al. |
| 2003/0144728 A1 | 7/2003 | Scheuermann et al. | | 2004/0181278 A1 | 9/2004 | Tseng et al. |
| 2003/0150380 A1 | 8/2003 | Yoe | | 2004/0182511 A1 | 9/2004 | Rakos et al. |
| 2003/0153901 A1 | 8/2003 | Herweck et al. | | 2004/0186553 A1 | 9/2004 | Yan |
| 2003/0158598 A1 | 8/2003 | Ashton et al. | | 2004/0191293 A1 | 9/2004 | Claude |
| 2003/0170605 A1 | 9/2003 | Long et al. | | 2004/0191404 A1 | 9/2004 | Hossainy et al. |
| 2003/0181975 A1 | 9/2003 | Ishii et al. | | 2004/0202692 A1 | 10/2004 | Shanley et al. |
| 2003/0185895 A1 | 10/2003 | Lanphere | | 2004/0204750 A1 | 10/2004 | Dinh |
| 2003/0190406 A1 | 10/2003 | Hossainy et al. | | 2004/0211362 A1 | 10/2004 | Castro et al. |
| 2003/0195613 A1 | 10/2003 | Curcio et al. | | 2004/0219214 A1 | 11/2004 | Gravett et al. |
| 2003/0204239 A1 | 10/2003 | Carlyle et al. | | 2004/0220510 A1 | 11/2004 | Koullick et al. |
| 2003/0211135 A1 | 11/2003 | Greenhalgh et al. | | 2004/0220659 A1 | 11/2004 | Girton |
| 2003/0216803 A1 | 11/2003 | Ledergerber | | 2004/0220660 A1* | 11/2004 | Shanley et al. ............... 623/1.16 |
| 2003/0219562 A1 | 11/2003 | Rypacek et al. | | 2004/0220662 A1 | 11/2004 | Dang et al. |
| 2003/0221307 A1 | 12/2003 | Kaese et al. | | 2004/0224001 A1 | 11/2004 | Pacetti et al. |
| 2003/0228523 A1 | 12/2003 | DeLongchamp et al. | | 2004/0225346 A1 | 11/2004 | Mazumder et al. |
| 2003/0236513 A1 | 12/2003 | Schwarz et al. | | 2004/0228905 A1 | 11/2004 | Greenspan et al. |
| 2004/0000046 A1 | 1/2004 | Stinson | | 2004/0230176 A1 | 11/2004 | Shanahan et al. |
| 2004/0000540 A1 | 1/2004 | Soboyejo et al. | | 2004/0230225 A1 | 11/2004 | Penner et al. |
| 2004/0004063 A1 | 1/2004 | Merdan | | 2004/0230290 A1 | 11/2004 | Weber et al. |
| 2004/0006382 A1 | 1/2004 | Sohier | | 2004/0230293 A1 | 11/2004 | Yip et al. |
| 2004/0018296 A1 | 1/2004 | Castro et al. | | 2004/0234737 A1 | 11/2004 | Pacetti |
| 2004/0019376 A1 | 1/2004 | Alt | | 2004/0236415 A1 | 11/2004 | Thomas |
| 2004/0022939 A1 | 2/2004 | Kim et al. | | 2004/0236416 A1 | 11/2004 | Falotico |
| 2004/0024448 A1 | 2/2004 | Chang et al. | | 2004/0237282 A1 | 12/2004 | Hines |
| 2004/0029303 A1 | 2/2004 | Hart et al. | | 2004/0242106 A1 | 12/2004 | Rabasco et al. |
| 2004/0030218 A1 | 2/2004 | Kocur et al. | | 2004/0243217 A1 | 12/2004 | Andersen |
| 2004/0030377 A1* | 2/2004 | Dubson et al. ............... 623/1.13 | | 2004/0243237 A1 | 12/2004 | Unwin et al. |
| 2004/0034409 A1 | 2/2004 | Heublein et al. | | 2004/0243241 A1 | 12/2004 | Istephanous et al. |
| 2004/0039438 A1 | 2/2004 | Alt | | 2004/0247671 A1 | 12/2004 | Prescott et al. |
| 2004/0039441 A1 | 2/2004 | Rowland et al. | | 2004/0249440 A1 | 12/2004 | Bucker et al. |
| 2004/0044397 A1 | 3/2004 | Stinson | | 2004/0249443 A1 | 12/2004 | Shanley et al. |
| 2004/0047980 A1 | 3/2004 | Pacetti et al. | | 2004/0249444 A1 | 12/2004 | Reiss |
| 2004/0059407 A1 | 3/2004 | Escamilla et al. | | 2004/0249445 A1 | 12/2004 | Rosenthal et al. |
| 2004/0059409 A1 | 3/2004 | Stenzel | | 2004/0249449 A1 | 12/2004 | Shanley et al. |
| 2004/0067301 A1 | 4/2004 | Ding | | 2004/0254419 A1 | 12/2004 | Wang et al. |
| 2004/0071861 A1 | 4/2004 | Mandrusov et al. | | 2004/0254635 A1 | 12/2004 | Shanley et al. |
| 2004/0073155 A1 | 4/2004 | Laufer et al. | | 2005/0004661 A1 | 1/2005 | Lewis et al. |
| 2004/0073284 A1 | 4/2004 | Bates et al. | | 2005/0010275 A1 | 1/2005 | Sahatjian |
| 2004/0073293 A1 | 4/2004 | Thompson | | 2005/0010279 A1 | 1/2005 | Tenerz et al. |
| 2004/0073297 A1 | 4/2004 | Rohde et al. | | 2005/0015142 A1 | 1/2005 | Austin et al. |
| 2004/0073298 A1 | 4/2004 | Hossainy | | 2005/0019265 A1 | 1/2005 | Hammer et al. |
| 2004/0078071 A1 | 4/2004 | Escamilla et al. | | 2005/0019371 A1 | 1/2005 | Anderson et al. |
| 2004/0082682 A1 | 4/2004 | Loomis et al. | | 2005/0021127 A1 | 1/2005 | Kawula |
| 2004/0088038 A1 | 5/2004 | Dehnad et al. | | 2005/0021128 A1 | 1/2005 | Nakahama et al. |
| 2004/0088041 A1 | 5/2004 | Stanford | | 2005/0022627 A1 | 2/2005 | Chen |
| 2004/0093071 A1 | 5/2004 | Jang | | 2005/0027350 A1 | 2/2005 | Momma et al. |
| 2004/0093075 A1* | 5/2004 | Kuehne ........................ 623/1.15 | | 2005/0033407 A1 | 2/2005 | Weber et al. |
| 2004/0093076 A1 | 5/2004 | White et al. | | 2005/0033411 A1 | 2/2005 | Wu et al. |
| 2004/0098089 A1 | 5/2004 | Weber | | 2005/0033412 A1 | 2/2005 | Wu et al. |
| 2004/0098108 A1 | 5/2004 | Harder et al. | | 2005/0033417 A1 | 2/2005 | Borges et al. |

| | | | | | | |
|---|---|---|---|---|---|---|
| 2005/0037047 A1 | 2/2005 | Song | | 2005/0216075 A1 | 9/2005 | Wang et al. |
| 2005/0037050 A1 | 2/2005 | Weber | | 2005/0220853 A1 | 10/2005 | Dao et al. |
| 2005/0038134 A1 | 2/2005 | Loomis et al. | | 2005/0221072 A1 | 10/2005 | Dubrow et al. |
| 2005/0038501 A1 | 2/2005 | Moore, Jr. et al. | | 2005/0222671 A1 | 10/2005 | Schaeffer et al. |
| 2005/0042288 A1 | 2/2005 | Koblish et al. | | 2005/0228477 A1 | 10/2005 | Grainger et al. |
| 2005/0042440 A1 | 2/2005 | Bach et al. | | 2005/0228483 A1 | 10/2005 | Kaplan et al. |
| 2005/0055044 A1 | 3/2005 | Kangas | | 2005/0228491 A1 | 10/2005 | Snyder et al. |
| 2005/0055080 A1 | 3/2005 | Istephanous et al. | | 2005/0232968 A1 | 10/2005 | Palmaz et al. |
| 2005/0055085 A1 | 3/2005 | Rivron et al. | | 2005/0233965 A1 | 10/2005 | Schwartz et al. |
| 2005/0060020 A1 | 3/2005 | Jenson | | 2005/0234538 A1 | 10/2005 | Litvack et al. |
| 2005/0060021 A1 | 3/2005 | O'Brien et al. | | 2005/0244459 A1 | 11/2005 | DeWitt et al. |
| 2005/0064088 A1 | 3/2005 | Fredrickson | | 2005/0251245 A1 | 11/2005 | Sieradzki et al. |
| 2005/0069630 A1 | 3/2005 | Fox et al. | | 2005/0251249 A1 | 11/2005 | Sahatjian |
| 2005/0070989 A1 | 3/2005 | Lye et al. | | 2005/0252893 A1 | 11/2005 | Shapovalov et al. |
| 2005/0070990 A1 | 3/2005 | Stinson | | 2005/0255707 A1 | 11/2005 | Hart et al. |
| 2005/0070996 A1 | 3/2005 | Dinh et al. | | 2005/0261760 A1 | 11/2005 | Weber |
| 2005/0071016 A1 | 3/2005 | Hausdorf et al. | | 2005/0266039 A1 | 12/2005 | Weber |
| 2005/0072544 A1 | 4/2005 | Palmaz et al. | | 2005/0266040 A1 | 12/2005 | Gerberding |
| 2005/0074479 A1 | 4/2005 | Weber et al. | | 2005/0266041 A1 | 12/2005 | Gerold et al. |
| 2005/0074545 A1 | 4/2005 | Thomas | | 2005/0267560 A1 | 12/2005 | Bates et al. |
| 2005/0075714 A1 | 4/2005 | Cheng et al. | | 2005/0267561 A1 | 12/2005 | Jones et al. |
| 2005/0077305 A1 | 4/2005 | Guevara | | 2005/0271703 A1 | 12/2005 | Snyder et al. |
| 2005/0079132 A1 | 4/2005 | Wang et al. | | 2005/0271706 A1 | 12/2005 | Anderson et al. |
| 2005/0079199 A1 | 4/2005 | Heruth et al. | | 2005/0276837 A1 | 12/2005 | Anderson et al. |
| 2005/0079356 A1 | 4/2005 | Rathenow et al. | | 2005/0278016 A1 | 12/2005 | Welsh et al. |
| 2005/0092615 A1 | 5/2005 | Birdsall et al. | | 2005/0278021 A1 | 12/2005 | Bates et al. |
| 2005/0096731 A1 | 5/2005 | Looi et al. | | 2005/0281863 A1 | 12/2005 | Anderson et al. |
| 2005/0100577 A1 | 5/2005 | Parker et al. | | 2005/0283224 A1 | 12/2005 | King |
| 2005/0100609 A1 | 5/2005 | Claude | | 2005/0283229 A1 | 12/2005 | Dugan et al. |
| 2005/0102025 A1 | 5/2005 | Laroche et al. | | 2005/0287188 A1 | 12/2005 | Anderson et al. |
| 2005/0106212 A1 | 5/2005 | Gertner et al. | | 2006/0002979 A1 | 1/2006 | Ashammakhi et al. |
| 2005/0107869 A1 | 5/2005 | Sirhan et al. | | 2006/0009839 A1 | 1/2006 | Tan |
| 2005/0107870 A1 | 5/2005 | Wang et al. | | 2006/0013850 A1 | 1/2006 | Domb |
| 2005/0113936 A1 | 5/2005 | Brustad et al. | | 2006/0014039 A1 | 1/2006 | Zhang et al. |
| 2005/0119723 A1 | 6/2005 | Peacock | | 2006/0015175 A1 | 1/2006 | Palmaz et al. |
| 2005/0129727 A1 | 6/2005 | Weber et al. | | 2006/0015361 A1 | 1/2006 | Sattler et al. |
| 2005/0129731 A1 | 6/2005 | Horres et al. | | 2006/0020742 A1 | 1/2006 | Au et al. |
| 2005/0131509 A1 | 6/2005 | Atanassoska et al. | | 2006/0025848 A1 | 2/2006 | Weber et al. |
| 2005/0131521 A1 | 6/2005 | Marton | | 2006/0035026 A1 | 2/2006 | Atanassoska et al. |
| 2005/0131522 A1 | 6/2005 | Stinson et al. | | 2006/0036281 A1 | 2/2006 | Patterson et al. |
| 2005/0131527 A1 | 6/2005 | Pathak | | 2006/0036311 A1 | 2/2006 | Nakayama et al. |
| 2005/0131528 A1 | 6/2005 | Buscemi et al. | | 2006/0038027 A1 | 2/2006 | O'Connor et al. |
| 2005/0136090 A1 | 6/2005 | Falotico et al. | | 2006/0040388 A1 | 2/2006 | Bromberg et al. |
| 2005/0137677 A1 | 6/2005 | Rush | | 2006/0041182 A1 | 2/2006 | Forbes et al. |
| 2005/0137679 A1 | 6/2005 | Changelian et al. | | 2006/0051397 A1 | 3/2006 | Maier et al. |
| 2005/0137684 A1 | 6/2005 | Changelian et al. | | 2006/0052744 A1 | 3/2006 | Weber |
| 2005/0149169 A1 | 7/2005 | Wang et al. | | 2006/0052863 A1 | 3/2006 | Harder et al. |
| 2005/0149170 A1 | 7/2005 | Tassel et al. | | 2006/0052864 A1 | 3/2006 | Harder et al. |
| 2005/0149175 A1 | 7/2005 | Hunter et al. | | 2006/0058868 A1 | 3/2006 | Gale et al. |
| 2005/0149177 A1 | 7/2005 | Weber et al. | | 2006/0062820 A1 | 3/2006 | Gertner et al. |
| 2005/0159804 A1 | 7/2005 | Lad et al. | | 2006/0064160 A1 | 3/2006 | Gerold et al. |
| 2005/0159805 A1 | 7/2005 | Weber et al. | | 2006/0067908 A1 | 3/2006 | Ding |
| 2005/0159809 A1 | 7/2005 | Hezi-Yamit et al. | | 2006/0069427 A1 | 3/2006 | Savage et al. |
| 2005/0160600 A1 | 7/2005 | Bien et al. | | 2006/0075044 A1 | 4/2006 | Fox et al. |
| 2005/0163821 A1 | 7/2005 | Sung et al. | | 2006/0075092 A1 | 4/2006 | Kidokoro |
| 2005/0163954 A1 | 7/2005 | Shaw | | 2006/0079958 A1 | 4/2006 | Stratford et al. |
| 2005/0165301 A1 | 7/2005 | Smith et al. | | 2006/0085062 A1 | 4/2006 | Lee et al. |
| 2005/0165468 A1 | 7/2005 | Marton | | 2006/0085065 A1 | 4/2006 | Krause et al. |
| 2005/0165470 A1 | 7/2005 | Weber | | 2006/0088566 A1 | 4/2006 | Parsonage et al. |
| 2005/0169969 A1 | 8/2005 | Li et al. | | 2006/0088567 A1 | 4/2006 | Warner et al. |
| 2005/0171595 A1 | 8/2005 | Feldman et al. | | 2006/0088653 A1 | 4/2006 | Chappa et al. |
| 2005/0177226 A1 | 8/2005 | Banik et al. | | 2006/0088666 A1 | 4/2006 | Kobrin et al. |
| 2005/0180919 A1 | 8/2005 | Tedeschi | | 2006/0100696 A1 | 5/2006 | Atanasoska et al. |
| 2005/0182361 A1 | 8/2005 | Lennox | | 2006/0115512 A1 | 6/2006 | Peacock et al. |
| 2005/0182478 A1 | 8/2005 | Holman et al. | | 2006/0118236 A1 | 6/2006 | House et al. |
| 2005/0186250 A1 | 8/2005 | Gertner et al. | | 2006/0122694 A1 | 6/2006 | Stinson et al. |
| 2005/0187605 A1 | 8/2005 | Greenhalgh et al. | | 2006/0122697 A1 | 6/2006 | Shanley et al. |
| 2005/0187611 A1 | 8/2005 | Ding et al. | | 2006/0124472 A1 | 6/2006 | Rokicki |
| 2005/0192657 A1 | 9/2005 | Colen et al. | | 2006/0127266 A1 | 6/2006 | Miura et al. |
| 2005/0192662 A1 | 9/2005 | Ward | | 2006/0129215 A1 | 6/2006 | Helmus et al. |
| 2005/0192664 A1 | 9/2005 | Eisert | | 2006/0129222 A1 | 6/2006 | Stinson |
| 2005/0196424 A1 | 9/2005 | Chappa | | 2006/0129225 A1 | 6/2006 | Kopia et al. |
| 2005/0208098 A1 | 9/2005 | Castro et al. | | 2006/0136048 A1 | 6/2006 | Pacetti et al. |
| 2005/0208100 A1 | 9/2005 | Weber et al. | | 2006/0136051 A1 | 6/2006 | Furst et al. |
| 2005/0209680 A1 | 9/2005 | Gale et al. | | 2006/0141156 A1 | 6/2006 | Viel et al. |
| 2005/0209681 A1 | 9/2005 | Curcio et al. | | 2006/0149352 A1 | 7/2006 | Schlum |
| 2005/0211680 A1 | 9/2005 | Li et al. | | 2006/0153729 A1 | 7/2006 | Stinson et al. |
| 2005/0214951 A1 | 9/2005 | Nahm et al. | | 2006/0155361 A1 | 7/2006 | Schomig et al. |
| 2005/0216074 A1 | 9/2005 | Sahatjian | | 2006/0167543 A1 | 7/2006 | Bailey et al. |

| | | | | | | |
|---|---|---|---|---|---|---|
| 2006/0177480 A1 | 8/2006 | Sung et al. | | 2007/0135908 A1 | 6/2007 | Zhao |
| 2006/0178727 A1 | 8/2006 | Richter | | 2007/0141106 A1 | 6/2007 | Bonutti et al. |
| 2006/0184235 A1 | 8/2006 | Rivron et al. | | 2007/0142897 A1 | 6/2007 | Consigny et al. |
| 2006/0193886 A1 | 8/2006 | Owens et al. | | 2007/0142899 A1 | 6/2007 | Lootz et al. |
| 2006/0193887 A1 | 8/2006 | Owens et al. | | 2007/0148251 A1 | 6/2007 | Hossainy et al. |
| 2006/0193888 A1 | 8/2006 | Lye et al. | | 2007/0151093 A1 | 7/2007 | Curcio et al. |
| 2006/0193889 A1 | 8/2006 | Spradlin et al. | | 2007/0156231 A1 | 7/2007 | Weber |
| 2006/0193890 A1 | 8/2006 | Owens et al. | | 2007/0156248 A1 | 7/2007 | Marco et al. |
| 2006/0193892 A1 | 8/2006 | Furst et al. | | 2007/0160641 A1 | 7/2007 | Jang |
| 2006/0195142 A1 | 8/2006 | Shalaby | | 2007/0168016 A1 | 7/2007 | Gronemeyer et al. |
| 2006/0198869 A1 | 9/2006 | Furst et al. | | 2007/0173923 A1 | 7/2007 | Savage et al. |
| 2006/0199876 A1 | 9/2006 | Troczynski et al. | | 2007/0178129 A1 | 8/2007 | Flanagan |
| 2006/0200229 A1 | 9/2006 | Burgermeister et al. | | 2007/0181433 A1 | 8/2007 | Birdsall et al. |
| 2006/0200231 A1 | 9/2006 | O'Brien et al. | | 2007/0184083 A1 | 8/2007 | Coughlin |
| 2006/0200232 A1 | 9/2006 | Phaneuf et al. | | 2007/0190104 A1 | 8/2007 | Kamath et al. |
| 2006/0200233 A1 | 9/2006 | Kujawski | | 2007/0191923 A1 | 8/2007 | Weber |
| 2006/0204441 A1 | 9/2006 | Atala et al. | | 2007/0191928 A1 | 8/2007 | Rolando et al. |
| 2006/0204445 A1 | 9/2006 | Atala et al. | | 2007/0191931 A1 | 8/2007 | Weber |
| 2006/0210595 A1 | 9/2006 | Singhvi et al. | | 2007/0191943 A1 | 8/2007 | Shrivastava et al. |
| 2006/0212108 A1 | 9/2006 | Tittelbach | | 2007/0197980 A1 | 8/2007 | Barry et al. |
| 2006/0222679 A1 | 10/2006 | Shanley et al. | | 2007/0202466 A1 | 8/2007 | Schwarz et al. |
| 2006/0222844 A1 | 10/2006 | Stinson | | 2007/0207186 A1 | 9/2007 | Scanlon et al. |
| 2006/0224237 A1 | 10/2006 | Furst et al. | | 2007/0208412 A1 | 9/2007 | Elmaleh |
| 2006/0229711 A1 | 10/2006 | Yan et al. | | 2007/0219626 A1 | 9/2007 | Rolando et al. |
| 2006/0229713 A1 | 10/2006 | Shanley et al. | | 2007/0224116 A1 | 9/2007 | Chandrasekaran et al. |
| 2006/0230476 A1 | 10/2006 | Atanasoska et al. | | 2007/0224244 A1 | 9/2007 | Weber et al. |
| 2006/0233941 A1 | 10/2006 | Olson | | 2007/0225799 A1 | 9/2007 | Doty |
| 2006/0241739 A1 | 10/2006 | Besselink et al. | | 2007/0244541 A1 | 10/2007 | Schulman |
| 2006/0251701 A1 | 11/2006 | Lynn et al. | | 2007/0244569 A1 | 10/2007 | Weber et al. |
| 2006/0259133 A1 | 11/2006 | Sowinski et al. | | 2007/0250155 A1 | 10/2007 | Simpson |
| 2006/0264138 A1 | 11/2006 | Sowinski et al. | | 2007/0250156 A1 | 10/2007 | Palmaz |
| 2006/0271156 A1 | 11/2006 | Ledergerber | | 2007/0250158 A1 | 10/2007 | Krivoruchko et al. |
| 2006/0271168 A1 | 11/2006 | Kleine et al. | | 2007/0255388 A1 | 11/2007 | Rudakov et al. |
| 2006/0271169 A1 | 11/2006 | Lye et al. | | 2007/0255392 A1 | 11/2007 | Johnson |
| 2006/0271192 A1 | 11/2006 | Olsen et al. | | 2007/0264199 A1 | 11/2007 | Labhasetwar et al. |
| 2006/0275554 A1 | 12/2006 | Zhao et al. | | 2007/0264303 A1 | 11/2007 | Atanasoska et al. |
| 2006/0276875 A1* | 12/2006 | Stinson et al. ............... 623/1.15 | | 2007/0270940 A1 | 11/2007 | Doty |
| 2006/0276877 A1 | 12/2006 | Owens et al. | | 2007/0270942 A1 | 11/2007 | Thomas |
| 2006/0276878 A1 | 12/2006 | Owens et al. | | 2007/0281073 A1 | 12/2007 | Gale et al. |
| 2006/0276879 A1 | 12/2006 | Lye et al. | | 2007/0281117 A1 | 12/2007 | Kaplan et al. |
| 2006/0276884 A1 | 12/2006 | Lye et al. | | 2007/0282432 A1 | 12/2007 | Stinson et al. |
| 2006/0276885 A1 | 12/2006 | Lye et al. | | 2007/0299509 A1 | 12/2007 | Ding |
| 2006/0280770 A1 | 12/2006 | Hossainy et al. | | 2007/0299512 A1 | 12/2007 | Korzuschnik et al. |
| 2006/0287709 A1 | 12/2006 | Rao | | 2008/0003251 A1 | 1/2008 | Zhou |
| 2006/0292388 A1 | 12/2006 | Palumbo et al. | | 2008/0003256 A1 | 1/2008 | Martens et al. |
| 2007/0003589 A1 | 1/2007 | Astafieva et al. | | 2008/0003431 A1 | 1/2008 | Fellinger et al. |
| 2007/0003596 A1 | 1/2007 | Tittelbach et al. | | 2008/0004691 A1 | 1/2008 | Weber et al. |
| 2007/0020306 A1 | 1/2007 | Schultheiss | | 2008/0031765 A1 | 2/2008 | Gerold et al. |
| 2007/0027532 A1 | 2/2007 | Wang et al. | | 2008/0033522 A1 | 2/2008 | Grewe et al. |
| 2007/0032858 A1 | 2/2007 | Santos et al. | | 2008/0033530 A1 | 2/2008 | Zberg et al. |
| 2007/0032862 A1 | 2/2007 | Weber et al. | | 2008/0033531 A1 | 2/2008 | Barthel et al. |
| 2007/0032864 A1 | 2/2007 | Furst et al. | | 2008/0033533 A1 | 2/2008 | Borck |
| 2007/0034615 A1 | 2/2007 | Kleine | | 2008/0033536 A1 | 2/2008 | Wittchow |
| 2007/0036905 A1 | 2/2007 | Kramer | | 2008/0033537 A1 | 2/2008 | Tittelbach |
| 2007/0038176 A1 | 2/2007 | Weber et al. | | 2008/0033538 A1 | 2/2008 | Borck et al. |
| 2007/0038289 A1 | 2/2007 | Nishide et al. | | 2008/0033539 A1 | 2/2008 | Sternberg et al. |
| 2007/0038290 A1 | 2/2007 | Huang et al. | | 2008/0033576 A1 | 2/2008 | Gerold et al. |
| 2007/0045252 A1 | 3/2007 | Kleine et al. | | 2008/0038146 A1 | 2/2008 | Wachter et al. |
| 2007/0048350 A1 | 3/2007 | Faltico et al. | | 2008/0050413 A1 | 2/2008 | Horvers et al. |
| 2007/0050007 A1 | 3/2007 | Kondyurin et al. | | 2008/0051335 A1 | 2/2008 | Kleiner et al. |
| 2007/0050009 A1 | 3/2007 | Flanagan | | 2008/0051866 A1 | 2/2008 | Chen et al. |
| 2007/0052497 A1 | 3/2007 | Tada | | 2008/0051872 A1 | 2/2008 | Borck |
| 2007/0055349 A1 | 3/2007 | Santos et al. | | 2008/0051881 A1 | 2/2008 | Feng et al. |
| 2007/0055354 A1 | 3/2007 | Santos et al. | | 2008/0057105 A1 | 3/2008 | Atanasoska et al. |
| 2007/0055364 A1 | 3/2007 | Hossainy et al. | | 2008/0058919 A1 | 3/2008 | Kramer-Brown et al. |
| 2007/0059435 A1 | 3/2007 | Santos et al. | | 2008/0058921 A1 | 3/2008 | Lindquist |
| 2007/0065418 A1 | 3/2007 | Vallana et al. | | 2008/0058923 A1 | 3/2008 | Bertsch et al. |
| 2007/0073385 A1 | 3/2007 | Schaeffer et al. | | 2008/0069854 A1 | 3/2008 | Xiao et al. |
| 2007/0073390 A1 | 3/2007 | Lee | | 2008/0069858 A1 | 3/2008 | Weber |
| 2007/0077163 A1 | 4/2007 | Furst et al. | | 2008/0071348 A1 | 3/2008 | Boismier et al. |
| 2007/0100385 A1 | 5/2007 | Rawat et al. | | 2008/0071349 A1 | 3/2008 | Atanasoska et al. |
| 2007/0104753 A1 | 5/2007 | Flanagan | | 2008/0071350 A1 | 3/2008 | Stinson |
| 2007/0106347 A1 | 5/2007 | Lin | | 2008/0071351 A1 | 3/2008 | Flanagan et al. |
| 2007/0106363 A1 | 5/2007 | Weber | | 2008/0071352 A1 | 3/2008 | Weber et al. |
| 2007/0123131 A1 | 5/2007 | Nguyen et al. | | 2008/0071353 A1 | 3/2008 | Weber et al. |
| 2007/0123973 A1 | 5/2007 | Roth et al. | | 2008/0071355 A1 | 3/2008 | Weber et al. |
| 2007/0129789 A1 | 6/2007 | Cottone, Jr. et al. | | 2008/0071357 A1 | 3/2008 | Girton et al. |
| 2007/0129792 A1* | 6/2007 | Picart et al. ............... 623/1.46 | | 2008/0071358 A1 | 3/2008 | Weber et al. |
| 2007/0134288 A1 | 6/2007 | Parsonage et al. | | 2008/0082162 A1 | 4/2008 | Boismier et al. |

| | | | | | | |
|---|---|---|---|---|---|---|
| 2008/0086199 A1 | 4/2008 | Dave et al. | | 2009/0069884 A1 | 3/2009 | Mueller |
| 2008/0086201 A1 | 4/2008 | Weber et al. | | 2009/0076588 A1 | 3/2009 | Weber |
| 2008/0090097 A1 | 4/2008 | Shaw et al. | | 2009/0076596 A1 | 3/2009 | Adden et al. |
| 2008/0097577 A1 | 4/2008 | Atanasoska et al. | | 2009/0081293 A1 | 3/2009 | Murase et al. |
| 2008/0103589 A1 | 5/2008 | Cheng et al. | | 2009/0081450 A1 | 3/2009 | Ascher et al. |
| 2008/0103594 A1 | 5/2008 | Loffler et al. | | 2009/0088831 A1 | 4/2009 | Goto |
| 2008/0107890 A1 | 5/2008 | Bureau et al. | | 2009/0088834 A1 | 4/2009 | Wang |
| 2008/0109072 A1 | 5/2008 | Girton | | 2009/0093871 A1 | 4/2009 | Rea et al. |
| 2008/0113083 A1 | 5/2008 | Sutermeister et al. | | 2009/0095715 A1 | 4/2009 | Sabaria |
| 2008/0124373 A1 | 5/2008 | Xiao et al. | | 2009/0118809 A1 | 5/2009 | Scheuermann et al. |
| 2008/0131479 A1 | 6/2008 | Weber et al. | | 2009/0118812 A1 | 5/2009 | Kokate et al. |
| 2008/0140172 A1 | 6/2008 | Carpenter et al. | | 2009/0118813 A1 | 5/2009 | Scheuermann et al. |
| 2008/0140186 A1 | 6/2008 | Grignani et al. | | 2009/0118814 A1 | 5/2009 | Schoenle et al. |
| 2008/0145400 A1 | 6/2008 | Weber et al. | | 2009/0118815 A1 | 5/2009 | Arcand et al. |
| 2008/0147175 A1 | 6/2008 | Krivoruchko et al. | | 2009/0118818 A1 | 5/2009 | Foss et al. |
| 2008/0147177 A1 | 6/2008 | Scheuermann et al. | | 2009/0118819 A1 | 5/2009 | Merz et al. |
| 2008/0148002 A1 | 6/2008 | Fleming | | 2009/0118820 A1 | 5/2009 | Gregorich et al. |
| 2008/0152929 A1 | 6/2008 | Zhao | | 2009/0118821 A1 | 5/2009 | Scheuermann et al. |
| 2008/0160166 A1 | 7/2008 | Rypacek et al. | | 2009/0118822 A1 | 5/2009 | Holman et al. |
| 2008/0160259 A1 | 7/2008 | Nielson et al. | | 2009/0118823 A1 | 5/2009 | Atanasoska et al. |
| 2008/0161906 A1 | 7/2008 | Atanasoska et al. | | 2009/0123517 A1 | 5/2009 | Flanagan et al. |
| 2008/0171929 A1 | 7/2008 | Katims | | 2009/0123521 A1 | 5/2009 | Weber et al. |
| 2008/0175885 A1 | 7/2008 | Asgari | | 2009/0124956 A1 | 5/2009 | Swetlin et al. |
| 2008/0177378 A1 | 7/2008 | Asgari | | 2009/0131540 A1 | 5/2009 | Hiromoto et al. |
| 2008/0183269 A2 | 7/2008 | Kaplan et al. | | 2009/0143855 A1 | 6/2009 | Weber et al. |
| 2008/0183277 A1 | 7/2008 | Atanasoska et al. | | 2009/0149942 A1 | 6/2009 | Edelman et al. |
| 2008/0183278 A1 | 7/2008 | Atanasoska et al. | | 2009/0157165 A1 | 6/2009 | Miller et al. |
| 2008/0188927 A1 | 8/2008 | Rohde et al. | | 2009/0157172 A1 | 6/2009 | Kokate et al. |
| 2008/0195170 A1 | 8/2008 | Asgari | | 2009/0164002 A1 | 6/2009 | Becher et al. |
| 2008/0195189 A1 | 8/2008 | Asgari | | 2009/0171452 A1 | 7/2009 | Yamamoto et al. |
| 2008/0195198 A1 | 8/2008 | Asgari | | 2009/0177273 A1 | 7/2009 | Piveteau et al. |
| 2008/0208308 A1 | 8/2008 | Allen et al. | | 2009/0182290 A1 | 7/2009 | Harder et al. |
| 2008/0208313 A1 | 8/2008 | Yu et al. | | 2009/0182337 A1 | 7/2009 | Stopek et al. |
| 2008/0208352 A1 | 8/2008 | Krivoruchko et al. | | 2009/0182425 A1 | 7/2009 | Duda et al. |
| 2008/0213377 A1 | 9/2008 | Bhatia et al. | | 2009/0192571 A1 | 7/2009 | Stett et al. |
| 2008/0215129 A1 | 9/2008 | Venturelli et al. | | 2009/0192594 A1 | 7/2009 | Borck |
| 2008/0215139 A1 | 9/2008 | McMorrow et al. | | 2009/0192595 A1 | 7/2009 | Nagura et al. |
| 2008/0215140 A1 | 9/2008 | Borck et al. | | 2009/0192596 A1 | 7/2009 | Adden |
| 2008/0241218 A1 | 10/2008 | McMorrow et al. | | 2009/0196899 A1 | 8/2009 | Birdsall et al. |
| 2008/0243113 A1 | 10/2008 | Shastri et al. | | 2009/0198320 A1 | 8/2009 | Mueller et al. |
| 2008/0243230 A1 | 10/2008 | Lootz et al. | | 2009/0202610 A1 | 8/2009 | Wilson |
| 2008/0243231 A1 | 10/2008 | Flanagan et al. | | 2009/0204203 A1 | 8/2009 | Allen et al. |
| 2008/0243234 A1 | 10/2008 | Wilcox | | 2009/0208428 A1 | 8/2009 | Hill et al. |
| 2008/0243240 A1 | 10/2008 | Doty et al. | | 2009/0208555 A1 | 8/2009 | Kuttler et al. |
| 2008/0243242 A1 | 10/2008 | Kappelt et al. | | 2009/0214373 A1 | 8/2009 | Stinson et al. |
| 2008/0249600 A1 | 10/2008 | Atanasoska et al. | | 2009/0220612 A1 | 9/2009 | Perera |
| 2008/0249615 A1 | 10/2008 | Weber | | 2009/0228037 A1 | 9/2009 | Rego |
| 2008/0255508 A1 | 10/2008 | Wang | | 2009/0240323 A1 | 9/2009 | Wilcox |
| 2008/0255509 A1 | 10/2008 | Wang | | 2009/0254171 A1 | 10/2009 | Heikkila |
| 2008/0262589 A1 | 10/2008 | Nagura | | 2009/0259300 A1 | 10/2009 | Dorogy, Jr. et al. |
| 2008/0268308 A1 | 10/2008 | Schilling et al. | | 2009/0270979 A1 | 10/2009 | Adden |
| 2008/0269872 A1 | 10/2008 | Lootz et al. | | 2009/0274737 A1 | 11/2009 | Borck |
| 2008/0288048 A1 | 11/2008 | Rolando et al. | | 2009/0281613 A1 | 11/2009 | Atanasoska et al. |
| 2008/0290467 A1 | 11/2008 | Shue | | 2009/0287301 A1 | 11/2009 | Weber |
| 2008/0294236 A1 | 11/2008 | Anand et al. | | 2009/0287302 A1 | 11/2009 | Thomas et al. |
| 2008/0294246 A1 | 11/2008 | Scheuermann | | 2009/0306584 A1 | 12/2009 | Schmidtlein et al. |
| 2008/0306584 A1 | 12/2008 | Kramer-Brown | | 2009/0306756 A1 | 12/2009 | Cho et al. |
| 2009/0005862 A1 | 1/2009 | Nakatani et al. | | 2009/0306765 A1 | 12/2009 | Weber |
| 2009/0012599 A1 | 1/2009 | Broome et al. | | 2009/0306766 A1 | 12/2009 | McDermott et al. |
| 2009/0018639 A1 | 1/2009 | Kuehling | | 2009/0311300 A1 | 12/2009 | Wittchow |
| 2009/0018647 A1 | 1/2009 | Benco et al. | | 2009/0312807 A1 | 12/2009 | Boudreault et al. |
| 2009/0018648 A1 | 1/2009 | Wittchow | | 2009/0319035 A1 | 12/2009 | Terry |
| 2009/0022771 A1 | 1/2009 | Lynn et al. | | 2009/0324684 A1 | 12/2009 | Atanasoska et al. |
| 2009/0024199 A1 | 1/2009 | Birdsall et al. | | 2009/0326638 A1 | 12/2009 | Atanasoska et al. |
| 2009/0024209 A1 | 1/2009 | Ozdil et al. | | 2010/0008970 A1 | 1/2010 | O'Brien et al. |
| 2009/0024210 A1 | 1/2009 | Klocke et al. | | 2010/0010621 A1 | 1/2010 | Klocke |
| 2009/0024211 A1 | 1/2009 | Wittchow | | 2010/0010640 A1 | 1/2010 | Gerold et al. |
| 2009/0028785 A1 | 1/2009 | Clarke | | 2010/0015206 A1 | 1/2010 | Flanagan et al. |
| 2009/0030494 A1 | 1/2009 | Stefanadis et al. | | 2010/0016940 A1 | 1/2010 | Shokoohi et al. |
| 2009/0030500 A1 | 1/2009 | Weber et al. | | 2010/0021523 A1 | 1/2010 | Scheuermann et al. |
| 2009/0030504 A1 | 1/2009 | Weber et al. | | 2010/0023112 A1 | 1/2010 | Borck et al. |
| 2009/0030506 A1 | 1/2009 | Klocke et al. | | 2010/0023116 A1 | 1/2010 | Borck et al. |
| 2009/0030507 A1 | 1/2009 | Klocke et al. | | 2010/0028436 A1 | 2/2010 | Ohrlander et al. |
| 2009/0035351 A1 | 2/2009 | Berglund et al. | | 2010/0030326 A1 | 2/2010 | Radhakrishnan et al. |
| 2009/0043330 A1 | 2/2009 | To | | 2010/0034899 A1 | 2/2010 | Harder et al. |
| 2009/0043374 A1 | 2/2009 | Nakano | | 2010/0042205 A1 | 2/2010 | Atanasoska et al. |
| 2009/0043380 A1 | 2/2009 | Blaha et al. | | 2010/0042206 A1 | 2/2010 | Yadav et al. |
| 2009/0048660 A1 | 2/2009 | Adden | | 2010/0047312 A1 | 2/2010 | Wittchow |
| 2009/0062905 A1 | 3/2009 | Moore, Jr. et al. | | 2010/0047324 A1 | 2/2010 | Fritz et al. |

| | | |
|---|---|---|
| 2010/0049146 A1 | 2/2010 | Nielsen et al. |
| 2010/0049296 A1 | 2/2010 | Sarasam et al. |
| 2010/0049299 A1 | 2/2010 | Popowski et al. |
| 2010/0049300 A1 | 2/2010 | Harder |
| 2010/0055151 A1 | 3/2010 | Flanagan |
| 2010/0057188 A1 | 3/2010 | Weber |
| 2010/0057197 A1 | 3/2010 | Weber et al. |
| 2010/0070024 A1 | 3/2010 | Venturelli et al. |
| 2010/0075162 A1 | 3/2010 | Yang et al. |
| 2010/0076544 A1 | 3/2010 | Hoffmann et al. |
| 2010/0076556 A1 | 3/2010 | Tomantschger et al. |
| 2010/0081735 A1 | 4/2010 | Mao et al. |
| 2010/0082092 A1 | 4/2010 | Gerold |
| 2010/0087910 A1 | 4/2010 | Weber |
| 2010/0087911 A1 | 4/2010 | Mueller |
| 2010/0087914 A1 | 4/2010 | Bayer et al. |
| 2010/0087915 A1 | 4/2010 | Bayer et al. |
| 2010/0087916 A1 | 4/2010 | Bayer et al. |
| 2010/0092535 A1 | 4/2010 | Cook et al. |
| 2010/0106243 A1 | 4/2010 | Wittchow |
| 2010/0119576 A1 | 5/2010 | Harder et al. |
| 2010/0119581 A1 | 5/2010 | Gratz et al. |
| 2010/0121432 A1 | 5/2010 | Klocke et al. |
| 2010/0125325 A1 | 5/2010 | Allen et al. |
| 2010/0125328 A1 | 5/2010 | Flanagan |
| 2010/0131050 A1 | 5/2010 | Zhao |
| 2010/0131052 A1 | 5/2010 | Kappelt et al. |
| 2010/0161031 A1 | 6/2010 | Papirov et al. |
| 2010/0217370 A1 | 8/2010 | Scheuermann et al. |

FOREIGN PATENT DOCUMENTS

| | | |
|---|---|---|
| AU | 2003 203 722 | 11/2003 |
| CA | 2 235 031 | 10/1998 |
| CA | 2 346 857 | 5/2000 |
| CA | 2 371 800 | 8/2000 |
| DE | 198 11 033 | 8/1999 |
| DE | 198 56 983 | 12/1999 |
| DE | 103 57 281 | 7/2005 |
| DE | 103 61 941 | 7/2005 |
| DE | 10 2006 38236 | 2/2008 |
| EP | 0 006 544 | 6/1979 |
| EP | 0 337 035 | 10/1989 |
| EP | 0 923 389 | 7/1998 |
| EP | 0 923 912 | 6/1999 |
| EP | 0 966 979 | 12/1999 |
| EP | 0 972 563 | 1/2000 |
| EP | 1 054 644 | 11/2000 |
| EP | 1 071 490 | 1/2001 |
| EP | 1 222 901 | 7/2002 |
| EP | 1 260 214 | 11/2002 |
| EP | 1 270 023 | 1/2003 |
| EP | 1 273 314 | 1/2003 |
| EP | 1 370 306 | 12/2003 |
| EP | 1 389 471 | 2/2004 |
| EP | 1 393 766 | 3/2004 |
| EP | 1 419 793 | 5/2004 |
| EP | 0 951 877 | 6/2004 |
| EP | 0 875 218 | 2/2005 |
| EP | 1 733 746 | 12/2006 |
| EP | 1 752 167 | 2/2007 |
| EP | 1 465 552 | 5/2007 |
| EP | 1 835 042 | 9/2007 |
| EP | 1 750 780 | 10/2007 |
| EP | 1 562 565 | 3/2008 |
| EP | 1 642 551 | 12/2008 |
| EP | 1 653 885 | 4/2009 |
| EP | 1 632 256 | 9/2009 |
| EP | 1 703 858 | 10/2009 |
| EP | 2 139 535 | 1/2010 |
| EP | 1 883 380 | 3/2010 |
| EP | 2 189 169 | 5/2010 |
| RU | 2 218 242 | 12/2003 |
| WO | 93/04118 | 3/1993 |
| WO | WO 97/11724 | 4/1997 |
| WO | 98/29025 | 7/1998 |
| WO | WO 98/48851 | 11/1998 |
| WO | 99/33410 | 7/1999 |
| WO | WO 99/47077 | 9/1999 |
| WO | WO 99/64580 | 12/1999 |
| WO | WO 00/25841 | 5/2000 |
| WO | WO 00/48660 | 8/2000 |
| WO | WO 00/51136 | 8/2000 |
| WO | 00/54704 | 9/2000 |
| WO | WO 00/66190 | 11/2000 |
| WO | WO 01/49338 | 7/2001 |
| WO | WO 01/78906 | 10/2001 |
| WO | 01/80920 | 11/2001 |
| WO | 01/87371 | 11/2001 |
| WO | WO 02/45764 | 6/2002 |
| WO | WO 02/47739 | 6/2002 |
| WO | WO 02/053202 | 7/2002 |
| WO | WO 03/002243 | 1/2003 |
| WO | WO 03/013396 | 2/2003 |
| WO | 03/035134 | 5/2003 |
| WO | WO 03/035131 | 5/2003 |
| WO | WO 03/035278 | 5/2003 |
| WO | WO 03/063733 | 8/2003 |
| WO | WO 03/094990 | 11/2003 |
| WO | 2004/029313 | 4/2004 |
| WO | 2004/043292 | 5/2004 |
| WO | WO 2004/093643 | 11/2004 |
| WO | 2005/025449 | 3/2005 |
| WO | WO 2005/065576 | 7/2005 |
| WO | 2005/079335 | 9/2005 |
| WO | WO 2005/110395 | 11/2005 |
| WO | WO 2005/118019 | 12/2005 |
| WO | WO 2006/008739 | 1/2006 |
| WO | WO 2006/060033 | 6/2006 |
| WO | WO 2006/060534 | 6/2006 |
| WO | WO 2006/065356 | 6/2006 |
| WO | WO 2006/077154 | 7/2006 |
| WO | 2006/080381 | 8/2006 |
| WO | 2006/097503 | 9/2006 |
| WO | 2006/104644 | 10/2006 |
| WO | WO 2006/108065 | 10/2006 |
| WO | WO 2007/005806 | 1/2007 |
| WO | WO 2007/013102 | 2/2007 |
| WO | WO 2007/018931 | 2/2007 |
| WO | WO 2007/024552 | 3/2007 |
| WO | WO 2007/035791 | 3/2007 |
| WO | 2007/079363 | 7/2007 |
| WO | WO 2007/079636 | 7/2007 |
| WO | WO 2007/082147 | 9/2007 |
| WO | 2007/139668 | 12/2007 |
| WO | 2008/003450 | 3/2008 |
| WO | 2008/034048 | 3/2008 |
| WO | 2008/034066 | 3/2008 |
| WO | 2008/036457 | 3/2008 |
| WO | 2008/036548 | 3/2008 |
| WO | 2008/036554 | 3/2008 |
| WO | WO 2008/062414 | 5/2008 |
| WO | 2008/092436 | 8/2008 |
| WO | 2008/106271 | 9/2008 |
| WO | 2008/118606 | 10/2008 |
| WO | WO 2008/117315 | 10/2008 |
| WO | 2009/045773 | 4/2009 |

OTHER PUBLICATIONS

A. Antipov, et al., "Polyelectrolyte Multilayer Capsules as Vehicles with Tunable Permeability", *Advances in Colloid and Interface Science*, 111 (2004), pp. 49-61.

A. Artyukhin, et al., "Layer-by-Layer Electrostatic Self-Assembly of Polyelectrolyte Nanoshells on Individual Carbon Nanotube Templates", Langmuir, 20 (2004), pp. 1442-1448.

C. Berkland, et al., Controlling Surface Nano-structure Using Flow-Limited Field-Injection Electrostatic Spraying (FFESS) of poly(D,L-lactide-*co*-glycolide), *Biomaterials* 25 (2004), pp. 5649-5658.

C.C. Berry et al., "Functionalisation of magnetic nanoparticles for applications in biomedicine", *J. Phys. D: Appl. Phys.* 36 (2003) pp. R198-R206.

Caruso et al., "Ultrathin Molybdenum Polyoxometalate-Polyelectrolyte Multilayer Films", *Langmuir* 14 (1998), pp. 3462-3465.

A. Duygu, "Controlled Release Systems," http://www.biomed.metu.edu.tr/courses/term _papers/contr-rel-sys_duygu.htm (Dec. 30, 2005).

T.R. Farhat et al., "Corrosion Control Using Polyelectrolyte Multilayers", *Electrochemical and Solid State Letters* 5(4) (2002), pp. B13-B15.

W.L.W. Hau et al., "Surface-Chemistry Technology for Microfluidics", *J. Micromech. Microeng.* 13 (2003), pp. 272-278.

H. Kong et al., "Polyelectrolyte-functionalized multiwalled carbon nanotubes: preparation, characterization and layer-by-layer self assembly", *Polymer* 46 (2005), pp. 2472-2485.

Kurth et al., "Multilayer on Solid Planar Substrates: From Structure to Function", *Multi-layer Thin Films Sequential Assembly of Nanocomposite Materials*, VCH ISBN 3-527-30440-1, Chapter 14 (2003), pp. 393-426.

Liu et al., "Functional Polyoxometalate Thin Films via Electrostatic Layer-by-Layer Self-Assembly", *Journal of Cluster Science*, 14(3) (2003), pp. 405-419.

F. Matsuoka, et al., "Hyperthermia Using Magnetite Cationic Liposomes for Hamster Osteosarcoma", *Biomagnetic Research and Technology*, Mar. 25, 2004, pp. 1-6.

G. C. Rutledge, et al., "Electrostatic Spinning and Properties of Ultrafine Fibers," National Textile Center Annual Report: Nov. 2001, M01-D22, pp. 1-10.

Y. M. Shin, "Experimental Characterization of Electrospinning: the Electrically Forced Jet and Instabilities", *Polymer*, 42 (2001), pp. 9955-9967.

S. Shenoy, et al., "Role of Chain Entanglements on Fiber Formation During Electrospinning of Polymer Solutions: Good Solvent, Non-Specific Polymer-polymer Interaction Limit," *Polymer*, 46 (2005) 3372-3384.

G. Sukhorukov, et al., "Comparative Analysis of Hollow and Filled Polyelectrolyte Microcapsules Templated on Melamine Formaldehyde and Carbonate Cores," *Macromol. Chem. Phys.*, 205 (2004), pp. 530-535.

S-H. Tan, et al., "Systematic Parameter Study for Ultra-Fine Fiber Fabrication Via Electrospinning Process", *Polymer*, 46 (2005), pp. 6128-6134.

P. Vermette, et al., "Immobilized Liposome Layers for Drug Delivery Applications", *Journal of Controlled Release*, 80 (2002), pp. 179-195.

Zhang et al., "Ways for fabricating stable layer-by layer self-assemblies: combined ionic self-assembly and post chemical reaction", *Colloids and Surfaces A: physiochemical and Engineering Aspects* (2002), pp. 198-200, 439-442.

Zhang et al., "Improving multilayer films endurance by photoinduced interaction between Dawson-type polyoxometalate and diazo resin", *Materials Chemistry and Physics* 90 (2005), pp. 57-52.

J. Zhang, et al., "Natural Polyelectrolyte Films Based on Layer-by Layer Deposition of Collagen and Hyaluronic Acid", *Biomaterials*, 26 (2005), pp. 3353-3361.

U.S. Appl. No. 60/826,002, filed Sep. 18, 2006, Girton et al.

U.S. Appl. No. 60/862,318, filed Oct. 20, 2006, Atanasoska et al.

U.S. Appl. No. 60/845,136, filed Sep. 15, 2006, Weber et al.

"Galvanic cell" printout from wikipedia, 2 pgs, printed Oct. 28, 2005.

"Galvanic corrosion", http://www.corrosion-doctors.org/Aircraft/galvdefi.htm, 3 pgs., printed Oct. 28, 2005.

"Galvanic series" printout from Wikipedia, p. 1 of 2, printed Oct. 28, 2005.

"Best of the ACC Scientific Session 2002," *Rev. Cardiovasc. Med.*, 2002, 3(2):85-104.

"Corrosion Theory and Corrosion Protection," *EM 1110-2-3400*, 1995, 8 pages.

Aghion et al., "Newly Developed Magnesium Alloys for Powertrain Applications," *JOM*, 2003, p. 30.

Andión et al., "Corrosion behaviour at the interface of steel bars embedded in cement slurries. Effect of phenol polymer coatings," *Corrosion Science*, 2002, 44:2805-2816.

Antipov et al., "Polyelectrolyte Multilayer Capsules as Vehicles with Tunable Permeability," *Advances in Colloid and Interface Science*, 2004, 111:49-61.

Arts et al., "Polyphenols and disease risk in epidemiologic studies," *Am. J. Clin. Nutr.*, 2005, 81:317S-325S.

Bach et al., "Corrosion, Protection and Repassivation After the Deformation of Magnesium Alloys Coated With a Protective Magnesium Fluoride Layer," *JOM*, 2004, p. 343.

Bakkar et al., "Improving corrosion resistance of magnesium-based alloys by surface modification with hydrogen by electrochemical ion reduction (EIR) and by plasma immersion ion implantation (PIII)," *Corrosion Science*, 2005, 47:1211-1225.

Baurschmidt et al., "The Electrochemical Aspects of the Thrombogenicity of a Material," *J. Bioengineering*, 1977, 1:261-278.

Bolz et al., "Effect of smooth, porous and fractal surface structure on the properties of an interface," *J. Materials Science: Materials in Medicine*, 1995, 6:844-848.

Brandau et al., "Nanoporous Ceramic Coatings for Synthesis of Radioactive Implants," *Journal of Nuclear Medicine Abstract Book*, Jun. 7, 2000, p. 244P, Abstract No. 1076.

Brückner et al., "Metal plasma immersion ion implantation and deposition (MPIIID): chromium on magnesium," *Surface and Coatings Technology*, 1998, 103-104, pp. 227-230.

Buescher et al., "Characterization of Wet-Chemically Nanostructured Stainless Steel Surfaces," *Mat. Res. Soc. Symp. Proc.*, 2001, 676:1-6.

Casan-Pastor et al., "Polyoxometalates: From Inorganic Chemistry to Materials Science," *Frontiers in Bioscience*, 2004, 9:1759-1770.

Chaieb et al , "Inhibition of the corrosion of steel in 1 M HC1 by eugenol derivatives," *Applied Surface Science*, 2005, 246:199-206.

Changwen et al., "Polyoxometalate-based organic-inorganic hybrid materials"; http://www.solgel.com/articles/oct01/changwen.asp, Retrieved from the Internet on Nov. 1, 2004 (17 pages).

Clemente-Leon et al., "Hybrid Langmuir-Blodgett Films Formed by Alternating Layers of Magnetic Polyoxometalate Clusters and Organic Donor Molecules—Towards the Preparation of Multifunctional Molecular Materials," *Adv. Mater.*, 2001, 13:574-577.

International Search Report/Written Opinion in PCT/US05/16600 mailed May 4, 2006, 15 pages.

International Preliminary Report on Patentability in PCT/US05/16600 mailed Nov. 30, 2006, 7 pages.

International Preliminary Report on Patentability in PCT/US07/78476 mailed Mar. 26, 2009, 7 pages.

Authorized Officer Simin Baharlou, International Preliminary Report on Patentability in PCT/US07/66568 mailed Oct. 23, 2008, 10 pages.

International Search Report/Written Opinion in PCT/US07/78505 mailed Mar. 4, 2008, 10 pages.

International Preliminary Report on Patentability in PCT/US07/78505 mailed Mar. 26, 2009, 7 pages.

Authorized Officer Athina Nickitas-Etienne, International Search Report/Written Opinion in PCT/US07/78449, mailed Jan. 13, 2009, 24 pages.

Authorized Officer Athina Nickitas-Etienne, International Preliminary Report on Patentability in PCT/US07/78449 mailed Mar. 26, 2009, 9 pages.

Authorized Officer Simin Baharlou, International Search Report/Written Opinion in PCT/US07/75072 mailed Jan. 25, 2008, 21 pages.

Authorized Officer Simin Baharlou, International Preliminary Report on Patentability in PCT/US07/75072 mailed Feb. 12, 2009, 9 pages.

International Search Report/Written Opinion in PCT/US07/78429 mailed Mar. 28, 2008, 13 pages.

International Preliminary Report on Patentability in PCT/US07/78429 mailed Apr. 2, 2009, 8 pages.

International Search Report/Written Opinion in PCT/US07/78411 mailed Mar. 6, 2008, 12 pages.

International Preliminary Report on Patentability in PCT/US07/78411 mailed Feb. 4, 2009, 8 pages.

Authorized Officer Elisabeth Reinecke, International Search Report/Written Opinion in PCT/US07/60137 mailed Jul. 27, 2007, 20 pages.

International Preliminary Report on Patentability in PCT/US07/78412 mailed Apr. 2, 2009, 7 pages.

Authorized Officer Trudy Hinterwimmer, International Search Report/Written Opinion in PCT/US07/78412 mailed Mar. 3, 2008, 10 pages.

Authorized Officer Joëlle Gerber, International Search Report/Written Opinion in PCT/US07/78450 mailed Nov. 19, 2008, 17 pages.
International Preliminary Report on Patentability in PCT/US07/78450 mailed Mar. 26, 2009, 7 pages.
International Search Report/Written Opinion in PCT/US07/73839 mailed Apr. 16, 2008, 17 pages.
International Preliminary Report on Patentability in PCT/US07/73839 mailed Apr. 2, 2009, 10 pages.
Authorized Officer Cecilia Giel-Barragán Ramos, International Search Report/Written Opinion in PCT/US07/79841 mailed Feb. 4, 2009, 21 pages.
Authorized Officer Athina Nickitas-Etienne, International Preliminary Report on Patentability in PCT/US07/79841 mailed Apr. 30, 2009, 7 pages.
Authorized Officer Joëlle Gerber, International Search Report/Written Opinion in PCT/US07/88888 mailed Jul. 13, 2009, 24 pages.
Authorized Officer Nora Lindner, International Preliminary Report on Patentability in PCT/US07/88888 mailed Jul. 30, 2009, 11 pages.
Authorized Officer Véronique van Loon-Mégard, International Search Report/Written Opinion in PCT/US08/75976 mailed Nov. 25, 2008, 20 pages.
Authorized Officer Trudy Hinterwimmer, International Search Report/Written Opinion in PCT/US09/49422 mailed Aug. 24, 2009, 10 pages.
Damiani et al., "Vasorelaxant effects on eugenol on rat thoracic aorta," *Vascular Pharmacol.*, 2003, 40:59-66.
Dexter, "Galvanic Corrosion," MAS Note, University of Delaware Sea Grant Marine Advisory Service, 2003.
Di Mario et al., "Moonlight: a controlled registry of an iridium-oxide coated stent with angiographic follow up," *Int. J. Cardiol.*, 2004, 95:329-331.
Dowling et al., "Anti-bacterial silver coatings exhibiting enhanced activity through the addition of Platinum," *Surf. & Coatings Tech.*, 2003, 163-164:637-640.
Eniola and Hammer, "Characterization of biodegradable drug delivery vehicles with the adhesive properties of leukocytes II: effect of degradation on targeting activity," *Biomaterials*, 2005, 26:661-670.
Ferrando, "Review of Corrosion and Corrosion Control of Magnesium Alloys and Composites," *J. Mater. Eng.*, 1989, 11:299-313.
Fischer et al., "Hydrogen in magnesium alloys and magnesium interfaces: preparation, electronic properties and interdiffusion," *J. Less Common Metals*, 1991, 172:808-815.
Fontenier et al., "Study of a 'Platinum-Magnesium' Cell to Supply Current to a Pacemaker," *Bioelectrochemistry and Bioenergetics*, 1975, 2(2):106-123.
Frei, "On the Role of Vitamin C and Other Antioxidants in Atherogenesis and Vascular Dysfunction," *Proceedings—Society for Experimental Biology and Medicine*, 1999, 222:196-204.
Gomes et al., "Alternative tissue engineering scaffolds based on starch: processing methodologies, morphology, degradation and mechanical properties," *Materials Science and Engineering C*, 2002, 20:19-26.
Grassi et al., "Short-term administration of dark chocolate is followed by a significant increase in insulin sensitivity and a decrease in blood pressure in healthy persons," *Am. J. Clin. Nutr.*, 2005, 81(3):611-614.
Gray and Luan, "Protective coatings on magnesium and its alloys—a critical review," *J. Alloys Compounds*, 2002, 336:88-113.
Guo et al., "Multi-layer LB films of single-wall carbon nanotubes," *Physica B*, 2002, 323:235-236.
Guo et al., "Manipulation of single-wall carbon nanotubes into aligned molecular layers," *Chem. Phys. Lett.*, 2002, 362:314-318.
Gurib-Fakim, "Medicinal plants: Traditions of yesterday and drugs of tomorrow," *Molecular Aspects of Medicine*, 2006, 27:1-93.
Haferkamp et al., "Magnesium-Base-Alloys as Implant-Material Steps to the Production of Thin Components," *Magnesium*, 2000, 159-164.
Huang et al., "A Review on Polymer Nanofibers by Electro-spinning and their Applications in Nanocomposites," *Composites Science & Technology*, 2003, 63:2223-2253.
Heublein et al., "Biocorrosion of magnesium alloys: a new principle in cardiovascular implant technology?" *Heart*, 2003, 89:651-656.

Heublein et al., "Bio-corrosion—a new principle for temporary cardiovascular implants?" *European Heart Journal, Journal of the European Society of Cardiology*, 2000, vol. 21, p. 286, Abstract No. P1605.
Heublein et al., "Degradation of Metallic Alloys—A New Principle in Stent Technology?" *The American Journal of Cardiology, Eleventh Annual Symposium Transcatheter Cardiovascular Therapeutics Abstracts*, Sep. 22, 1999.
Heublein et al., "Local Tissue Engineering by Biocorrosion Vision or Reality?" *The American Journal of Cardiology, TCT Abstracts/Poster*, Oct. 16, 2000.
Ito et al., "Antioxidant action of eugenol compounds; role of metal ion in the inhibition of lipid peroxidation," *Food Chem. Toxicol.*, 2005, 43:461-466.
Ivanova and Ivanov, "Mechanisms of the extracellular antioxidant defend," *Experimental Pathology and Parasitology*, 2000, 4:49-59.
Jiang, "A review of wet impregnation—An alternative method for the fabrication of high performance and nano-structured electrodes of solid oxide fuel cells," *Materials Science and Engineering A*, 2006, 418:199-210.
Kean and Davies, "Cathodic Protection," 7 pages, 1981; http://www.npl.co.uk/upload/pdf/cathodic_protection.pdf.
Kim et al., "Comprehensive study on vitamin C equivalent antioxidant capacity (VCEAC) of various polyphenols in scavenging a free radical and its structural relationship," *Crit. Rev. Food Sci. Nutr.*, 2004, 44(4):253-273.
Kim et al., "Effect of Anti-Oxidant (Carvedilol and Probucol) Loaded Stents in a Porcine Coronary Restenosis Model," *Circ. J.*, 2005, 69:101-106.
Kumar et al., "Polyanhydrides: an overview," *Advanced Drug Delivery Reviews*, 2002, 54:889-910.
Kurth et al., "Ultrathin Composite Films Incorporating the Nanoporous Isopolyoxomolybdate 'Keplerate' $(NH_4)_{42}[Mo_{132}O_{372}(CH_3COO)_{30}(H_2O)_{72}]$," *Chem. Mater.*, 2000, 12:2829-2831.
Kutsenko et al., "Structural Changes in Mg Alloy induced by plasma immersion ion implantation of Ag," *Acta Materialia*, 2004, 52:4329-4335.
Lambert et al., "Inhibition of carcinogenesis by polyphenols: evidence from laboratory investigations," *Am. J. Clin. Nutr.*, 2005, 81:284S-291S.
Lee et al., "Retentive and compressive strengths of modified zinc oxide-eugenol cements," *J. Dentistry*, 2000, 28:69-75.
Liao et al., "Fabrication of porous biodegradable polymer scaffolds using a solvent merging/particulate leaching method," *J. Biomed. Mater. Res.*, 2002, 59(4):676-681.
Lin et al., "Micropatterning proteins and cells on polylactic acid and poly(lactide-co-glycolide)," *Biomaterials*, 2005, 26:3655-3662.
Liu et al., "Sol-gel deposited TiO2 film on NiTi surgical alloy for biocompatibility improvement," *Thin Solid Films*, 2003, 429:225-230.
Liu, *Introduction to Corrosion and Protection*, Corrosion and Protection Centre, School of Materials, The University of Manchester, 2006, 36 pages.
Liu et al., "Layer-By-Layer Ionic Self-Assembly of Au Colloids Into Multilayer Thin-Films with Bulk Metal Conductivity," *Chemical Physics Letters*, 1998, 298:315-319.
Maier et al., "High concentrations of magnesium modulate vascular endothelial cell behaviour in vitro," *Biochim. Biophys. Acta*, 2004, 1689:6-12.
Mamedov et al., "Molecular Design of Strong Single-Wall Carbon Nanotube/Polyelectrolyte Multilayer Composites," *Nature Materials*, 2002, 1:190-194.
Medical Device Daily, "Conor Cites Positive 12-month Results for Its CoStar Stent", May 2005 (1 page).
Middleton and Tipton, "Synthetic Biodegradable Polymers as Medical Devices," http://www.devicelink.com/mpb/archive/98/03/002.html, Mar. 1998, 9 pages.
Mihailovic et al., "Unusual Magnetic State in Lithium-Doped $MoS_2$ Nanotubes," *Phys. Rev. Lett.*, 2003, 90 146401-1-4.
Mikos and Temenoff, "Formation of highly porous biodegradable scaffolds for tissue engineering," *Electronic Journal of Biotechnology*, 2000, 3(2):1-6.

Mohanty et al., "Effect of *Curcuma longa* and *Ocimum sanctum* on myocardial apoptosis in experimentally induced myocardial ischemic-reperfusion injury," *BMC Complementary and Alternative Medicine*, 2006, 6:3-14.

Mohanty et al. "Evaluation of soft tissue response to a poly[urethane urea]," *Biomaterials*, 1992, 13(10):651-656.

Molnar and Garai, "Plant-derived anti-inflammatory compounds affect MIF tautomerase activity," *International Immunopharmacology*, 2005, 5:849-856.

Moskaug et al., "Polyphenols and glutathione synthesis regulation," *Am. J. Clin. Nutr.*, 2005, 81:277S-283S.

Naderi et al., "Effect of some volatile oils on the affinity of intact and oxidized low-density lipoproteins for adrenal cell surface receptors," *Mol. Cell. Biochem.*, 2004, 267:59-66.

Niemeyer et al., "Magnesium alloys as biodegradable metallic implant materials for cardiovascularic and orthopaedic surgery," *Euromat 2001, 7th European Conference on Advanced Materials and Processes*, Jun. 10-14, 2001 (Abstract).

Nilsson et al., "Development of a dosage method for electrochemical treatment of tumours: a simplified mathematical model," *Bioelectrochemistry and Bioenergetics*, 1998, 47:11-18.

Ou et al., "Protective effects of eugenol against oxidized LDL-induced cytotoxicity and adhesion molecule expression in endothelial cells," *Food Chem. Toxicol.*, 2006, 44:1485-1495.

Park et al., "Microstructural change and precipitation hardening in melt-spun Mg-X-Ca alloys," *Science and Technology of Advanced Materials*, 2001, 2:73-78.

Peuster et al., "Long-term biocompatibility of a corrodible peripheral iron stent in the porcine of descending aorta," *Biomaterials*, 2006, 27:4955-4962.

Peuster et al., "A novel approach to temporary stenting: degradable cardiovascular stents produced from corrodible metal-results 6-18 months after implantation into New Zealand white rabbits," *Heart*, 2001, 86(5).

Prasse et al., "Electric Anisotropy of Carbon Nanofibre/Epoxy Resin Composites Due to Electric Field Induced Alignment," *Composites Science and Technology*, 2003, 63:1835-1841.

Ratnam et al., "Role of antioxidants in prophylaxis and therapy: A pharmaceutical perspective," *J. Controlled Release*, 2006, 113:189-207.

Remskar et al., "Self-Assembly of Subnanometer-Diameter Single-Wall $MoS_2$ Nanotubes," *Science*, 2001, 292:479-481.

Rezwan et al., "Biodegradable and bio active porous polymer/inorganic composite scaffolds for bone tissue engineering," *Biomaterials*, 2006, 27:3413-3431.

Rhule et al., "Polyoxometalates in Medicine," *Chem. Rev.*, 1998, 98:327-357.

Ryan et al., "Fabrication methods of porous metals for use in orthopaedic applications," *Biomaterials*, 2006, 27:2651-2670.

Sastry et al., "DNA-Mediated Electrostatic Assembly of Gold Nanoparticles into Linear Arrays by a Simple Drop-Coating Procedure," *Appl. Phys. Lett.*, 2001, 78:2943-2945.

Satoh et al., "Effect of Antioxidants on Radical Intensity and Cytotoxic Activity of Eugenol," *Anticancer Res.*, 1998, 18:1549-1552.

Sawitowski et al., "Nanoporous Alumina Coatings for Medical Implants and Stents—Radiotherapy, Drug Delivery, Biological Compatibility," *Materials Research Society Symposium Proceedings*, 1999, 581:523-528.

Sawitowski, "New Drug Delivery Systems—Examples of Applied Nanotechnology," *VDE World Microtechnologies Congress*, Sep. 25-27, 2000, Expo 2000, Hannover, Germany, Proveeds vol. 1, p. 343-346.

Sawyer et al., "Electrochemical Criteria in the Choice of Materials used in Vascular Prostheses," *Biophysical Mechanisms in Vascular Homeostasis and Intravascular Thrombosis*, 1965, pp. 337-348.

Schetky, "Shape Memory Alloys," *Encyclopedia of Chemical Technology* (3rd ed.), 1962, John Wiley & Sons, 20:726.

Shaw, "Corrosion Resistance of Magnesium Alloys," *ASM Handbook vol. 13A: Corrosion: Fundamentals, Testing, and Protection*, 2003, 5 pages.

Shi et al., "A novel electrically conductive and biodegradable composite made of polypyrrole nanoparticles and polylactide," *Biomaterials*, 2004, 25:2477-2488.

Singh et al., "Electrocatalytic Activity of Electrodeposited Composite Films of Polypyrrole and $CoFe_2O_4$ Nanoparticles Towards Oxygen Reduction Reaction," *Electrochimica Acta*, 2004, 49:4605-4612.

Song et al., "Galvanic corrosion of magnesium alloy AZ91D in contact with an aluminium alloy, steel and zinc," *Corrosion Science*, 2004, 46:955-977.

Stoclet et al., "Vascular protection by dietary polyphenols," *Eur. J. Pharmacol.*, 2004, 500:299-313.

Straumal et al., "Vacuum arc deposition of protective layers on glass and polymer," *Thin Solid Films*, 2001, 383:224-226.

Suhaj, "Spice antioxidants isolation and their antiradical activity: a review," *J. Food Composition and Analysis*, 2006, 19:531-537.

Suslick et al., "The Photochemistry of Chromium, Manganese, and Iron Porphyrin Complexes," *J. Chem.*, 1992, 16:633-642.

Tada et al., "Distribution of pH during galvanic corrosion of a Zn/steel couple," *Electrochimica Acta*, 2004, 49:1019-1026.

Tian et al., "Corrosion resistance improvement of magnesium alloy using nitrogen plasma ion implantation," *Surface & Coatings Technology*, 2005, 198:454-458.

von Euler et al., "Cell proliferation and apoptosis in rat mammary cancer after electrochemical treatment (EChT)," *Bioelectrochemistry*, 2004, 62:57-65.

Vrbanic et al., "Air-Stable Monodispersed $Mo_6S_3I_6$ Nanowires," *Nanotechnology*, 2004, 15:635-638.

Wallerath et al., "A blend of polyphenols explains the stimulatory effect of red wine on human endothelial NO synthase," *Nitric Oxide*, 2005, 12(2):97-104.

Wan et al., "Influence of Plasma Immersion Ion Implantation on Corrosion Properties of Magnesium," South Jiaotong University, Chengdu, 2005.

Wang et al., "Nonlinear optical properties of thin iron films grown on MgO (100) by pulsed laser deposition," *Thin Solid Films*, 2005, 471:86-90.

Wang et al., "Characterisation of Severely Deformed Austenitic Stainless Steel Wire," *Materials Science and Technology*, 2005, 21:1323-1328.

Wang, "Recent development of non-platinum catalysts for oxygen reduction reaction," *J. Power Sources*, 2005, 152:1-15.

Weber et al., "Hardness and corrosion resistance of single-phase nitride and carbide on ion," *Materials Science and Engineering*, 1995, 99:205-210.

Weh et al., "Evolution of afractal-like surface structures in layers of polyacrylonitrile solutions by interfacial dynamic processes," *J. Colloid and Interface Science*, 2004, 271:407-415.

Widmer et al., "Manufacture of porous biodegradable polymer conduits by an extrusion process for guided tissue regeneration," *Biomaterials*, 1998, 19:1945-1955.

Wieneke et al., "Stent Coating: A New Approach in Interventional Cardiology," *Herz*, 2002, 27(6):518-526.

Williamson et al., "Bioavailability and bioefficacy of polyphenols in humans. II. Review of 93 intervention studies," *Am. J. Clin. Nutr.*, 2005, 81:243S-255S.

Witte et al., "In vitro and in vivo corrosion measurements of magnesium alloys," *Biomaterials*, 2006, 27:1013-1018.

Yamaguchi et al., "Mg2Si Coating Technology on Magnesium Alloys to Improve Corrosion and Wear Resistance", *JOM*, 2004, p. 343.

Yi et al., "Characterization of a bioactive nanotextured surface created by controlled chemical oxidation of titanium," *Surface Science*, 2006, 600:4613-4621.

You et al., "The Effect of Calcium Additions on the Oxidation Behavior in Magnesium Alloys," *Scripta Mat.*, 2000, 42:1089-1094.

Yu and Uan, "Sacrificial Mg film anode for cathodic protection of die cast Mg-9-wt.%-1 wt.%Zn alloy in NaCl aqueous solution," *Scripta Mat.*, 2006, 54:1253-1257.

Yue et al., "Improvement in the Corrosion Resistance of Magnesium ZK60/SiC Composite by Excimer Laser Surface Treatment," *Scripta Materialia*, 1998, 38(2):191-198.

Zeta Potential—An Introduction in 30 Minutes, Technical Note; http://www.nbtc.cornell.edu/facilities/downloads/Zeta%20potential%20-

%20An%20introduction%20in%2030%20minutes.pdf, Retrieved from the Internet on May 9, 2005 (6 pages).

Zhou et al., "Drug-loaded, Magnetic, hollow silica nanocomposites for nanomedicine," *Nanomedicine: Nanotechnology, Biology and Medicine*, 2005, 1:233-237.

Zucchi et al., "Influence of a silane treatment on the corrosion resistance of a WE43 magnesium alloy," *Surface Coatings Technol.*, 2006, 200:4136-4143.

International Search Report for PCT/US2007/066568 dated Oct. 8, 2007.

Aaltonen, "Atomic Layer Deposition of Noble Metal Thin Films," *University of Helsinki*, Apr. 8, 2005, pp. 1-71.

Albion Research Notes, Newsletter, Oct. 1994, 3(4): 1-4.

Anand et al., "Ion-exchange resins: carrying drug delivery forward," *DDT*, 2001, 6: 905-914.

Anderson et al., "A new conductive polymer as a replacement for chrome conversion coatings," *2003 Aerospace Coatings Removel and Coatings Conference*, May 20-22, 2003, Colorado Springs, CO, 7 pages.

Ashtari et al. "An efficient method for recovery of target ssDNA based on amino-modified silica-coated magnetic nanoparticles" *Talanta 67*. (2005). 548-554.

Atta, "Electrochemical synthesis, characterization and some properties of a polymer derived from thioflavin S.," *European Polymer Journal*, 2005, 41: 3018-3025.

Australian Government, Department of Health and Aging, "Horizon Scanning Technology Prioritising Summary-Biodegradable stents for coronary artery disease," *Australia and New Zealand Horizon Scanning Network (ANZHSN)*, Aug. 2007, pp. 1-13.

Authorized officer Athina Nickitas-Etienne, International Preliminary Report on Patentability in PCT/US08/86639 mailed Jun. 24, 2010, 2 pages.

International Search Report/Written Opinion in PCT/US2008/86639 mailed Feb. 23, 2010, 8 pages.

International Search Report/Written Opinion in PCT/US2009/43326 mailed Aug. 6, 2009, 9 pages.

Babapulle and Eisenberg, "Coatred stents for their prevention of restenosis: Part II," *Circulation*, 2021, 106: 2849-2866.

Balasubramanian et al. "Dispersion and Stability Studies of Resorcinarene-Encapsulated Gold Nanoparticles." *Langmuir*, 2002, 1676-3681.

Bao, Y. et al. "Preparation of functionalized and gold-coated cobalt nanocrystals for biomedical applications." *Journal of Magnetism and Magnetic Materials*, 2005, 293:15-19.

Bekesi et al., "Efficient Submircon Processing of Metals with Femto," *Appl. Phys. A.*, Published Oct. 25, 2002, pp. 355-357.

Ben-Hamu et al., "Influence of Si, Ca and Ag addition on corrosion behaviour of new wrought Mg-Zn alloys," *Materials Science and Technology*, 2006, vol. 22, No. 10, pp. 1213-1218.

Bereket et al., "Electrochemical synthesis and anti-corrosive properties of polyaniline, poly(2-anisidine), and poly(aniline-co-2-anisidine) films on stainless steel," *Progress in Organic Coatings*, 2005, 54: 63-72.

Bernkop-Schnurch, "Chitosan and its derivatives: potential excipients for peroral peptide delivery systems," *International J. of Pharmaceutics*, 2000, 194: 1-13.

Biercuk et al., "Low-temperature atomic-layer-deposition lift-off method for microelectronic and nanoelectronic applications," *Applied Physics Letters*, vol. 83, No. 12, Sep. 22, 2003, pp. 2405-2407.

Blanusa et al., "Chelators as Antidotes of Metal Toxicity Therapeutic and Experimental Aspects," *Current Medicinal Chemistry*, 2005, vol. 12, pp. 2771-2794.

Bosiers et al., "Absorbable Metal stent for CLI in Infrapopliteal lesions: 1 year results," *CX 2005 Global Endovascular Forum*, Apr. 2005, pp. 1-23.

Brunatto and Muzart, "Influence of the gas mixture flow on the processing parameters of hollow cathode discharge ion sintering," *J. Phys. D.: Appl. Phys.*, 2007, 40: 3937-3944.

Brunner et al., "Porosity Tailored Growth of Black Anodic Layers on Magnesium in an Organic Electrolyte," Journal of the Electrochemical Society, vol. 156 (2), Dec. 12, 2008, pp. C62-C66.

Chang et al., "Effect of Heat Treatment on Corrosion and Electrochemical behavior of Mg-3Nd-0.2Zn-0.4Zr (wt. %) alloy," *Science Direct, Electrochimica Acta 52*, 2007, 3160-3167.

Chang et al., "Templated sythesis of Gold-iron Alloy nanoparticles using pulsed laser deposition," *Nanotechnology*, vol. 17, 2006, pp. 5131-5135.

Chen et al., "Laser Cladding of Mg20A18o Powder on ZM5 Magnesium Alloy," *Corrosion Engineering, Science and Technology*, 2007, vol. 42, No. 2, pp. 130-136.

Cheng et al., "Electrogeneration and electrochemical properties of hybrid materials: polypyrrole doped with polyoxometalates $PW_{12-x}Mo_xO_{40}^{3-}(x=0,3,6,12)$," *Synthetic Metals*, 2002, 129: 53-59.

Cho et al., "Gold-coated iron nanoparticles: a novel magnetic resonance agent for $T_1$ and $T_2$ weighted imaging," *Nanotechnology*, vol. 17, 2006, pp. 640-644.

Chou et al., "Electrochemical treatment of mouse and rat fibrosarcomas with direct current," *Bioelectromagnetics*, 1997, 18:14-24.

Cogger et al. "An Introduction to Electrochemical Impedance Measurement," *Solartron Analytical*, 1999, 2-14.

Conolly et al., "X-Ray microtomography studies of localized corrosion and transitions to stress corrosion cracking," *Materials Science and Technology*, 2006, vol. 22, No. 9, pp. 1076-1085.

Costa et al., "The effect of the magnetic field on the corrosion behavior of Nd-Fe-B permanent magnets." *Journal of Magnetism and Magnetic Materials*, 278, 2004, pp. 348-358.

Damen et al., "Paclitaxel esters of malic acid as prodrugs with improved water solubility," *Bioorganic & Medicinal Chemistry*, 2000, 8: 427-432.

Davies, "Changing the salt, changing the drug," *The Pharmaceutical Journal*, 2001, 266: 322-323.

De Geest et al., "Self-rupturing Microcapsules," *Adv. Mater.*, 2005, vol. 17, pp. 2357-2361.

de Witte, "Analysis of the principal component of external casing corrosion in deep wells," *J. Appl. Electrochem.*, 1985, 15: 325-334.

Di Mario et al., "Drug-eluting bioabsorbable magnesium stent," *J. Interventional Cardiol.*, 2004, 17(6): 391-395.

Duncan et al., "Polymer-drug conjugates, PDEPY and PELT: basic principles for design and transfer from the laboratory to clinic," *Journal of Controlled Release*, 2001, 74: 135-146.

Duncan, "The dawning era of polymer therapeutics," *Nature Reviews/Drug Discovery*, 2003, 2: 347-360.

Eggebrecht et al., "Novel Magnetic Resonance-Compatible Coronary Stent: The Absorbable Magnesium-Alloy Stent," *Circulation*, 2005, 112: 303-304.

Erbel et al., "Absorbierbare Stents-Eine Vielversprechende Neuerung?" *Urban & Vogel*, No. 4, 2007, pp. 308-319.

Erbel et al., "Temporary scaffolding of coronary arteries with bioabsorbable magnesium stents: a prospective, non-randomised multicentre trial," *Lancet*, 2007, vol. 369, pp. 1869-1875.

Erne et al., "The Road to Bioabsorbable Stents: Reaching Clinical Reality?" *Cardio Vascular and Interventional Radiology*, Sep. 26, 2005, pp. 11-16.

International Preliminary report on Patentability received in PCT/US2007/078417, mailed Mar. 26, 2009, 8 pages.

International Preliminary Report on Patentability, received in PCT/US2007/078407, mailed Mar. 26, 2009, 6 pages.

European Search Report from EP 10159664.1, mailed Jun. 4, 2010, 3 pages.

Falotico, "Cordis Fully Bioabsorbable Stent Program," *Euro PCR09*, May 22, 2009, pp. 1-21.

Fan et al., "Influence of Lanthanum on the microstructure, mechanical property and corrosion resistance of magnesium alloy," *J. Mater Sci*, 2006, vol. 41, pp. 5409-5416.

Fan et al., "Metallic Stents Coated with Bioabsorable Polymers," *Cardiac Interventions Today*, Jun./Jul. 2009, pp. 42-49.

Feng et al., "Sonochemical preparation of photochromic nanocomposite thin film based on polyoxometalates well dispersed in polyacrylamide," *Journal of Solid State Chemistry*, 2002, 169: 1-5.

Feng et al., "Superplasticity and texture of SiC whiskers in a magnesium-based composite," *Scripta Materialia*, 2005, 53: 361-365.

Ferguson et al., "Corrosion—Fatigue Performance of Magnesium Alloys," *International Journal of Modern Physics B*, vol. 17, Nos. 8 & 9, 2003, pp. 1601-1607.

Fischer et al., "Determination of in-vivo corrosion rates of degradable implants by SR-microtomography," date unknown, pp. 1-2.

Franhofer Institut Fertigungstechnik Material forschung, Evaluation of metal injection moulding (MIM) and extrusion as processing technology for biodegradable stents (A 208143), 8 pages.

Franhofer Institut Fertigungstechnik Material forschung, "Phase 2: Evaluation of mictoextrusion," 4 pages.

Fraunhofer EZRT, "Quantitative material analysis by dual energy computed tomography for industrial NDT applications," 2009, 1 pg.

Fraunhofer IIS—Poster (German), "Prinzip der hochauflösenden Comptuertomographie," 2009, 1 page.

Gabrielli, Claude. "Use and Applications of Electrochemical Impedance Techniques," *Solartron Analytical*, 1997, 1-102.

Garner et al., "Polypyrrole-heparin composites as stimulus-responsive substrates for endothelial cell growth," *J. Biomed. Mater. Res.*, 1999, 44: 121-129.

Gettleman et al., "Measurement of in vivo corrosion rates in baboons, and correlation with in vitro tests," Journal of Dental Research, 1980, 59: 689-707.

Gettleman et al., "Materials Science: Measurement of in vivo Corrosion Rates in Baboons, and Correlation with in vitro Tests," *Journal of Dental Research*, 1980, vol. 59, pp. 689-707.

Griffiths et al., "Future devices: bioabsorbable stents," *Br. J. Cardiol. (Acute & Interventional Cardiology)*, 2004, 11: AIC80-AIC84.

Grube, "Bioabsorbable Stents—The Boston Scientific & REVA Technology," *EuroPCR 2009*, 2009, pp. 1-27.

Gu et al., "In vitro Corrosion and biocompatibility of binary magnesium alloys," *Biomaterials*, vol. 30, 2009, pp. 484-498.

Gupta et al., "Nanometer spaced electrodes using selective area atomic layer deposition," *Applied Physics Letters*, vol. 90, 2007, pp. 1-4.

Haenzi et al., "Design strategy for microalloyed ultra-ductile Mg alloys," 2009, *Phil. Mag. Letters*, 89(6): 377-390.

Haenzi et al., "Design strategy for new biodegradable Mg-Y-Zn alloys for medical applications," *Int. J. Mat. Res.*, 2009, 100: 1127-1136.

Haenzi et al., "On the biodegradation performance of an Mg-Y-RE alloy with various surface conditions in simulated body fluid," *Acta Biomat.*, 2009, 5: 162-171.

Hamu et al., "Influence of Si, Ca and Ag addition on corrosion behavior of new wrought Mg-Zn alloys," 2006, 22(10): 1213-1218.

Hänzi et al., "Design strategy for microalloyed ultra-ductile magnesium alloys," *Philosophical Magazine letters*, vol. 89, No. 6, Jun. 2009, pp. 377-390.

Hänzi et al., "Design strategy for new biodegradable Mg-Y-Zn alloys for medical applications," *Int. J. Mat. Res.*, vol. 100, 2009, pp. 1127-1136.

Hänzi et al., "On the biodegradation performance of an Mg-Y-Re alloy with various surface conditions in simulated body fluid," *Acta Biomaterialia*, vol. 5, 2009, pp. 162-171.

Haque et al. "Bioabsorption Qualities of Chitosan-absorbable Vascular Templates," *Current Surgery*, 2001, 58(1): 77-80.

Heismann et al., "Density and atomic number measurements with spectral x-ray attenuation method," *Journal of Applied Physics*, vol. 94, No. 3, Aug. 1, 2003, pp. 2073-2079.

Hermawan et al., "Developments in metallic biodegradable stents," *Acta Biomaterialia*, 2010, 6: 1693-1697.

Hermawan et al., "Degradable metallic biomaterials: Design and development of Fe-Mn alloys for stents," *Wiley InterScience: Article*, Apr. 19, 2008, pp. 1-12.

Hermawan et al., "Degradation Behaviour of Metallic Biomaterials for Degradable Stents," *Advanced Materials Research*, 2007, 15-17:113-118.

Hermawan et al., "Development of Degradable Fe-35Mn Alloy for Biomedical Application," *Advanced Material Research*, 2007, 15-17:107-112.

Hermawan et al., "Fe-Mn Alloys for Metallic Biodegradable Stents: Degradation and Cell Viability Studies," *Acta Biomaterialia*, Manuscript, Mar. 27, 2009, pp. 1-30.

Hermawan, et al., "Iron-Manganese: new class of metallic degradable biomaterials prepared by powder metallurgy," *Powder Metallurgy*, 2008, 51(1):38-45.

Hildebrandt et al., "Prevention of surface encrustation of urological implants by coating with inhibitors," *Biomaterials*, 2001, 22:503-507.

Holclajtner-Antunovic et al., "Study of some polyoxometallates of Keggin's type as potention antitumour agents," *Jugoslov Med. Biohem.*, 2004, 23: 25-30.

Hourng et al., Influence of multisteps thermal control in metal powder injection moulding process, *Powder Metallurgy*, 2008, 51: 84-89.

Hutten, A. et al. "Ferromagnetic FeCo nanoparticles for biotechnology". (2005) *Journal of Magnetism and Magnetic Materials* 293:93-101).

Iakovou et al., "Incidence, Predictors, and Outcome of Thrombosis Successful Implantation of Drug-Eluting Stents," *JAMA*, 2005, 293(17): 2126-2130.

Ignat et al., "Magnesium alloys (WE43 and ZE41) characterization for laser applications," *Applied Surface Science*, 2004, 233:382-391.

Iida et al. "Surface modification of of $\lambda Fe_2O_3$ nanoparticles with aminopropylsilyl groups and interparticle linkage with with a,w-Dicarboxylic Acids". *Electrochimica Acta*. 2005. 855-859.

Imgrund, "Evaluation of metal injection moulding (MIM) and extrusion as processing technology for biodegradable stents. A 208143: Final report for phase I MIM of Fe and Fe-Si powders and sample characterisation," Aug. 15, 2008, *Fraunhofer Institut Fertigungstechnik Material forschung*, 18 pages.

Integran, "Biodegradable Nanometallic Intracoronary Stents," May 12, 2009, 1 page.

Integran, "Biodegradable Nanometallic Intracoronary Stents," Proposal, May 12, 2009, 1 page.

International Preliminary Report on Patentability received in PCT/US2007/078479, mailed Mar. 26, 2009, 8 pages.

International Search Report / Written Opinion in PCT/US09/046750 mailed Jul. 20, 2010, 14 pages.

International Search Report and Written Opinion received in PCT/US2007/078417, mailed Jan. 22, 2009, 18 pages.

International Search Report and Written Opinion received in PCT/US2007/078479, mailed Dec. 30, 2008, 12 pages.

International Search Report from PCT/US 03/20215, mailed Nov. 11, 2003, 4 pages.

International Search Report/Written Opinion in PCT/US2007/078407, mailed Mar. 26, 2008, 10 pages.

Jabara et al., "Bioabsorbable Stents: The Future is Near," *Cardiac Interventions Today*, Jun./Jul. 2009, pp. 50-53.

Jabara, "Poly-anhydride based on salicylic acid and adipic acid anhydride," Glimpse into the future: bioabsorbable stents-aimint to restore vascular integrity, *Euro PCR09*, 2009, pp. 1-34.

James A. Plambeck, "Electrolytic Processes of Nonmetals," *Chemical Sciences*, 1995, 2 pages.

Jiang et al., "Corrosion protection of polypyrrole electrodeposited on AZ91 magnesium alloys in alkaline solutions," *Synthetic Materials*, 2003, 139: 335-339.

Jiang et al., "Effect of $TiB_2$ particulate on partial remelting behavior of Mg-11Al-0.5Zn matrix composite," *Materials Science and Engineering A*, 2004, 381: 223-229.

Kaesel et al., "Approach to Control the Corrosion of Magnesium by Alloying," *Magnesium: Proceedings of the 6th International Conference Magnesium Alloys and Their Applications*, 2004, pp. 534-539.

Kainer, "Magnesium alloys and technology," Wiley VCH, 2003, 119 pages.

Kaya et al., "Microstructure and Corrosion Resistance of Alloys of the Mg-Zn-Ag System," *Metal Science and Heat Treatment*, 2006, 48(11-12): 524-530.

Kececioglu, "Zur Biokompatibilitat eines neu entwickelten Stentmaterials aus korrodierbarem Reineisen," Jan. 25, 2007, pp. 1-131, *Ruhr-Universitat-Bochum*.

Kidambi et al., "Selective depositions on polyelectrolyte multilayers: self-assembled monolayers of m-dPEG acid as molecular template," *J. Am. Chem. Soc.*, 2004, 126: 4697-4703.

Kokubo et al., "How useful is SBF in predicting in vivo bone bioactivity?" *Biomaterials*, 2006, 27: 2907-2915.

LaFont, "Arterial Remodeling Technologies: Bioresorbable Stents," *Euro PCR09*, 2009, pp. 1-28.

Lee, J. et al. "Simple synthesis of mesoporous carbon with magnetic nano particles embedded in carbon rods". (2005) Carbon 43:2536-2543.

Lee, Sang-Yup et al. "Surface modification of magnetic nanoparticles capped by oleic acids: Characterization and colloidal stability in polar solvents" *Journal of Colloid and Interface Science* 293 (2006) 401-408.

Levesque et al., "Design of pseudo-physiological test bench specific to the development of biodegradable metallic biomaterials," *Acta Biomaterialia*, 2008, 4:284-295.

Li et al., "Effects of Direct Current on Dog Liver: Possible Mechanisms for Tumor Electrochemical Treatment," *Bioelectromagnetics*, 1997, 18:2-7.

Li et al., "Photoacoustic Tomography and Sensing in Biomedicine," *Phys. Med. Biol.*, 2009, 54:59-97.

Li, "Poly(L-glutamic acid)-anticancer drug conjugates," *Advanced Drug Delivery Reviews*, 2002, 54: 695-713.

Liu et al., "Characterizations of polypyrrole (PPy) nano-tubules made by templated ac electropolymerization," *European Polymer Journal*, 2005, 41: 2117-2121.

Lu et al. "Magnetic Switch of Permeability for Polyelectrolyte Microcapsules Embedded with Co@Au Nanoparticles". *American Chemical Society*. 2004.

Lu et al., "Theoretical analysis of calcium phosphate precipitation in simulated body fluid," *Biomaterials*, 2005, 26:1097-1108.

Maeng et al., "Negative Vascular Remodelling after Implantation of Bioabsorbable Magnesium Alloy Stents in Porcine Coronary Arteries: A randomized Comparison with Bare-Metal and Sirolimus-Eluting Stents," *Heart*, 2009, 95:241-246.

Maendl, "Zerstaubungsabscheidung von Mg-Legierungen," *Leibniz-Institutt fur Oberflachenmodifizierung*, 2001, pp. 1-17.

Mani et al., "Coronary Stents: A materials perspective," *Biomaterials*, 2007, 28:1689-1710.

Mansfeld, Florian. "Analysis and Interpretation of EIS Data for Metals and Alloys," *Solartron Analytical*, 1999, 1-77.

Marijan et al. "Surface Modification of Stainless Steel-304 Electrode. 2. An Experimental Comparative Study of Electrochemically, Hydrothermally and Chemically Modified Oxide Films." *CCACAA*, 1999, 72(4) 751-761.

Markman, "Absorbable Coronary stents," *The Lancet*, Jun. 2, 2007, 369:1839-1840.

Massaro et al., "Comparative Investigation of the surface properties of commercial titanium dental implants. Part 1: chemical composition," *Journal of Materials Science; Materials in Medicine*, vol. 13, 2002, pp. 535-548.

Meng Han, "Laser nitriding of metals: Influences of the ambient pressure and the pulse duration," 2001, Dissertation, Georg-August-Universität Göttingen, 134 pages.

*Methods in Cell Biology (Cell Death)*, vol. 46, p. 163.

Miao et al., "Porous Calcium Phosphate Ceramics prepared by coating polyurethane foams with Calcium phosphate cements," *Materials Letters*, vol. 58, 2004, pp. 397-402.

Mueller et al., "Control of smooth muscle cell proliferation by ferrous iron," *Biomaterials*, vol. 27, 2006, pp. 2193-2200.

Mueller et al., "Magnesium and its Alloys as Degradable Biomaterials, Corrosion Studies Using Potentiodynamic and EIS Electrochemical Tenchiques," *Materials Research*, 2007, 10(1): 5-10.

Mueller et al., "Preparation of SBF with different $HCO_3$ content and its influence on the composition of biomimetic apatites," *Acta Biomaterialia*, 2006, 2:181-189.

Munoz et al., "Interactive Effects of Albumin and Phosphate Ions on the Corrosion of CoCrMo Implant Alloy," *Journal of the Electrochemical Society*, 2007, 154(10):562-570.

Nachtrab et al., "Quantitative Material Analysis by Dual-Energy Computed Tomography for Industrial NDT Applications," *Fraunhofer EZRT*, date unknown, 1 page.

Nair and Laurencin, "Biodegradable polymers as biomaterials," *Prog. Polym. Sci.*, 2007, 32: 762-798.

Nguyen et al., "Mechanism for protection of iron corrosion by an intrinsically electronic conducting polymer," *Journal of Electroanalytical Chemistry*, 2004, 572: 225-234.

Ni et al., "Cellular localization of antiviral polyoxometalates in J774 macrophages," *Antiviral Research*, 1995, 32: 141-148.

Niinisto, "Atomic Layer deposition: A key technology for the controlled growth of oxide thin films for advanced applications," *Proc. Estonian Acad. Sci. Phys. Math.*, 2003, 52(3):266-276.

Ogata et al., "A novel anti-tumor agent, polyoxomolybdate induces apoptotic cell death in AsPC-1 human pancreatic cancer cells," *Biomedicine & Pharmacotherapy*, 2005, 59: 240-244.

Onuma et al., "Everolimus-eluting bioabsorbable stent," *Euro PCR09*, May 22, 2009, pp. 1-28.

Ormiston et al., "Bioabsorbable Coronary Stents," *Circulation Cardiovasc Intervent*, vol. 2, 2009, pp. 255-260.

Ouerd et al., "Reactivity of Titanium in Physiolgoical Medium—I. Electrochemical Characterization of the Metal/Protein Interface," *Journal of the Electrochemical Society*, vol. 154, No. 10, 2007, pp. 593-601.

Oyane et al., "Preparation and assessment of revised simulated body fluids," *Wiley Periodicals, Inc.*, 2003, pp. 188-195.

Paliwoda-Porebska et al., "On the development of polypyrrole coatings with self-healing properties for iron corrosion protection," *Corrosion Science*, 2005, 47: 3216-3233.

Peeters et al., "Preliminary Results after Application of Absorbable Metal Stents in Patients with Critical Limb Ischemia," *J. Endovasc Ther*, 2005, 12:1-5.

Peeters, et al., "Preliminary Data on Absorbable Metal Stents," *MEET 2006*, Jun. 2006, pp. 1-30.

Peuster et al., "Are resorbable implants about to become a reality," *Cardiol Young*, 2006, 16:107-116.

Pinto Slattow et al., "Optical coherence tomography and intravascular ultrasound imaging of bioabsorbable magnesium stent degradation in porcine coronary arteries," *Cardiovascular Revascularization Medicine 9*, (2008) pp. 248-254.

Purushothaman et al. "Reducing Mass-Transport Limitations by Application of Special Pulsed Current Modes". *Journal of the Electrochemical Society*. 152 (4), 2005, J33-J39.

Qasem et al., "Kinetics of paclitaxel 2'-N-methylpyridinium mesylate decomposition," *AAPS PharmSciTech*, 2003, 4(2), Article 21, 8 pages.

Quinard et al., "Development of metal/polymer mixtures for micro powder injection moulding," *10th ESAFORM Conference on Material Forming*, 2007, pp. 933-939.

Qureshi et al., "The emerging role of iron, zinc, copper, magnesium and selenium and oxidative stress in health and diseases," *Biogenic Amines*, vol. 19, No. 2, 2005, pp. 147-169.

Raman et al., "Laser assisted modification of surface microstructure for localised corrosion resistance of magnesium alloys," *Surface Engineering*, 2007, 23(2): 107-111.

Reece et al., "Metal transport studies on inherently conducting polymer membrances containing cyclodextrin dopants," *Journal of Membrane Science*, 2005, 249: 9-20.

Ren et al., "Variations of dose and electrode spacing for rat breast cancer electrochemical treatment," *Bioelectromagnetics*, 2001, 22(3):205-211.

Rettig et al., "Composition of corrosion layers on a magnesium rare-earth alloy in simulated body fluids," *Journal of Biomedical Materials Research Part A*, Oct. 18, 2006, pp. 359-369.

Rettig et al., "Corrosion resistance studies on grain-boundary etched drug-eluting stents," *J. Mater Sci: Mater Med.*, 2007, vol. 18, pp. 1377-1387.

Rettig et al., "Time-dependent electrochemical characterization of the corrosion of a magnesium rare-earth alloy in simulated body fluids," *Journal of Biomedical Materials Research Part A*, 2007, 167-175.

Rinkevich et al., "Regeneration of Amputated Avian Bone by a Coral Skeletal Implant," *Biol. Bull.*, vol. 197, Aug. 1999, pp. 11-13.

Rivers et al., "Synthesis of a novel, biodegradable electrically conducting polymer for biomedical applications," *Advanced Functional Materials*, 2002, 12: 33-37.

Russell-Stevens et al., "The effect of thermal cycling on the properties of a carbon fibre reinforced magnesium composite," *Materials Science and Engineering A*, 2005, 397: 249-256.

Schauer et al., "Protection of iron against corrosion with polyaniline primers," *Progress in Organic Coatings*, 1998, 33: 20-27.

Schinhammer et al., "Design strategy for biodegradable Fe-based alloys for medical applications," *Acta Biomaterialia*, 2009, pp. 1-9.

Schmidt et al., "Physiochemical changes in London clay adjacent to cast iron pipes," *IAEG 2006, The Geological Society of London*, Paper 313, 12 pages.

Schneider et al., "From functional core/shell nanoparticles prepared via layer-by-layer deposition to empty nanospheres," *Nano Letters*, 2004, 4: 1833-1839.

Schranz et al., "Bioabsorbable Metal Stents for Percutaneous Treatment of Critical Recoarctation of the Aorta in a Newborn," *Catheterization and Cardiovascular Interventions*, vol. 67, 2006, pp. 671-673.

Secheresse et al., "$(Mo_2O_2X_2)^{2+}$ (X=O,S), a magic building block for the design of wheel shaped metalates," *C.R. Chimie*, 2005, 8: 1927-1938.

Serruys et al., "A bioabsorbable everolimus-eluting coronary stent system (ABSORB): 2-year outcomes and results from multiple imaging methods," *The Lancet*, 2009, 373: 897-910.

Serruys, "Fourth Annual American College of Cardiology International Lecture," *Journal of the American College of Cardiology*, 2006, vol. 47, No. 9, pp. 1754-1768.

Serruys, "Glimpse into the future: bioabsorbable stents-aiming to restore vascular integrity—Introduction & Objectives," *Euro PCR09*, May 18, 2009, pp. 1-4.

Shevchenk et al., "Porous Surface of NiTi Alloy Produced by Plasma Ion Implantation," *Institute of Ion Beam Physics and Materials Research*, 2005, Strasbourg, 1 page.

Shevchenko, "Structure, composition and mechanical properties of porous layers produced by argon PIII," *Forschungszentrum Dresden*, Oct. 2007, 8 pages.

Shieh et al. "Aqueous dispersions of magnetite nanoparticles with NH3 surfaces for magnetic manipulations of biomolecules and MRI contrast agents" *Biomaterials*, 2005 26: 7183-7191.

Sieber, et al., "Investigations on the passivity of iron in borate and phosphate buffers, pH 8.4," *Corrosion Science*, vol. 48, 2006, pp. 3472-3488.

Singh Raman et al., "Laser assisted modification of surface microstructure for localised corrosion resistance of magnesium alloys," *Surface Engineering*, 2007, 23(2):107-111.

Smith et al. "Patterning self-assembled monolayers" *Progress in Surface Science*. 2004. 75:1-68.

Soto et al., "Amporphous magnesium nitride films produced by reactive pulsed lasar deposition," Journal of Non-Crystalline Solids, 2004, 342: 65-69.

Stoner et al., "The mechanism of low frequency a.c. Electrochemical Disinfection," *Bioelectrochemistry and Bioenergetics*, 1982, 9:229-243.

Su et al., "Photoacoustic imaging of coronary artery stents," *Optics Express*, vol. 17, No. 22, Oct. 26, 2009, pp. 1-8.

Sun et al., "Fabrication of a multilayer film electrode containing porphyrin and its application as a potentiometric sensor of iodide ion," *Talanta*, 1998, 46: 15-21.

Truong et al., "Corrosion protection of magnesium by electroactive polypyrrole/paint coatings," *Synthetic Metals*, 2000, 110: 7-15.

Turler et al., "Experimental low-level direct current therapy in liver metastases: influence of polarity and current dose," *Bioelectromagnetics*, 2000, 21(5):395-401.

Uhlmann et al., "Schnelle 3D-Analyse von Gefugemerkmalen" *Druckguss*, Apr. 2009, pp. 1-5.

Van Alst, "Potential conflicts of interest," *Euro PCR09*, 2009, pp. 1-22.

Virtanen et al., "Electrochemical Behavior of Fe in Phosphate Solutions Studied by In Situ X-Ray Absorption Near Edge Structure," *Journal of the Electrochemical Society*, vol. 146, No. 11, 1999, pp. 4087-4094.

Virtanen et al., "Special modes of corrosion under physiological and simulated physiological conditions," *Acta Biomaterialia*, vol. 4, 2008, pp. 468-476.

Virtanen, "Corrosion of Biomedical Implant Materials," *Corrosion of Biomedical Implant Materials*, vol. 26, Nos. 2-3, 2008, pp. 147-171.

Volkova, "Effect of Deformation and Heat Treatment on the Structure and Properties of Magnesium Alloys of the Mg-Zn-Zr System," *Metal Science and Heat Treatment*, vol. 48, Nos. 11-12, 2006, pp. 508-512.

Volynova et al., "Mechanical Properties and the Fine Structure of Powdered Iron-Manganese Alloys," *Plenum Publishing Corp.*, 1987, pp. 999-1006.

Waksman et al., "Early- and Long-Term Intravascular Ultrasound and Angiographic Findings After Bioabsorbable Magnesium Stent Implantation in Human Coronary Arteries," *JACC: Cardiovascular Interventions*, vol. 2, No. 4, 2009, pp. 1-9.

Waksman et al., "Safety and Efficacy of Bioabsorbable Magnesium Alloy Stents in Procine Coronary Arteries," *Catherterization and Cardiovascular Intervnetions*, 2006, vol. 68, pp. 607-617.

Waksman et al., "Short-term Effects of Biocorrodible Iron Stents in Porcine Coronary Arteries," *Journal of Interventional Cardiology*, vol. 21, No. 1, 2008, pp. 15-20.

Waksman, "Update on Bioabsorbable Stents: From Bench to Clinical," *Journal of Interventional Cardiology*, vol. 19, No. 5, 2006, pp. 414-421.

Waksman, Ron, "Current state of the metallic bioabsorbable stent," Glimpse to the Future, *Euro PCR09*, 2009, pp. 1-24.

Waksman, Ron, "Why Bioabsorbale Stent Technology," Glimpse to the Future, *Euro PCR09*, 2009, pp. 1-16.

Wan et al., "Preparation and characterization of porous conducting poly(DL-lactide) composite membranes," *Journal of Membrane Science*, 2005, 246: 193-201.

Wang et al., "Polyaniline microrods synthesized by a polyoxometalates/poly(vinyl alcohol) microfibers template," *Materials Letters*, 2005, 59: 3982-3985.

Weiss et al., "Pyrrole derivatives for electrochemical coating of metallic medical devices," J. Polymer Science, Part A: Polymer Chemistry, 2004, 42: 1658-1667.

Weiss et al., "Pyrrole derivatives for electrochemical coating of metallic medical devices," *J. Polymer Science, Part A: Polymer Chemistry*, 2004, 42: 1658-1667.

White and Slade, "Polymer electrodes doped with heteropolymetallates and their use within solid-state supercapacitors," *Synthetic Metals*, 2003, 139: 123-131.

Wilcox, "Biodegradable Technology: Medtronic Biodegradable Stent Program," *Euro PCR09*, 2009, pp. 1-25.

Windecker et al., "Biolimus-eluting stent with biodegradable polymer versus sirolimus-eluting stent with durable polymer for coronary revascularisations (LEADRERS): a randomized non-inferiority trial," *The Lancet*, Sep. 1, 2008, pp. 1-11.

Witte et al., "Biodegradable magnesium-hydroxyapatite metal matrix composites," *Biomaterials*, vol. 28, 2007, pp. 2163-2174.

Witte et al., "In Vivo Corrosion of Four Magnesium Alloys and the Associated Bone Response," *Biomaterials*, vol. 26, 2005, pp. 3557-3563.

Witte, "The history of biodegradable magnesium implants: A review," *Acta Biomaterialia*, 2010, 6: 1680-1692.

Witte, "Magnesium Corrosion: a New Challaenge for temporary Biomaterials," *Laboratory for Biomechanic and Biomaterials*, 2009, pp. 1-20.

Wuisman and Smit, "Bioresorbable polymers: heading for a new generation of spinal cages," *Eur. Spine J.*, 2006, 15: 133-148.

Xin et al., "Electrochemical Treatment of Lung Cancer," *Bioelectromagnetics*, 1997, 18:8-13.

Xu et al., "In Vivo corrosion behaviouc of Mg-MnZn alloy for bone implant application," *Journal of Biomedical Materials Research Part A*, Jun. 4, 2007, pp. 703-711.

Ye et al., "In situ synthesis of AlN particles in Mg-Al alloy by $Mg_3$-$N_2$ addition," *Materials Letters*, 2004, 58: 2361-2361.

Yen et al., "Electrochemical treatment of human KB cells in vitro," *Bioelectromagnetics*, 1999, 20:34-41.

Yfantis et al., "Novel corrosion-resistant films for Mg alloys," *Surface and Coatings Technology*, 2002, 151-152: 400-404.

Yuen et al., "Findings from an Accelerated in Vivo Corrosion Model of Magnesium," *Department of Orthopaedics and Traumatology*, date unknown, pp. 1-2.

Yun et al., "Revolutionizing Biodegradable Materials," *Materials Today*, Oct. 2009, vol. 12, No. 10, pp. 1-11.

Zarras et al., "Progress in using conductive polymers as corrosion-inhibiting coatings," *Radiation Physics and Chemistry*, 2003, 68: 387-394.

Zberg et al., "MgZnCa glasses without clinically observable hydrogen evolution for biodegradable implants," *Nature materials*, Sep. 27, 2009, vol. 8, pp. 887-891.

Zheng, "Symposium on Biodegradable/Biocorroded metallic materials," Nov. 24, 2009, pp. 1-74.

Zhu et al., "Biocompatibility of Fe-O films synthesized by plasma immersion ion implantation and deposition," *Surface and Coatings Technology*, vol. 203, 2009, pp. 1523-1529.

Zhu et al., "Biocompatibility of pure iron: In Vitro assessment of degradation kinetics and cytotoxicity on endothelial cells," *Materials Science and Engineering*, vol. 29, 2009, pp. 1589-1582.

Zou et al., "Preparation of a phosophopolyoxomolybdate $P_2Mo_{18}O^{6-}_{62}$ doped polypyrrole modified electrode and its catalytic properties," *Journal of Electroanalytical Chemistry*, 2004, 566: 63-71.

Zucchi et al., "Electrochemical behaviour of a magnesium alloy containing rare earth elements," *Journal of Applied Electrochemistry*, 2006, vol. 36, pp. 195-204.

International Search Report and Written Opinion from PCT/US09/043591, mailed Jun. 30, 2010, 10 pages.

International Search Report from PCT/US07/005671, mailed Jun. 2, 2008, 10 pages.

Ma et al., "Inhibition effect of self-assembled films formed by gold nanoparticles on iron surface," *Applied Surface Science*, 2006, 252: 4327-4334.

Li et al., "The corrosion inhibition of the self assembled Au, and Ag nanoparticles films on the surface of copper," *Colloids and Surfaces A: Physiochem. Eng. Aspects*, 2006, 273: 16-23.

International Preliminary Report on Patentability from PCT/US08/75976 dated Mar. 25, 2010, mailed Nov. 25, 2008, 8 pages.

Macias et al., "Electrospun mesoporous metal oxide fibers," *Microporous and Mesoporous Materials*, 2005, 86: 1-13.

Viswanathamurthi et al., "Preparation and morphology of niobuim oxide fibres by electrospinning," *Chemical Physics Letters*, 2003, 374: 79-84.

Authorized Officer Henrique Amaro, International Preliminary Report on Patentability from PCT/US09/043326 mailed Nov. 18, 2010, 7 pages.

Authorized Officer Jasmine Messemanne, International Search Report from PCT/US09/051965 mailed Aug. 20, 2010, 13 pages.

Authorized Officer Jasmine Messemanne, International Preliminary Report on Patentability from PCT/US09/051965 mailed Feb. 10, 2011, 8 pages.

Authorized Officer Antonio Espuch, International Preliminary Report on Patentability in PCT/US09/49422 mailed Jan. 13, 2011, 7 pages.

Authorized Officer Aurore Schneider, International Preliminary Report on Patentability from PCT/US2010/042772 mailed Feb. 4, 2011, 9 pages.

Authorized Officer Henrique Amaro, International Preliminary Report on Patentability in PCT/US2009/43326 mailed Nov. 18, 2010, 7 pages.

Authorized Officer Antoine Laurent, International Preliminary Report on Patentability in PCT/US09/046750 mailed Dec. 23, 2010, 8 pages.

Deepwater, "Galvanic Series," http://corrosion-doctors.org/definitions/galvanic-series.htm> on Mar. 11, 2011, 5 pages.

Wikipedia, the Free Encyclopedia, "Galvanic Corrosion." <http://en.wikipedia.org/wiki/Galvanic_corrosion> on Mar. 11, 2011, 7 pages.

Authorized Officer Mary Celine, International Search Report from PCT/US2010/060412 mailed Feb. 21, 2011, 10 pages.

Dumas et al., "Characterization of magnesium fluoride thin films produced by argon ion beam-assisted deposition," *Thin Solid Films*, 2001, pp. 61-68.

Authorized Officer Razik Menidjel, International Preliminary Report on Patentability from PCT/US09/059424, mailed May 5, 2011, 8 pages.

US 6,533,715, 03/2003, Hossainy et al. (withdrawn)

\* cited by examiner

US 8,048,150 B2

ENDOPROSTHESIS HAVING A FIBER MESHWORK DISPOSED THEREON

FIELD OF THE INVENTION

This invention relates to medical devices, such as endoprostheses, and methods of making such devices.

BACKGROUND

The body includes various passageways including blood vessels such as arteries, and other body lumens. These passageways sometimes become occluded or weakened. For example, they can be occluded by a tumor, restricted by plaque, or weakened by an aneurysm. When this occurs, the passageway can be reopened or reinforced, or even replaced, with a medical endoprosthesis. An endoprosthesis is an artificial implant that is typically placed in a passageway or lumen in the body. Many endoprostheses are tubular members, examples of which include stents, stent-grafts, and covered stents.

Many endoprostheses can be delivered inside the body by a catheter. Typically the catheter supports a reduced-size or compacted form of the endoprosthesis as it is transported to a desired site in the body, for example the site of weakening or occlusion in a body lumen. Upon reaching the desired site the endoprosthesis is installed so that it can contact the walls of the lumen.

One method of installation involves expanding the endoprosthesis. The expansion mechanism used to install the endoprosthesis may include forcing it to expand radially. For example, the expansion can be achieved with a catheter that carries a balloon in conjunction with a balloon-expandable endoprosthesis reduced in size relative to its final form in the body. The balloon is inflated to deform and/or expand the endoprosthesis in order to fix it at a predetermined position in contact with the lumen wall. The balloon can then be deflated, and the catheter withdrawn.

In another delivery technique, the endoprosthesis is formed of an elastic material that can be reversibly compacted and expanded (e.g., elastically or through a reversible phase transition of its constituent material). Before and during introduction into the body until it reaches the desired implantation site, the endoprosthesis is restrained in a compacted condition. Upon reaching the desired site, the restraint is removed, for example by retracting a restraining device such as an outer sheath, enabling the endoprosthesis to self-expand by its own internal elastic restoring force.

To support or keep a passageway open, endoprostheses are sometimes made of relatively strong materials, such as stainless steel or Nitinol (a nickel-titanium alloy), formed into struts or wires. The material from which an endoprosthesis is made can impact not only the way in which it is installed, but its lifetime and efficacy within the body.

SUMMARY

A medical device, comprising: an underlying structure having a fiber meshwork disposed thereon, wherein the underlying structure is biodisintegrable. The medical device can further comprise a layer-by-layer coating situated on the fiber meshwork.

A medical device for implantation into an organism, comprising: an underlying structure; and a fiber meshwork disposed upon the structure, wherein the fiber meshwork is configured to ensure steady biodisintegration of the underlying structure over a period of time inside the organism.

A medical device comprising a fiber meshwork formed of a material that is deposited by FFESS on to an underlying structure.

A method of effecting controlled release of a pharmaceutically active agent from a medical device, wherein the medical device is implanted in an organism, comprising: depositing a fiber meshwork containing a therapeutic agent on an underlying structure, wherein the fiber meshwork degrades over a period of time inside the organism and simultaneously releases the therapeutic agent.

A method of achieving steady disintegration of a medical device in an organism, comprising: forming the device by depositing a fiber meshwork on to an underlying structure; and implanting the device into the organism; wherein the disintegration of the underlying structure occurs over a first period of time inside the organism.

A method of making a medical device comprising depositing a fiber meshwork by FFESS on to an underlying structure.

A method of using a medical device that comprises an underlying structure having a fiber meshwork disposed thereon, wherein the underlying structure is Biodisintegrable, the method comprising implanting the medical device in a body passageway of an organism.

The various details of one or more embodiments of the invention are set forth in the accompanying drawings and the description hereinbelow. Other aspects, features, and advantages of the invention will be apparent from the description and drawings, and from the claims.

BRIEF DESCRIPTION OF THE DRAWINGS

Like reference symbols in the various drawings indicate like elements.

DETAILED DESCRIPTION

Figure 1A:
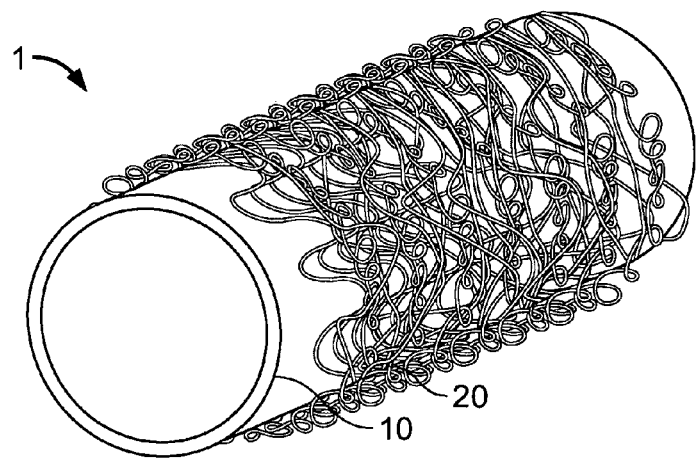
FIGS. 1A and 1B are respectively perspective and cross-sectional views of an exemplary endoprosthesis.

Although endoprostheses have been highly effective at removing restrictions in body passageways, a number of problems have emerged that arise from their long-term placement. Restenosis is one; another is that, over time, microbes and other material can build up on a structure such as a stent and cause their own obstruction to free passage of body fluids through the lumen. Restenosis has been addressed by coating a stent with a polymer containing a drug that inhibits growth of smooth muscle cells (see, e.g., "The Billion Dollar Stent," *Technology Review*, 108(10), 41, (October 2005)). Accumulations of unwanted material have been deterred by loading the device structure with an anti-microbial agent, but with limited success. Accordingly, there has been a move towards making endoprostheses out of bio-absorbable materials, such as magnesium or iron alloys and biodegradable polymers, that ensure that the device structure naturally degrades over time. Such materials may, however, disintegrate too quickly thus requiring them to be made out of thicker elements than would be preferred. On the other hand, the presence of a coating on the device, such as is typically used to achieve local delivery of a therapeutic agent at the implantation site, can hinder degradation of the underlying device structure. For example, with coating patterns that are based on a closed polymer matrix, the coating impedes fluid access to the device surface, thereby significantly delaying—or even preventing inception of—the desired degradation process. In many instances, it would be preferable to have the underlying structure disappear (or at least start to disappear) before the coating has disappeared. This would also ensure a much longer delivery regime of a therapeutic agent absorbed in the coating than the timeframe over which the device structure disappears.

On the other hand, polymer coatings that disappear in a very short timeframe, thereby offering the exposure of the underlying device structure required to bring about its degradation, have several attendant drawbacks. First, the rapid decay of the coating leads to a massive initial drug release. The consequent inability to control the process of polymer disintegration, also entails the risk of a highly variable drug release profile during the process. Slight variations in various environmental parameters such as temperature, fluid flow-rate, and local concentrations of critical agents, can cause a huge difference in the degradation course of different regions of exposed surface area. Finally, if the polymer coating disintegrates too rapidly, the device structure itself may also disintegrate in a non-uniform manner so that large particles loosen, break off and float into the bloodstream, causing boli and secondary blockages.

Accordingly, the devices herein address such issues by incorporating material that is strong enough to last longer than the underlying structure so as to prevent both its uncontrolled breakdown and non-uniform drug release, yet which is flexible enough to permit regulated access of bodily fluids to the underlying structure.

Definitions

A biocompatible material is a material that can be introduced into living tissue or a living system, and is non-toxic or non-injurious to the tissue or system, and does not cause an immunological reaction or rejection.

As used herein, a "biodisintegrable material" is a biocompatible material that undergoes at least one of dissolution, degradation, absorption, erosion, corrosion, resorption, chemical transformation, or other disintegration processes over the period that the device formed at least in part from the biodisintegrable material is designed to reside in an organism. Chemical transformation can include oxidation or other chemical reactions of the stent body material.

Specifically, a biodisintegrable material is a material that exhibits substantial mass or density reduction by one or more of dissolution, degradation, absorption, erosion, corrosion, resorption, decomposition, degeneration, chemical transformation and/or other disintegration processes after it is introduced into an organism. The disintegration occurs to a desirable extent in a timeframe that can provide a clinical benefit. Mass reduction of a biodisintegrable device can also occur, but in some cases does not occur, by fragmentation of the material. The disintegration can be the result of the chemical and biological interaction of the material with the physiological environment into which it is implanted and/or can be initiated by applying a suitable triggering influence, such as a chemical reactant or source of energy to the stent.

In some embodiments, a biodisintegrable material for use with the present invention exhibits substantial mass reduction after a period of time for which a function of the material, such as support of a lumen wall or delivery of a therapeutic agent in the immediate vicinity of the device, is no longer needed or desirable. By "a substantial reduction" is meant that the biodisintegrable material exhibits a mass reduction through biodisintegration of at least about 10%, at least about 20%, at least about 25%, at least about 30%, at least about 50%, at least about 75%, or at least about 90%, after a period of implantation. The period of implantation over which the mass reduction through biodisintegration takes place can be chosen to be one day or more, 14 days or more, 30 days or more, 60 days or more, 90 days or more, 180 days or more, 300 days or more, 600 days or more, or about 1,000 days or less. Thus, it would be understood that the level of biodisintegrability can be tailored to achieve a given level of mass reduction over a certain desired duration. For example, a medical device may be required to have reached a 75% reduction in mass in 30 days. In another embodiment, it may be required to have attained a 30% reduction in mass in 180 days. It would also be understood by one of ordinary skill in the art that a period of days, such as 300 days, as used herein, entails a level of imprecision such that periods of 3-5 days either shorter or longer than the period in question are also acceptable equivalent timescales for measuring levels of biodisintegrability.

In certain embodiments of the present invention, only portions of the device exhibit biodisintegrability. For example, an exterior layer or coating may be non-biodisintegrable, while an interior layer or body is biodisintegrable.

A degradable material is a material that can dissociate, depolymerize, or otherwise reduce in molecular weight from its starting molecular weight, such that a resulting compound is soluble in an aqueous medium such as water or, if insoluble, can be suspended in a body fluid and transported away from an implantation site without obstructing the flow of the body fluid. A biodegradable material is one that will degrade into biocompatible compounds as part of a biological process.

In some embodiments, a biodegradable material exhibits substantial mass reduction after a period of time for which a function of the material, such as support of a lumen wall or delivery of a therapeutic agent in the immediate vicinity of the device, is no longer needed or desirable. By "a substantial reduction" is meant that the biodegradable material exhibits a mass reduction through biodegradation of at least about 10%, at least about 20%, at least about 25%, at least about 30%, at least about 50%, at least about 75%, or at least about 90%, after a period of implantation. The period of implantation over which the mass reduction through biodegradation takes place can be chosen to be one day or more, 14 days or more, 30 days or more, 60 days or more, 90 days or more, 180 days or more, 300 days or more, 600 days or more, or about 1,000 days or less. Thus, it would be understood that the level of biodegradability can be tailored to achieve a given level of mass reduction over a certain desired duration. For example, a material may be required to have reached a 25% reduction in mass in 600 days. In another embodiment, it may be required to have attained a 30% reduction in mass in 300 days. It would also be understood by one of ordinary skill in the art that a period of days, such as 180 days, as used herein, entails a level of imprecision such that periods of 3-5 days either shorter or longer than the period in question are also acceptable equivalent timescales for measuring levels of biodegradability.

A resorbable material is a material that is soluble, biodisintegrable as defined herein, or is an aggregate of soluble and/or disintegrable material(s) with insoluble material(s) such that, with the resorption of the soluble and/or disintegrable materials, the residual insoluble materials are of sufficiently fine size that they can be suspended in a body fluid and transported away from the implantation site without obstructing the flow of the body fluid. Ultimately, the particles are eliminated from the body either by excretion in fluids such as perspiration, urine or feces, or are themselves dissolved, degraded, corroded or otherwise metabolized into soluble components that are then excreted from the body. A bioresorbable material is a resorbable material that is biocompatible.

The term "body fluid" as used herein refers to fluids in the body of an organism—especially a mammal—including, but not limited to, blood, urine, saliva, lymph, plasma, gastric, biliary, or intestinal fluids, seminal fluids, and mucosal fluids or humors.

The terms "therapeutic agent", "pharmaceutically active agent", "pharmaceutically active material", "pharmaceutically active ingredient", "drug" and other related terms may be used interchangeably herein and include, but are not limited to, small organic molecules, peptides, oligopeptides, proteins, nucleic acids, oligonucleotides, genetic therapeutic agents, non-genetic therapeutic agents, vectors for delivery of genetic therapeutic agents, cells, and therapeutic agents identified as candidates for vascular treatment regimens, for example, as agents targeting restenosis.

By small organic molecule is meant an organic molecule having 50 or fewer carbon atoms, and fewer than 100 non-hydrogen atoms in total.

As used herein, an "antimicrobial agent" is any agent that is harmful to microbes, especially pathogenic bacteria.

As used herein, "treatment" refers to the prevention of a disease or condition, the reduction or elimination of symptoms associated with a disease or condition, or the substantial or complete elimination of a disease or condition.

In certain embodiments, as further described herein, biostable materials, e.g., polyelectrolytes, may be utilized. As used herein, a "biostable material" is a material that does not undergo substantial dissolution, degradation, absorption, erosion, decomposition, corrosion, chemical transformation, resorption and/or other disintegration processes over the period that the material is designed to reside in an organism.

Overview

Figure 1B:
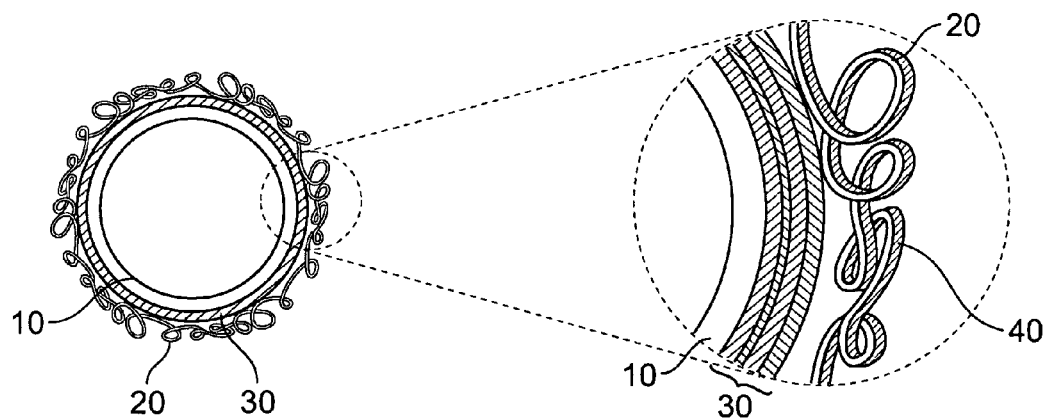

Medical devices having a fiber meshwork disposed upon an underlying structure such as a mechanical support, and methods of making the devices are disclosed. Two views of an exemplary device 1 are shown in FIGS. 1A and 1B, in which an underlying structure 10 is covered at least in part by a fiber meshwork 20 comprising one or more fibers (not individually depicted in FIGS. 1A or 1B) that may optionally contain or be coated with material containing at least one therapeutic agent such as a pharmaceutically active ingredient. Exemplary device 1 is generally tubular in shape and as depicted may be, e.g., a stent. As shown in the exploded view of FIG. 1B, the underlying structure 10 may optionally be coated by a multilayer structure 30, in one or more layers of which is optionally contained a therapeutic agent. The fiber or fibers of which the fiber meshwork 20 is composed may also optionally be coated with a multi-layer structure 40 as shown in FIG. 1B. Multilayer structure 40 may also optionally contain at least one therapeutic agent in one or more of its constituent layers.

In some embodiments, the underlying structure 10 is biodisintegrable and is made from a different material than is the fiber meshwork 20. For example, the underlying structure can include (e.g., be formed of) a biodisintegrable metal or a biodisintegrable polymer, as described in Bolz, U.S. Pat. No. 6,287,332; Heublein, U.S. Patent Application Publication No. 2002/0004060 A1; U.S. Pat. No. 5,587,507; and U.S. Pat. No. 6,475,477. The fiber meshwork can wrap around the underlying structure without totally encapsulating it, thereby permitting fluid access to it. The fiber meshwork can be of a sufficient strength to retain its shape for a longer time than that of the underlying structure itself. If the mechanical support is bio-disintegrable, it is thereby allowed to degrade in a controlled manner, while the fiber meshwork retains its structure.

Fiber meshwork 20 can be formed from a material impregnated with a therapeutic agent that releases such an agent slowly over time. Alternatively, the fiber meshwork 20 is overcoated with a multilayer structure. The multilayer structure can be a layer-by-layer (LBL) coating wherein one or more layers contain a therapeutic agent. The fiber meshwork is thus able to ensure both a controlled release of a therapeutic agent absorbed within it or coated over it, as well as a controlled degradation of the underlying structure. A still further advantage of deploying a fiber meshwork impregnated with a drug or coated with layers containing a drug is that, when used in conjunction with an endoprosthesis whose underlying structure itself has a lattice or mesh structure, or similar, it can provide a more uniform release profile of the drug in the region of the stent than, e.g., a coating directly deposited on such a lattice or mesh structure. The latter may tend to release higher concentration of drug along the struts of the endoprosthesis than in the gaps in between such struts.

In alternative embodiments, the underlying structure 10 is also covered with a multilayer structure such as a LBL coating.

In an alternative embodiment, the fiber meshwork acts as an enclosing envelope to regulate release of a therapeutic agent from loosely packed particulate materials situated within it.

The fiber meshwork can be created with electro-spun nano-fibers or micro-fibers, and by flow-limited field-injection electrostatic spraying (FFESS), as further described herein.

Fiber Meshwork

The fiber meshwork can be amorphous, i.e., does not possess a regular structure. Thus, the fiber meshwork contains one or more fibers. Each individual fiber can be considered to consist of a number of contiguous segments. Each fiber wraps around the underlying structure in such a manner that one of its segments crosses either another segment of the same fiber or another fiber at least once. In this way, the fiber meshwork is composed of a number of fiber segments that cross one another, when viewed from a given direction.

In some embodiments, the fiber meshwork comprises a single fiber. However, equally satisfactory fiber meshworks may be utilized that comprise more than one fiber. The fiber meshwork can utilize 10 or fewer fibers, such as 2, 3, 5, or 7 fibers. From 10 to about 100 fibers can also be used, for example, 20, 50, or 80 fibers are effective. In such embodiments, not all of the fibers need to be made of the same material. Each of such fibers may be as long as several millimeters, or may be as long as about 1 centimeter, or as long as about 5 centimeters, or as long as about 10 centimeters, and may even be as long as about 20 centimeters. Where more than one fiber is present, it is not necessary that every fiber have the same or a similar length. Thus it is possible that several fibers are used, all having lengths of between 5 and 7 mm. It is also possible that several fibers are used, having lengths of 5 mm, 2 cm, 5 cm, and 10 cm.

A fiber meshwork can also be constructed based on a very large number of short lengths of fibers. Such fibers may be as short as about 10 micron, or may be from about 10 to about 100 µ, but the overall meshwork may consist of many thousands, and may even consist of many hundreds of thousands of such fibers.

It is not required that the fiber meshwork itself envelop the entirety of the exterior surface of the underlying support. Alternatively, the fiber meshwork, when suitably rigid, can be manufactured to extend beyond the dimensions of the underlying structure, thereby permitting delivery of a therapeutic agent contained therein to regions of the body lumen outside of those supported by the underlying structure.

The nature of the fiber meshwork can be such that there are minute gaps between the various segments of fiber so that body fluids can contact the underlying structure. The fiber meshwork thus has an effective porosity that results from its structure in a manner different from that of other materials, for example a polymer matrix. Advantageously, the benefits of the fiber meshwork arise from a combination of its porosity and durability. Regarding porosity, defined as the proportion of the non-solid volume to the total volume of material, the fiber meshwork is able to attain a porosity higher than that of a polymer matrix of comparable volume. In some embodiments, the porosity of the fiber meshwork is in the range 0.1-0.6, and in other embodiments it is in the range 0.2-0.4. By contrast with a polymer matrix, however, the fiber meshwork is harder and less flexible, thereby retaining more of its structure as an underlying structure degrades.

The fiber meshwork can retain a therapeutic agent and allow for its release over time. The nature of the fiber meshwork is such that it has a large surface area and thus is capable of releasing uniformly a therapeutic agent absorbed within it or in a layer coated on top of it.

The fiber meshwork may comprise a polymeric material such as a polymer, or a blend of polymers. A "polymer" is any macromolecule composed of two or more monomers, and includes dimers, trimers, tetramers, etc. A "monomer" is a polymerizable molecule. Typically, the polymeric materials comprise polymer molecules having a median number of monomers that numbers in the tens (10 to 99), in the hundreds (100 to 999), in the thousands (1,000 to 9,999), or in the tens of thousands (10,000 to 99,999) as well as a mixture of polymers having different median numbers of monomers. The polymeric materials can comprise polymer molecules having a median number of monomers that is 100,000 or more.

Such polymers may be crosslinked or uncrosslinked, linear or branched, natural or synthetic, thermoplastic or thermosetting, and may be biostable, biodegradable, bioabsorbable, biodisintegrable, or dissolvable.

In some embodiments, the polymers used to form the fiber meshwork are biodegradable. For example, the polymers can substantially degrade over a period of time that is different from the period of time over which the underlying structure substantially biodisintegrates. In such embodiments, the polymers of the fiber meshwork biodegrade over a longer period of time than the period of time for which the underlying structure biodisintegrates. In other embodiments, the polymers are biostable.

Polymers for use in the fiber meshwork can include any polymer that is biocompatible, and in particular a polymer that is compatible with the specific implantation environment in instances where local conditions are unusually hostile to non-native materials. An exemplary polymer is poly(D,L-lactide-co-glycolide) ('PLG'). Other polymers are further described herein. Still other exemplary polymers include, but are not limited to: poly(lactic acid); poly(glycolic acid); poly (caprolactone); poly(hydroxybutyrate); poly(orthoester); poly(alkane anhydride); gelatin collagen; oxidized cellulose; and poly(phosphazene).

The fiber meshwork may also be constructed from other materials that are biodegradable, including metals. Accordingly, in certain embodiments the fiber meshwork is made from magnesium fibers. In other embodiments, the fiber meshwork is made from fibers of iron, or zinc. Additionally, fibers of metal alloys are contemplated.

Typically the fiber meshwork is coated onto the underlying support so that it forms from about 10% to about 50% by weight of the entire device. For example, the fiber meshwork forms about 20% to about 30% by weight of the entire device weight.

Figure 2A:
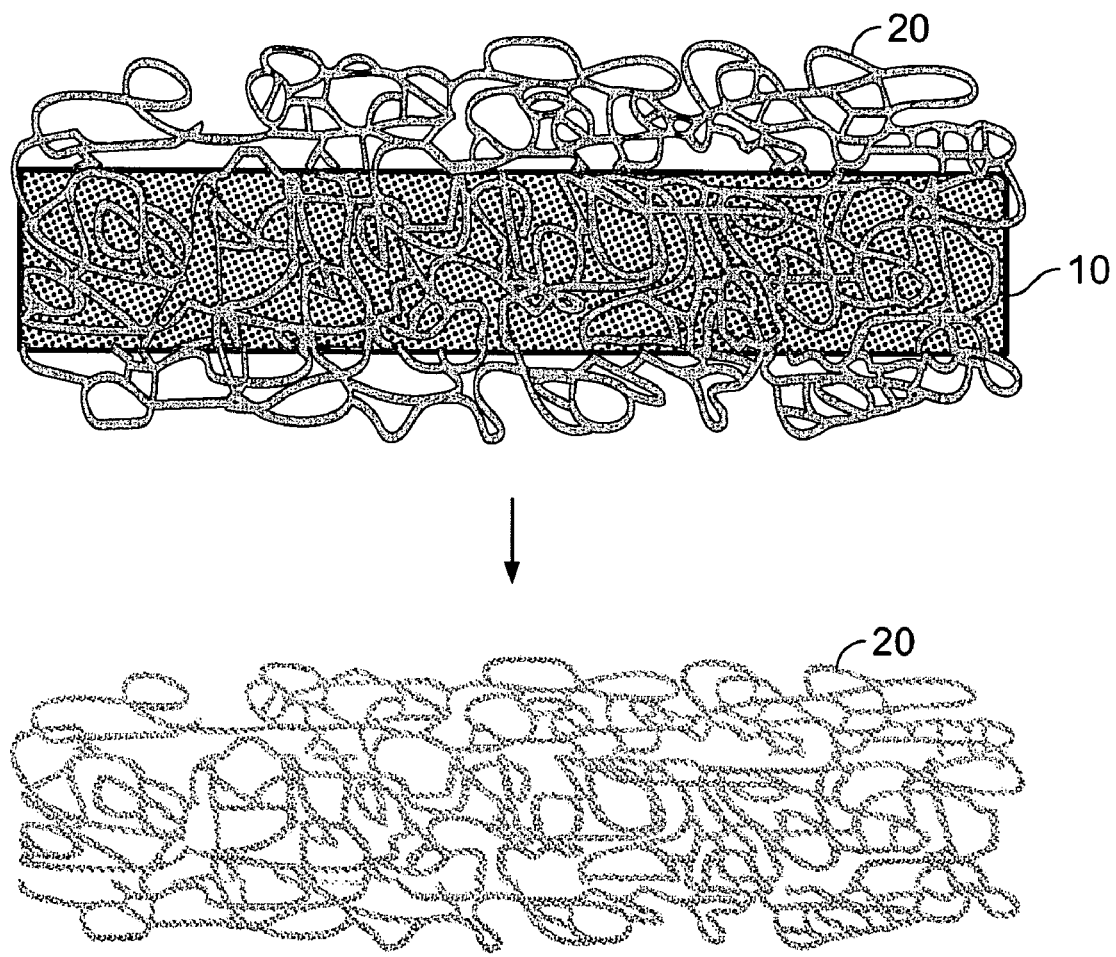
FIG. 2A shows how a biodisintegrable stent corrodes before a fiber meshwork disappears, giving a drug release beyond the lifetime of the mechanical support.

In certain embodiments, the polymers from which the fiber meshwork is formed lead to self-supporting fibers so that, as shown schematically in FIG. 2A, at such time as the underlying structure 10 has substantially biodisintegrated, the fiber meshwork 20 retains its original shape or a close approximation thereof. By so doing, the fiber meshwork does not collapse and obstruct free passage of bodily fluids through the lumen in which it is situated. Instead, the fiber meshwork retains a support structure that helps to maintain the structure of the lumen itself where previously the underlying structure of the endoprosthesis had provided support. It is also envisaged that, in certain environments, the fiber meshwork becomes embedded, either partially or completely, in layers of cells as may be found on the internal surface of a body passageway. In such an eventuality, the fiber meshwork is reinforced, even after the underlying structure has degraded, and has a reduced propensity to collapse. Furthermore, by retaining its original shape or a close approximation thereof, the fiber meshwork is able to continue release of a therapeutic agent contained within it, as further described herein. By the term "close approximation thereof" as used herein, it is understood that the fiber meshwork will naturally distort overtime but it is intended that it does so to only a small extent.

Figure 2B:
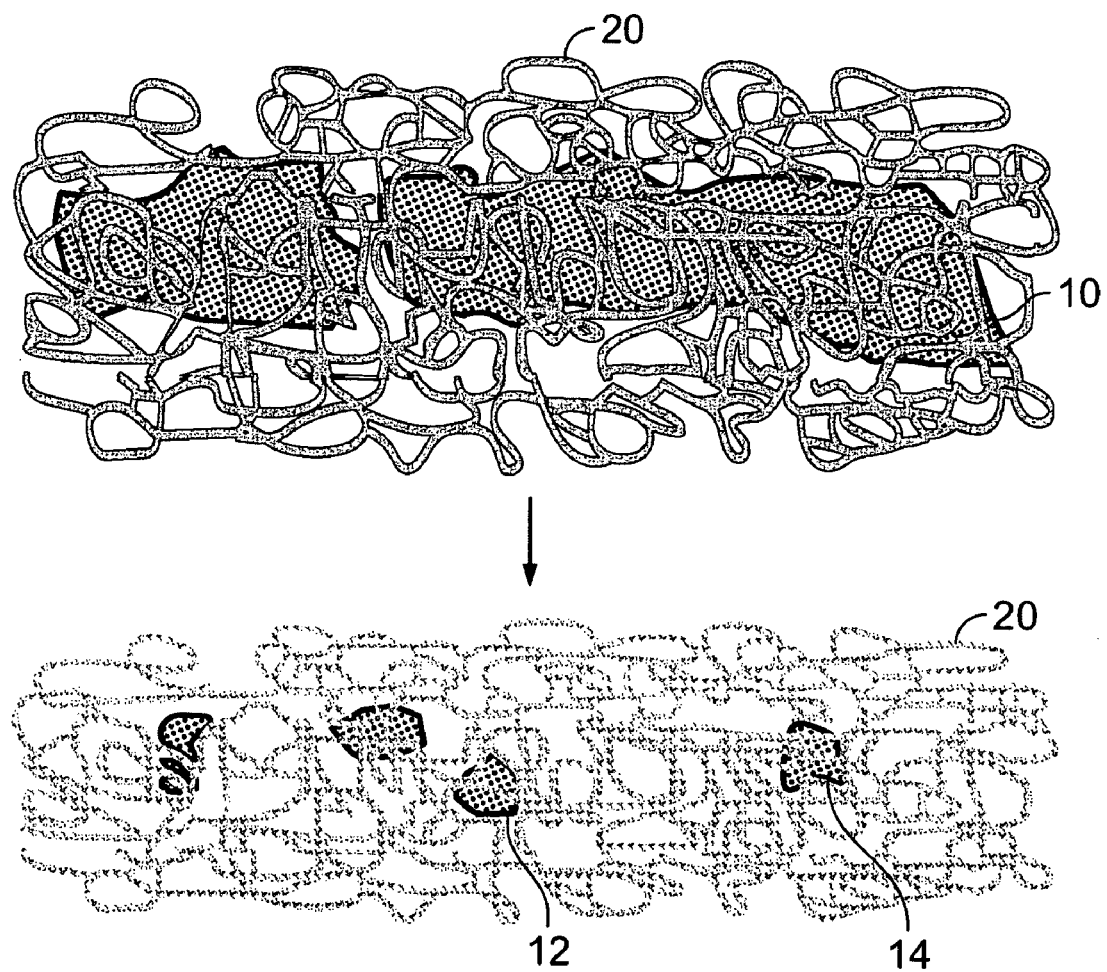
FIG. 2B shows how particles from a disintegrating mechanical support are captured by a fiber meshwork.

The structure of the fiber meshwork produced with a method such as FFESS is such that fluid access to the surface of the mechanical support is permitted. The fiber meshwork itself can be chosen to be biostable or very slowly degrading, to act as an enclosing envelope for the more rapidly disintegrating device structure, thereby addressing the problem of uneven device degradation, as shown in FIG. 2B for the example of a stent. Furthermore, as also shown in FIG. 2B, were an underlying structure 10 to disintegrate unevenly, to give large particles such as 12, 14, those particles may be captured by the fiber meshwork 20 before floating off into the body fluid. Biostable materials for forming the fiber meshwork include, for example, styrene-isobutylene-styrene ('SIBS'), silicone elastomers; poly(ethylene-co-vinyl acetate); and Polyacrylates.

In another embodiment, the underlying structure comprises a first ring and a second ring, wherein the first ring and the second ring are connected to one another by the fiber meshwork. In another variant of such an embodiment, the first ring is made of a first material and the second ring is made of a second material. In still another variant, the first material and the second material are different from a material of which the fiber meshwork is comprised. In an exemplary embodiment, the first and second ring are arranged coaxially to one another. It is to be expected, however, that due to flexibility of the fiber meshwork, the first and second ring may not be always situated exactly coaxially with respect to one another, and may also not always be disposed so that their respective planes are parallel to one another. For example, the centers of the respective rings may be offset with respect to one another and/or the planes of the rings may be disposed at an angle other than 180° with respect to one another. Such variations are to be expected within both manufacture and operation of the embodiment.

In such embodiments in which the underlying structure comprises two rings separated from one another, and connected to one another, by the fiber meshwork, the overall device has a flexibility imparted by the fiber meshwork and thus can, e.g., bend if necessary in a curved or flexible section of a body lumen. Such an embodiment has still further application in body lumens where the support function may be unnecessary, but delivery of a therapeutic agent, such as may be absorbed within the fibers of the fiber meshwork, is desired.

The fiber meshwork may also itself degrade in a controllable manner and therefore be used to fine-tune the disintegration of the underlying structure. As the fiber meshwork itself degrades, the biodisintegrable material of the underlying structure can become more exposed to water in the bodily fluids that surround it. This increased exposure to water can cause the underlying structure to begin to disintegrate, or to disintegrate more rapidly. Eventually, the underlying structure may disintegrate entirely.

Furthermore, the fiber meshwork can be comprised of polymers to which a surface charge can readily be attached, or which are naturally charged such that a multi-layer structure can be disposed thereon, using a layer-by-layer method that builds up layers of alternating charges, as further described herein.

FFESS

The fiber meshwork may be deposited by a number of methods of creating and depositing extremely thin fibers, known to one of ordinary skill in the art. Such methods are typically related to electrospraying. In essence, in electrospraying, an electric field is used to drive charged particles to a grounded substrate. A charged solution exits from a spray nozzle in a conical configuration, referred to as the Taylor cone. If the Taylor cone doesn't break up, the solution forms fibers; otherwise the material becomes individual spray droplets. The two principal parameters that control behavior of the Taylor cone are the viscosity and voltage at the nozzle. Exemplary methods of creating ultra-thin fibers for use in creating a fiber meshwork involve electro-spinning. Electro-spinning methods are described in Shin, Hohman, Brenner, and Rutledge, "Experimental Characterization of electrospinning: the electrically forced jet and instabilities", *Polymer* 42, 9955-9967, (2001), incorporated herein by reference in its entirety. Fibers that are micrometers in diameter can be created by melt spinning or gel spinning, i.e., they are formed out of a gel or a molten melt.

Figure 3:
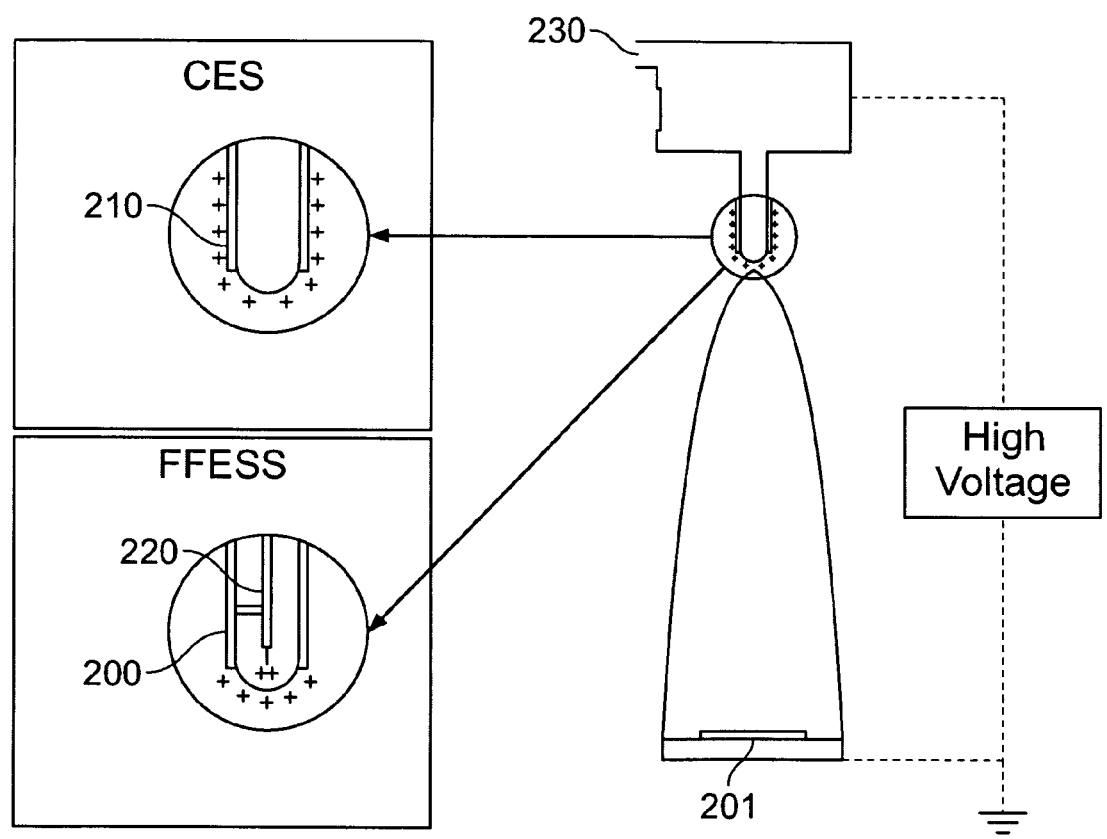
FIG. 3 is a schematic diagram comparing conventional electro-spraying and FFESS technology.

A particularly exemplary method of depositing the fiber meshwork, is to use a process referred to as flow-limited field-injection electrostatic spraying (FFESS). FFESS is a form of electrospraying which offers a very high degree of control over shape and flow regimes, and which allows spinning a fiber-meshwork on top of a medical device, such as an endoprosthesis, with a glass spray nozzle. The nozzle generates a charge at the liquid meniscus that enables successful electrospray. A schematic comparison of apparatuses used respectively for conventional electro-spraying and FFESS is shown in FIG. 3 in which a structure to be sprayed is denoted 201. The two principal differences are first that FFESS sprays a polymer/solvent solution 230 from a smooth glass capillary 200 whereas CES uses a metal hypodermic needle 210, and second that FFESS uses a sharpened tungsten needle 220 inside capillary 200, whereas CES has no analogous structure. The overall effect of the FFESS apparatus is to improve jet stability and uniformity of the polymer sprayed by FFESS relative to that from CES.

Using the FFESS method for electro-spinning creates a fiber meshwork in which the one or more fibers have a highly controlled fiber diameter. In particular, as would be understood by one of ordinary skill in the art, by controlling the voltage, flow-rate, concentration of polymer in the spray fluid, the viscosity of the spray fluid, and the distance of the nozzle from the surface of the underlying structure 10, the diameter of the fibers formed during the spinning process can be controlled. For exemplary descriptions of the various factors, see, e.g., "Electrostatic Spinning and Properties of Ultrafine Fibers", Rutledge, et al., National Textile Center Annual Report, M01-D22, (November 2001), incorporated herein by reference. See also further description on the internet at www.che.vt.edu/Wilkes/electrospinning/electrspinning.html. It is also consistent with the fiber meshwork that the diameter of the fibers can be changed during deposition.

A further advantage of FFESS is thus that, because of the high degree of control of the fiber diameter, if the weight of the fiber meshwork as well as the density of the polymer material for a given fiber diameter are known, the total surface area of the meshwork can be precisely calculated. Thus, the surface area of a fiber of diameter d, and of length l, assuming a uniform perfectly cylindrical constant cross-section along its length, is $\pi d l$, ignoring contributions from the ends of the fibers. FFESS is further described in "Controlling surface nano-structure using flow-limited field-injection electrostatic spraying (FFESS) of poly(d,l-lactide-co-glycolide)", Berkland, Pack, and Kim, *Biomaterials*, 25: 5649-5658, (2004) and U.S. Patent Application Publication No. 2004/0022939, both of which are incorporated herein by reference in their entirety.

The median diameter of the fiber or fibers in the fiber meshwork can be less than about 1 micron, for example, less than about 500 nm. In some embodiments, the fibers have a median diameter from about 5 nanometers to about 500 nanometers. For example, the fibers can have a median diameter of about 50 nm, about 100 nm, about 150 nm, about 200 nm, about 250 nm, about 300 nm, about 350 nm, about 400 nm, or about 450 nm. By use of the qualifier "about", it would be understood by one of ordinary skill in the art that a reference to a median diameter of, for example, about 300 nm, would encompass other median diameters within +/−25 nm of 300 nm. It is to be understood that where a fiber is not perfectly circular in cross-section, the diameter of a particular fiber can refer to an average length of any two orthogonal lines that both pass through the geometric center of the fiber cross-section and have end points on the perimeter of the fiber, or to the length of any one such line. It is also to be understood that although the diameter of a fiber can vary along its length, the diameter is the mean diameter of the fiber.

Other morphologies could be utilized to the extent that they embody the properties desired of a polymer structure for placing on the surface of an underlying structure 10. As further discussed herein, such properties include at least an ability to substantially retain shape after the underlying structure has biodisintegrated, a porosity sufficient to permit access of body fluids to the underlying structure, and a sufficient surface area to give rise to sustained release of a therapeutic agent absorbed within the polymer structure or from layers coated upon it. Other morphologies of polymer such as particles, beads, porous sheets, webs, nets and smooth surfaces may be created with FFESS, as further illustrated in Berkland, et al., *Biomaterials*, 25: 5649-5658, (2004) and U.S. Pat. App. Pub. No. 2004/0022939. A web or net-like structure for the fiber meshwork is advantageous because it reduces the chance that short individual fibers can become disconnected from the underlying structure.

It is also consistent with the fiber meshwork used herein that the fiber is deposited as a mixture of fibers and beads. As further described herein, a fiber composed of a biodegradable material in which is embedded a therapeutic agent will release the agent at a rate that depends upon the diameter of the fiber. It can be advantageous to mix in amongst such fibers beads of material which, being thicker than the fibers, will release the therapeutic agent over a more prolonged period of time. One of ordinary skill in the art is capable of manipulating the electrospinning process to ensure production of beads at one time, fibers at one time, or a mixture of beads and fibers. See, e.g., Shenoy, S. L., et al., "Role of chain entanglements on fiber formation during electrospinning of polymer solutions: good solvent, non-specific polymer-polymer interaction limit", *Polymer,* 46:3372-3384, (2005), in particular FIG. 1 therein, and Tan, et al., "Systematic parameter study for ultra-fine fiber fabrication via electrospinning process", *Polymer,* 46:6128-6134, (2005), both of which are incorporated herein by reference.

Figure 4:
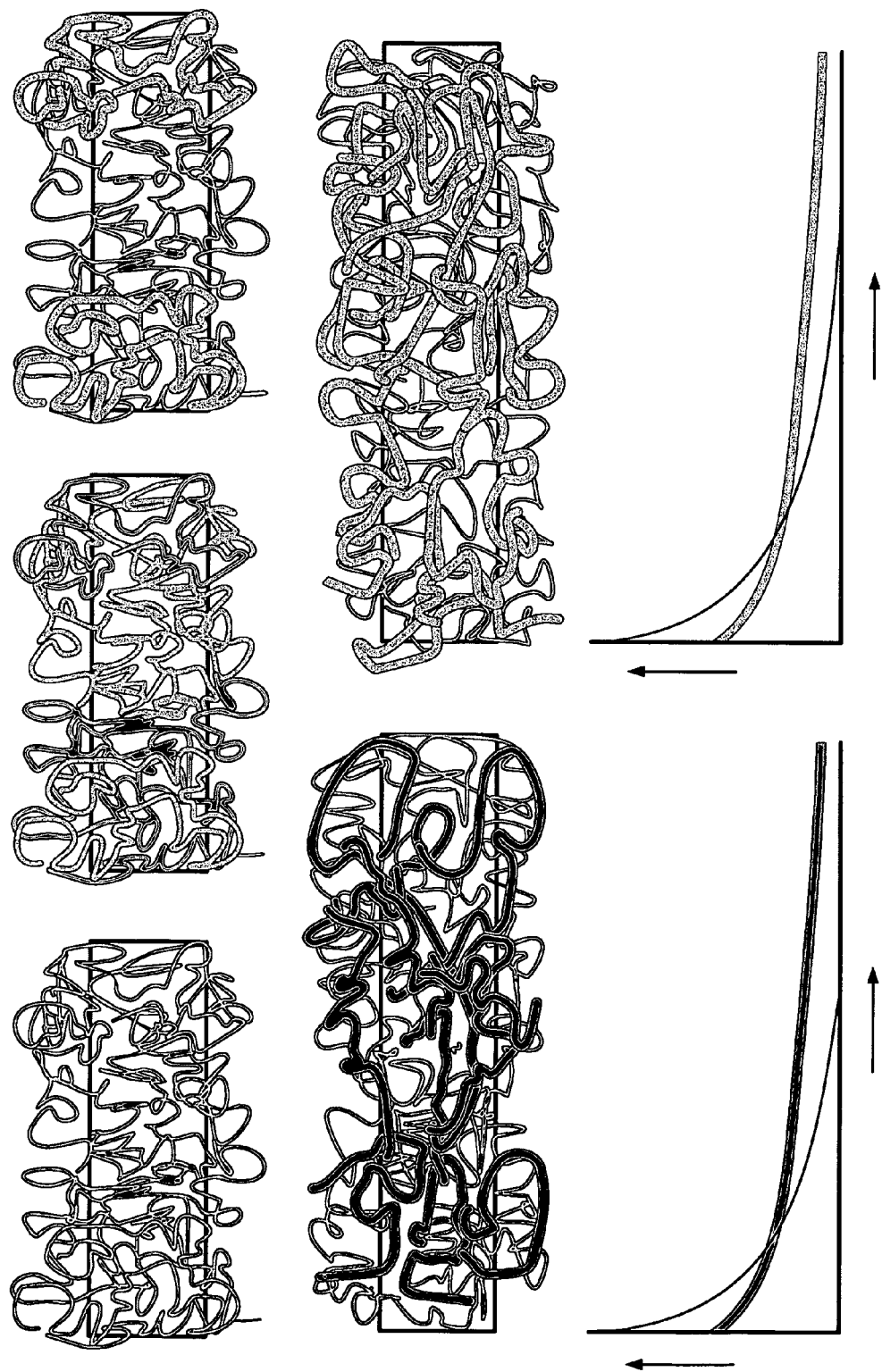
FIG. 4 shows various options for a meshwork composed of two different drug filled polymers with different fiber thicknesses and their respective drug release profiles with time.

There are various options, familiar to one of ordinary skill in the art, for introducing a therapeutic agent into the fiber meshwork. A first option is to place the therapeutic agent inside the fiber material as it is being sprayed by a process such as FFESS. Thus the drug may be dissolved in the polymer solution before it is sprayed. This approach is also advantageous because it is possible to spray different therapeutic agents from different fibers using different nozzles to achieve simultaneous delivery of a mixture of drug components, as shown in FIG. 4. For example, at the top of FIG. 4 are shown three embodiments of a stent having disposed thereon, from left to right, a fiber meshwork made from a single fiber, two fiber meshworks made from fibers of the same thickness, and two fiber meshworks made from fibers of different thicknesses wherein the thicker fibers are only disposed at the ends of the stent. The lower portion of FIG. 4 shows two embodiments of a stent, having fiber meshworks composed of fibers of different thicknesses disposed thereon and, below each, drug release profiles showing concentration of released drug (vertical axis) as a function of time (horizontal axis). On the left hand side, the same drug is loaded into fibers of different thicknesses, and on the right hand side, different drugs are loaded into fibers of different thicknesses.

The level of control of fiber diameter achievable with FFESS is also useful because, as further described herein, release of a therapeutic agent absorbed in such fibers is directly related to the diameter of the fibers. The porous structure of the fiber meshwork disposed on the underlying structure allows all of the fibers to release their drug content directly to the surrounding milieu at the same time. Furthermore, by ensuring a specific fiber diameter, a specific release profile can be achieved. In other embodiments, use of FFESS permits creation of a differential release profile across the medical device. For example, by spraying a thinner fiber-structure at the end sections of the device, one can obtain a higher drug release at the ends by virtue of a higher surface area to volume ratio there.

A second option for introducing a therapeutic agent into the fiber meshwork is to embed Magnetite nano-particles into the fibers. Such nano-particles are ferro-magnetic and would themselves permit binding of magnetic drug delivery particles to the fiber matrix by methods within the capability of one of ordinary skill in the art. For examples of magnetic drug delivery particles, see, e.g., "Functionalisation of magnetic nanoparticles for applications in biomedicine", Berry, C. C., et al., *J. Phys. D: Appl. Phys.,* 36 R198-R206, (2003), incorporated herein by reference in its entirety. In one such embodiment, as a pre-requisite to facilitating such a delivery mechanism, one would start with a dispersion of a desired nanoparticle in a polymer-solvent solution; the solution would be spun into fibers, such as with FFESS, such that the fibers themselves have the nanoparticles incorporated therein.

The fiber meshwork may also contain a nanocomposite instead of or in addition to a purely polymeric material. "Nanocomposite" refers to a composition comprising a polymeric material and relatively small amounts (generally less than about 10% by weight) of nanometer-sized (average size smaller than 1 micrometer) mineral, clay, or nanosized ceramic particles dispersed therein. Sometimes nanocomposites are referred to as "nanoclay" or "nanoceramic". For example, nanocomposites are disclosed in International Publication No. WO 93/1014118, and U.S. Pat. Nos. 5,385,776, and 6,251,980 all of which are incorporated herein by reference in their entirety. These particles may themselves contain therapeutic agents that are released as the polymer of the meshwork degrades.

Another approach is to use liposomes, which are embedded in the fiber meshwork. Methods of embedding liposomes into thin films have been described elsewhere, and are generally known to one of ordinary skill in the art (see, e.g., Vermette et al., "Immobilized liposome layers for drug delivery applications: inhibition of angiogenesis", *J. Controlled Release,* 80:179-195 (2002)). Liposomes are lipid-bilayer bound vesicles, typically less than 1 micron in diameter, for example, in the range 50-400 nm in diameter, that can be used as drug-delivery vehicles. Typically such liposomes are electrically charged: both cationic and anionic liposomes are known in the art as drug delivery vehicles. Therapeutic agents can be encapsulated into liposomes prior to implantation in an organism, and slowly leech out as the liposome degrades. An advantage of attaching capsules to the PEI fiber meshwork instead of attaching them to the stent surface (e.g., by means of coating the stent with self-assembled poly-electrolyte multi-layers), is that if the capsules are large enough compared to the porosity of the fibrous network, then the capsules can be trapped in between the stent and the vessel wall.

Charged liposomes can bind to a fiber meshwork as described herein by, for example, coating the fiber meshwork with a layer-by-layer composition (of alternating cationic and anionic layers) such that the outermost (last-deposited) layer has an opposite charge to that of the liposome. Thus after coating, if fibers having an anionic outer layer (for example) are dipped into a solution of cationic liposome particles, the liposomes become bound to the fiber meshwork. It is also consistent with the medical device described herein that liposomes can be bound by magnetic attraction to a fiber meshwork. For example, as described hereinabove, fibers of the fiber meshwork can comprise magnetic nanoparticles. Liposomes having magnetite particles (see, e.g., Matsuoka, F., et al., "Hyperthermia using magnetite cationic liposomes for hamster osteosarcoma", *BioMagnetic Research and Technology,* Vol. 2, p. 3 et seq., (2004), incorporated herein by reference) can bound to such a fiber meshwork.

In still other embodiments, as an alternative to liposomes, polyelectrolyte multilayer capsules may be used as transporters of drugs that may be embedded in a fiber meshwork. Drug-filled polyelectrolyte capsules can be prepared by any one of several methods known to one of ordinary skill in the art, (see, e.g., Antipov, A. A., and Sukhorukov, G. B., "Polyelectrolyte multilayer capsules as vehicles with tunable permeability", *Adv. Colloid and Interface Sci.,* 111, 49-61, (2004)).

The use of drug-containing capsules such as liposomes and polyelectrolyte multi-layer capsules addresses one of the drawbacks of devices in the art such as drug-eluting stents. Such devices offer only a non-homogeneous drug delivery profile because the drug is supplied by the framework of the device, such as the struts of a stent. This mechanism leaves large areas in between the struts free of the drug. Although there is some movement of the drug from the area immediately adjacent to the struts to the open cell area, there is always a difference in concentration between such regions. Trapping drug filled capsules in between a fiber meshwork and the wall of the body lumen gives a much more homogeneous release profile. This is particularly important in applications such as abluminal drug release.

Figure 5A:
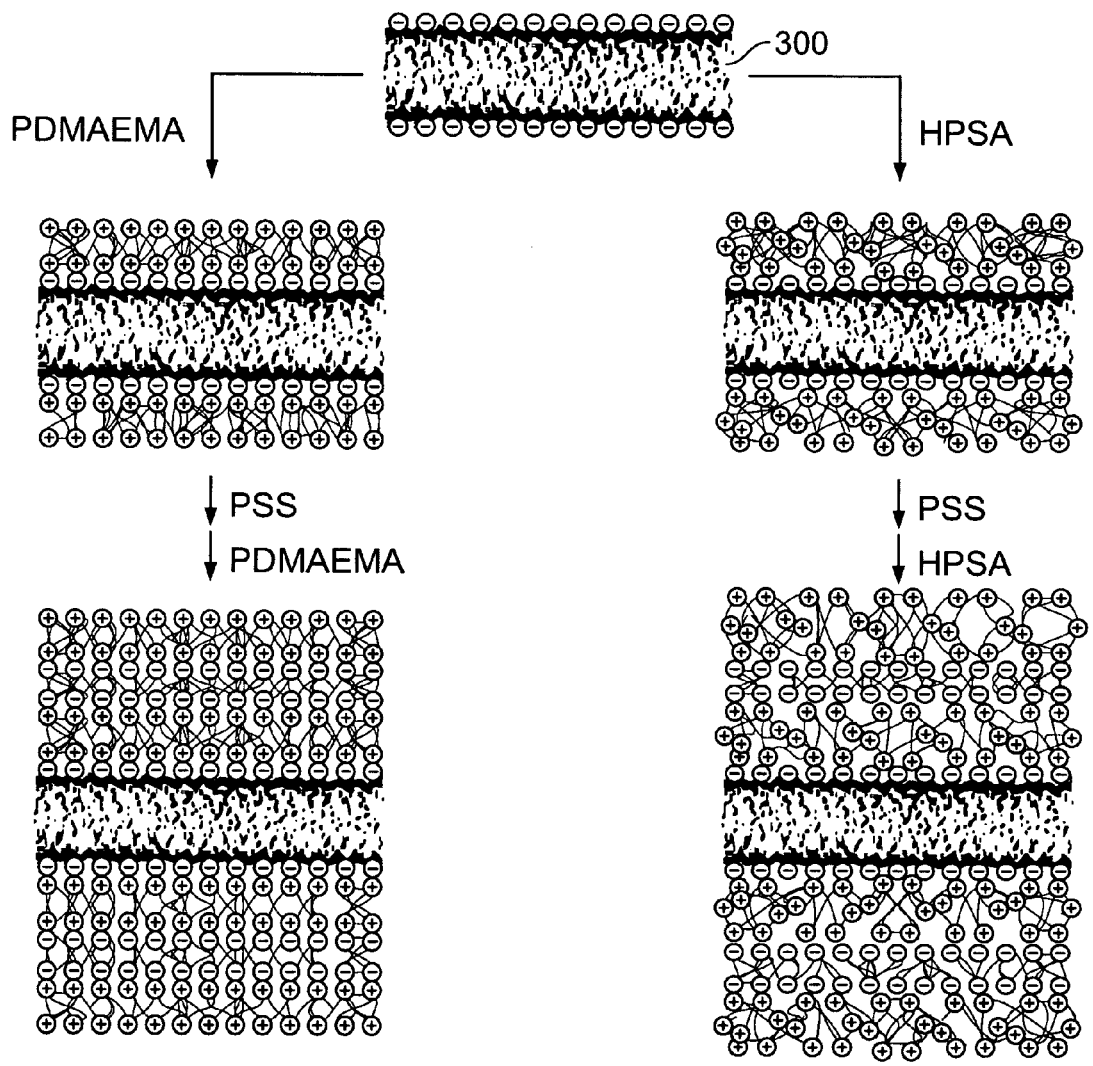
FIGS. 5A and 5B show various polymer layers suitable for use with a fiber meshwork, and their respective structural formulae.
Figure 5B:
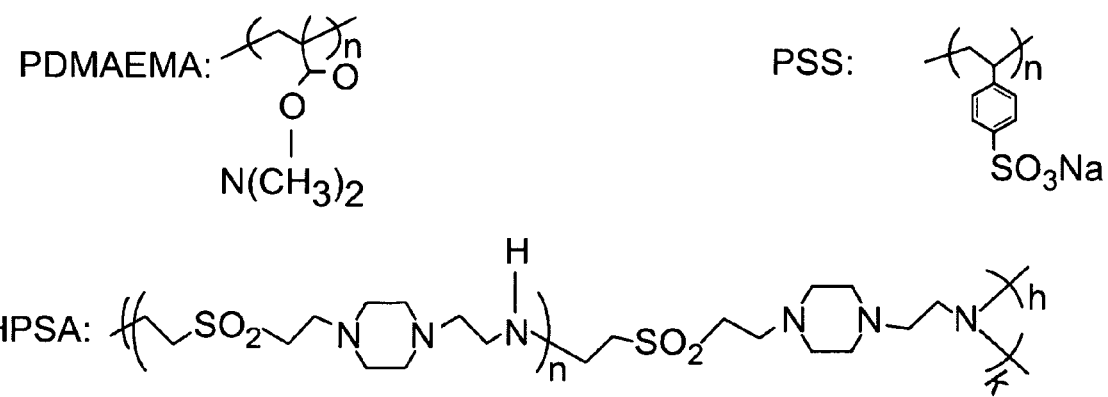
Figure 6:
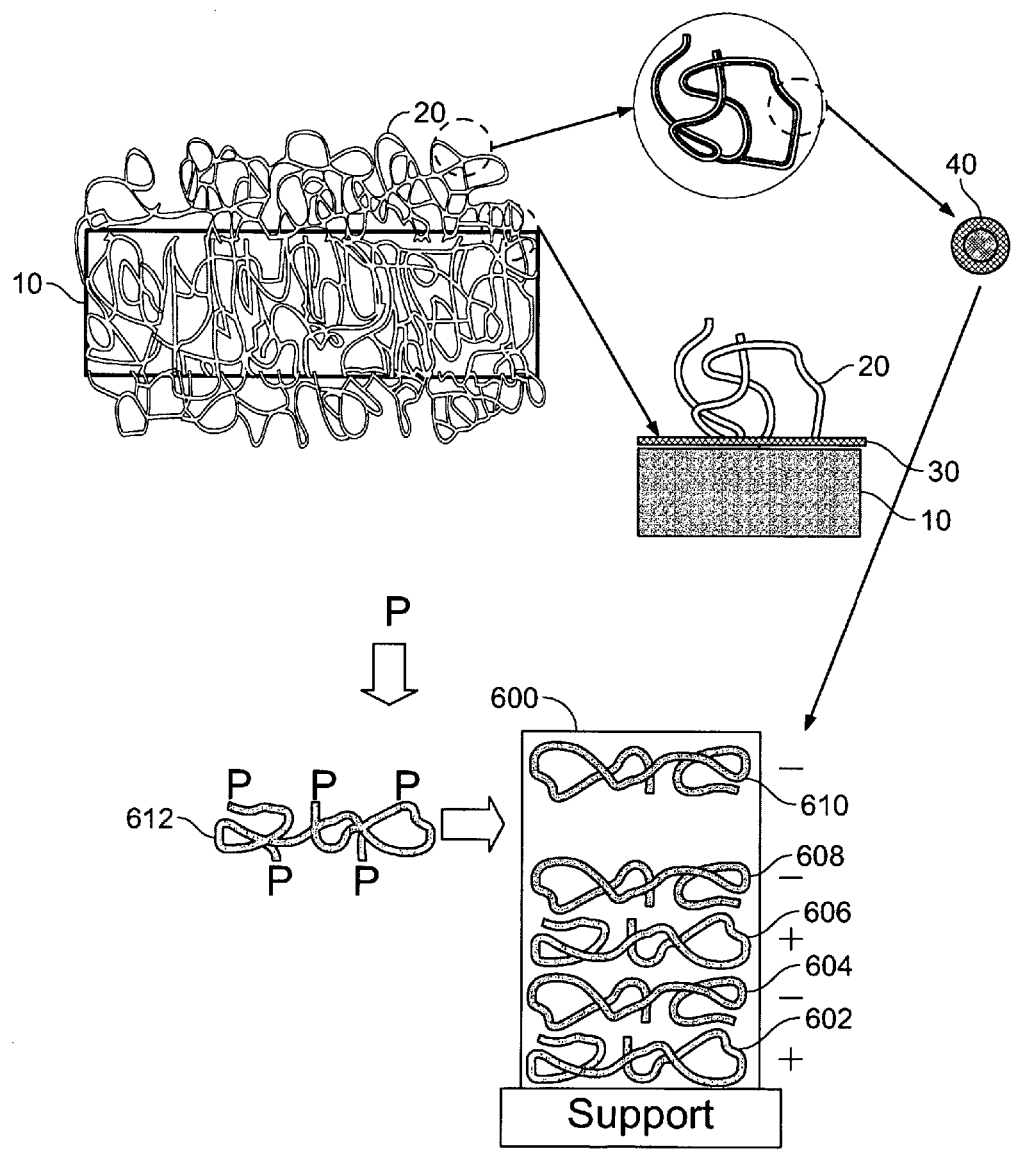
FIG. 6 shows various configurations of layer-by-layer coatings that contain drugs, and are deposited on the mechanical support or on the fiber meshwork.

In an alternative embodiment, a therapeutic agent is introduced into a medical device via a layer-by-layer (LBL) coating process which overcoats the fiber-meshwork with one or more alternating single molecular layers of cationic and anionic materials, as further described herein. Many bioactive molecules, such as proteins, enzymes, DNA, are charged, and can be readily included in these types of coatings. A number of LBL coatings, as shown in FIGS. 5 and 6, and as further described herein, can be used. The LBL coating process can permit coating of highly complex 3D structures without webbing, and is able to penetrate inside complex structures. Webbing is an effect that occurs when a very viscous solution is applied to coat very fine wires. The coating will form a kind of webbing between one fiber and another, which can be undesirable. Since layer by layer technology uses low viscous water-based solutions, it can penetrate into all manner of geometries without the risk for webbing. An example is described in, e.g., Artyukhin, et al., *Langmuir,* 20, 1442-1448, (2004), and H. Kong, et al., "Polyelectrolyte-functionalized multiwalled carbon nanotubes: preparation, characterization and layer-by-layer self-assembly", *Polymer* 46:2472-2485, (2005), both of which are incorporated by reference herein in their entirety, and which demonstrate overcoating of multiwall carbon nano-tubes with several layers of different molecules. This process is carried out in a batch process without the fibers sticking together, as shown in FIG. 5. A functionalized multi-wall carbon nanotube (MWNT) 300 such as MWNT-COOH, MWNT-PAA (where PAA is polyacrylic acid), or MWNT-PSS (where PSS is poly(sodium 4-styrenesulfonate)) can accept a number of layers of different charge, disposed thereon. For example, HPSA (hyperbranched polysulfone amine) and PDMAEMA (poly(2-(N,N-dimethylaminoethyl) methacrylate), both of which are positively charged, can be disposed on a MWNT functionalized with negatively charged groups such as carboxylates. Thereafter, alternating layers of PSS (negatively charged) and PDMAEMA or HPSA can be further built up. Each of HPSA, PSS or PDMAEMA can be disposed as a fiber meshwork. The formulae of PSS, HPSA, and PDMAEMA are shown in FIG. 5B.

In any of the embodiments herein, the fiber meshwork is able to elute a drug contained within it, or absorbed in a layer upon it, over a longer period of time than the lifetime of the mechanical support.

Layer-By-Layer Technology

The fiber-meshwork sprayed by a method such as FFESS can be overcoated with several layers, one or more of which contains a therapeutic agent, using layer-by-layer (LBL) technology. The layer-by-layer coating process produces a multi-layered structure such as 40, in FIG. 1B, on the fiber meshwork. Advantages of such an arrangement include a controlled release profile of the therapeutic agent. For example, if desired, a profile may be designed to include a first phase, characterized by a massive release of the agent from the top LBL coating by virtue of its large surface area, followed by a secondary release of the agent out of deeper layers of the LBL coating, or from the fiber meshwork itself as also discussed herein. Adjustment of concentrations of the therapeutic agent at various layers, taking into account their respective thicknesses, solubilities, and surface areas, can ensure a specific desired release profile. LBL coatings are also very effective in preventing degradation of the fiber meshwork, because they follow complex surfaces precisely, such as those of the fiber meshwork, and they are composed out of charged molecules which impede free motion of water molecules through the coating.

In some embodiments, the use of an LBL coating on the underlying structure 10, either instead of or as well as one on the fiber meshwork, allows control of the disintegration (e.g., corrosion) of the underlying structure over a desired timeframe. This may be important if it is wished to maintain the mechanical integrity of the device for such a defined timeframe. FIG. 6 shows an underlying structure 10 having a fiber meshwork 20 disposed thereon. The fibers of fiber meshwork can also have a layer-by-layer coating 40 disposed thereon, as shown in the various cutouts. The underlying structure 10 can also have a layer-by-layer structure 30 disposed thereon. The bottom of FIG. 6 shows a schematic of a device having multiple fiber meshworks 600 disposed on an underlying structure (denoted "support"). Each of the fiber meshworks 602-612 alternates in charge to facilitate deposition. Peptide molecules are denoted "P" and are attached to fibers of one of the fiber meshworks 612. It is to be understood that molecules other than peptides can be similarly attached to one or more of the fiber meshworks.

Layer by Layer Coatings

In some embodiments, at least one of the charged layers includes a polyelectrolyte. Polyelectrolytes are polymers having charged groups or groups that dissociate to form ions (also called polyions). The number of these groups in a polyelectrolyte can be so large that the polymer is soluble in polar solvents (including water) when in ionic form. One or more charged layers can include one type of polyelectrolyte or different types of polyelectrolytes.

Depending on the type of dissociable groups, polyelectrolytes can be classified as polyacids and polybases.

When dissociated, polyacids form polyanions, after protons have been released. Polyacids include inorganic and organic molecules, as well as biopolymers. Examples of polyacids are polyphosphoric acids, polyvinylsulfuric acids, polyvinylsulfonic acids, polyvinylphosphonic acids, and polyacrylic acids. Examples of the corresponding salts, which are called polysalts, are polyphosphates, polyvinylsulfates, polyvinylsulfonates, polyvinylphosphonates and polyacrylates, respectively.

Examples of anionic polyelectrolytes (polyanions) include poly(styrenesulfonate) polyanions (e.g., poly(sodium styrene sulfonate) (PSS)), polyacrylic acid polyanions, sodium alginate polyanions, eudragit polyanions, gelatin polyanions, hyaluronic acid polyanions, carrageenan polyanions, chondroitin sulfate polyanions, and carboxymethylcellulose polyanions.

Polybases contain groups that are capable of accepting protons, e.g., by reaction with an acid, to form a salt. By accepting protons, polybases form cationic polyelectrolytes (polycations).

Examples of polybases having dissociable groups within their backbone and/or side groups are polyallylamine, polyethylimine, polyvinylamine and polyvinylpyridine.

Still other examples of polyelectrolyte cations (polycations) include protamine sulfate polycations, poly(allylamine) polycations (e.g., poly(allylamine hydrochloride) (PAH)), polydiallyldimethylammonium polycations, polyethyleneimine polycations, chitosan polycations, gelatin polycations, spermidine polycations and albumin polycations Some polyelectrolytes have both anionic and cationic groups, but nonetheless have a net positive or negative charge. An example of such a polyelectrolyte is gelatin. Some polyelectrolytes have combinations of both anionic and cationic groups such as to maintain electrical neutrality. Whether a polyelectrolyte having both anionic and cationic groups has a net positive or negative charge can depend, for example, on the pH of the environment surrounding the polyelectrolyte.

The polyelectrolytes for use with layer-by-layer coatings can include those based on biopolymers. Examples include alginic acid, gum arabicum, nucleic acids, pectins, proteins, chemically modified biopolymers such as carboxymethyl cellulose, and lignin sulfonates.

The polyelectrolytes for use with layer-by-layer coatings can also include those based on synthetic polymers, such as polymethacrylic acid, polyvinylsulfonic acid, polyvinylphosphonic acid and polyethylenimine.

Polyelectrolytes may be linear or branched, either or both of which can be used. Using branched polyelectrolytes can lead to less compact polyelectrolyte multilayers having a higher degree of wall porosity. In some embodiments, polyelectrolyte molecules can be crosslinked within and/or between the individual layers, to enhance stability, e.g., by crosslinking amino groups on one polymer molecule with aldehyde moieties on another.

Furthermore, in certain embodiments, polyelectrolytes can be amphiphilic. Amphiphilic substances can include any substance having hydrophilic and hydrophobic groups. Amphiphilic polyelectrolytes, e.g., amphiphilic block or random copolymers having partial polyelectrolyte character, can be used in some embodiments to affect permeability towards polar small molecules. In some embodiments, a layer including an amphiphilic polyelectrolyte may be more permeable to polar molecules than a layer including a polyelectrolyte that is not amphiphilic.

Amphiphilic polyelectrolytes can be used as ionic amphiphilic substances in some embodiments. For example, a polyelectrolyte comprising charged groups (which are hydrophilic) as well as hydrophobic groups, such as polyethylenimine (PEI) or poly(styrene sulfonate) (PSS), can be employed.

Cationic and anionic surfactants may also be used as amphiphilic substances in some embodiments of the layer by layer coatings used with the present invention. Cationic surfactants include quaternary ammonium salts ($R_4N^+X^-$), where R is an organic radical and where $X^-$ is a counter-anion, e.g., a halide. Thus, examples of cationic surfactants include didodecyldimethylammonium bromide (DDDAB); alkyltrimethyl-ammonium bromides such as hexadecyltrimethylammonium bromide (HDTAB), dodecyltrimethylammonium bromide (DTMAB), myristyltrimethylammonium bromide (MTMAB), or palmityltrimethylammonium bromide; tertiary amines ($R_3NH^+X^-$), such as cholesteryl-3β-N-(dimethyl-aminoethyl)-carbamate; and N-alkylpyridinium salts; or mixtures thereof. Anionic surfactants include alkyl or olefin sulfates of general formula $R-OSO_3^- M^+$ where $M^+$ is a metal counter-ion. Examples include a dodecyl sulfate such as sodium dodecyl sulfate (SDS), and a lauryl sulfate such as sodium lauryl sulfate (SLS). Anionic surfactants further include an alkyl or olefin sulfonate of general formula $R-SO_3^- M^+$, for example, sodium-n-dodecylbenzene sulfonate. Still further examples of anionic surfactants include fatty acids (of formula $R-COO^-M^+$, where R is an organic radical and $M^+$ is a counter-cation), for example, a dodecanoic acid sodium salt, or other acids including phosphoric acids, cholic acids, fluoro-organic acids such as lithium-3-[2-(perfluoroalkyl)ethylthio]propionate, or mixtures thereof.

Exemplary polyelectrolytes for use with the multi-layer structures have molecular weights ranging from a few hundred Daltons (low-molecular weight polyelectrolytes) up to several million Daltons, as commonly found with macromolecular polyelectrolytes (e.g., polyelectrolytes of synthetic or biological origin).

When disposed on the underlying device structure, the polyelectrolyte layers can restrict or prevent water molecules and/or certain ions from accessing the biodisintegrable materials of the underlying device structure. In certain embodiments, polyelectrolytes can, in addition to the fiber meshwork, prevent the biodisintegrable materials from disintegrating prematurely (e.g., during delivery and/or deployment of the medical device to a target site). In still other embodiments, such layers include one or more therapeutic agents. In still other embodiments, one or more layers contain a radiopaque material, and/or one or more layers capable of enhancing the mechanical properties of the device structure.

In some embodiments, the layers of the multi-layer structure disposed on the underlying structure include biodegradable polyelectrolytes that degrade at a slower rate than the rate of disintegration of the biodisintegrable material of the underlying structure. As the underlying structure disintegrates, it may break into multiple pieces. Because the layers of polyelectrolytes degrade at a slower rate than the biodisintegrable material of the underlying structure, at least some of the layers may limit or prevent movement of these multiple pieces to other places in the body, causing the pieces to disintegrate and be resorbed instead at the implantation site within the body.

In some embodiments, a layer formed of a biodegradable polyelectrolyte can degrade over a period of at least about one second (e.g., at least about 10 seconds, at least about 30 seconds, at least about one minute, at least about 10 minutes, at least about one hour, at least about five hours, at least about 10 hours, at least about one day, at least about two days, at least about four days, at least about six days), and/or at most about one week (e.g., at most about six days, at most about four days, at most about two days, at most about one day, at most about 10 hours, at most about five hours, at most about one hour, at most about 10 minutes, at most about one minute, at most about 30 seconds, at most about 10 seconds).

In some embodiments, biodegradable polyelectrolytes can be used so that a therapeutic agent can be released into the subject at a rate that is dependent upon the rate of degradation of the polyelectrolyte layers. For example, by using polyelectrolytes that are biodegradable near the outer surface of the medical device, this rate can be initially highest. Biodegradable polyelectrolytes can also be used in embodiments in which the underlying structure, and/or a fiber meshwork disposed thereon, is itself biodisintegrable. As the biodegradable polyelectrolytes in layers of the coating disintegrate, they may provide less protection for the underlying device structure. As a result, the structure can begin to disintegrate or can disintegrate at a faster rate.

Examples of biodegradable polyelectrolytes include heparin, polyglycolic acid (PGA), polylactic acid (PLA), polyamides, poly-2-hydroxy-butyrate (PHB), polycaprolactone (PCL), poly(lactic-co-glycolic)acid (PLGA), protamine sulfate, polyallylamine, polydiallyldimethylammonium species (e.g., poly(diallyldimethyl-ammonium chloride) (PDADMA, available from Aldrich)), polyethyleneimine, chitosan, eudragit, gelatin, spermidine, albumin, polyacrylic acid, sodium alginate, poly(styrene sulfonate) (PSS, Scientific Polymer Products), hyaluronic acid, carrageenan, chondroitin sulfate, carboxymethylcellulose, polypeptides, proteins, DNA, and poly(N-octyl-4-vinyl pyridinium iodide) (PNOVP). Biodegradable polyelectrolytes are described, for example, in T. R. Farhat and J. B. Schlenoff, "Corrosion Control Using Polyelectrolyte Multilayers", *Electrochemical and Solid State Letters,* 5(4) B13-B15 (2002), incorporated by reference herein.

In other embodiments, the layers are made from biostable polyelectrolyte materials, or the entire multi-layer structure is constructed so as to be biostable. Thus if, for example, various layers are cross-linked to each other so that the multi-layered structure is biostable, the underlying structure may disintegrate over a given period of time, while the multi-layer structure remains in the body of the subject. Accordingly, in certain embodiments, an endoprosthesis can include two or more polyelectrolyte layers that are cross-linked to each other. The cross-linked polyelectrolyte layers may be used, for example, to confine a biodisintegrable material in the underlying structure. In certain embodiments, this confinement of the biodisintegrable material may limit the likelihood that one or more pieces of the biodisintegrable material will break away from the endoprosthesis during use and move to a location other than the target site.

In some embodiments, a medical device can include a structure (e.g., a multi-layered structure) having a combination of cross-linked polyelectrolytes and biodegradable polyelectrolytes, to provide further tailoring of the disintegration of the device.

In certain embodiments, a biodegradable polyelectrolyte in one layer can be cross-linked (e.g., using heat and/or UV radiation) to another biodegradable polyelectrolyte in another layer. In some embodiments, cross-linking between polyelectrolytes in different layers can cause the polyelectrolytes to degrade at a slower rate than they would otherwise. In certain embodiments, a layer including a cross-linked polyelectrolyte can degrade over a period of at least about one week (e.g., at least about two weeks, at least about three weeks, at least about four weeks, at least about six weeks, at least about eight weeks, at least about 10 weeks, at least about 12 weeks, at least about 14 weeks, at least about 16 weeks, at least about 18 weeks, at least about 20 weeks, at least about 22 weeks), and/or at most about 24 weeks (e.g., at most about 22 weeks, at most about 20 weeks, at most about 18 weeks, at most about 16 weeks, at most about 14 weeks, at most about 12 weeks, at most about 10 weeks, at most about eight weeks, at most about six weeks, at most about four weeks, at most about three weeks, at most about two weeks).

As an example of cross-linking layers, a polyelectrolyte layer including diazonium cations may be covalently cross-linked to a polyelectrolyte layer including sulfonate groups or acrylic acid groups, using UV radiation or heat. As another example, a polyelectrolyte layer including a diazo resin may be cross-linked to a polyelectrolyte layer including polyoxometalates. As an additional example, ammonium groups in one polyelectrolyte layer may be covalently bonded to carboxylate groups in another polyelectrolyte layer. In certain embodiments, polyelectrolyte layers including poly(allylamine hydrochloride) (PAH) can be covalently bonded to polyelectrolyte layers including poly(acrylic acid) (PAA). Cross-linking of polyelectrolyte layers is described, for example, in Zhang et al., "Improving multilayer films endurance by photoinduced interaction. between Dawson-type polyoxometalate and diazo resin", *Materials Chemistry and Physics,* 90 (2005), 47-52, and in Zhang et al, "Ways for fabricating stable layer-by-layer self-assemblies: combined ionic self-assembly and post chemical reaction", *Colloids and Surfaces A: Physicochemical and Engineering Aspects,* 198-200, 439-442, (2002), both of which are incorporated herein by reference in their entirety.

In some embodiments, one or more of the top polyelectrolyte layers on a medical device can be cross-linked. This can, for example, limit or prevent degradation or dissolution of the multi-layer structure on the medical device in the body. For example, multiple layers of polyallylamine hydrochloride (PAH) and polyacrylic acid (PAA) can be deposited on a plurality of other polyelectrolyte layers. The entire multi-layered structure can then be heated at 130° C. for about an hour under a nitrogen atmosphere to crosslink the ammonium groups of the PAH and the carboxylic groups of the PAA to form amide bonds. A nylon-like top film that is impermeable to liquids can be created. In certain embodiments, this liquid-impermeable top film can later be removed (e.g., using excimer ablation).

In some embodiments, one or more regions of a polyelectrolyte layer may be cross-linked to one or more regions of another polyelectrolyte layer (e.g., by selectively irradiating certain regions of the polyelectrolyte layers), while the polyelectrolyte layers may not be cross-linked to each other in other regions.

In certain embodiments in which a multi-layered structure is biostable, the multiple layers may have one or more (e.g., two, three, four, five, 10, 15, 20, 25, 50, 100, 500, or 1,000) holes in them in order to facilitate biodisintegration of the device on which the structure is placed. In some embodiments, the one or more holes can be added to a layer using a laser. The holes can, for example, provide water and/or ions with limited access to the underlying structure, thereby helping to cause the underlying structure to disintegrate.

In some embodiments, the multi-layer structure comprises one or more non-polyelectrolyte layers. The non-polyelectrolyte layers can be biodisintegrable or biostable. Examples of non-polyelectrolyte biodisintegrable materials include polylactides such as polylactic acid (PLA), polyglycolides such as polyglycolic acid, poly(lactide-co-glycolides), polyanhydrides, and polyorthoesters. Accordingly, an endoprosthesis according to the present invention, can further include one or more non-polyelectrolyte layers, which can be added to it using, for example, a spraying technique. The non-polyelectrolyte layer(s) may be added on top of and/or underneath the multi-layered structure. In some embodiments, an endoprosthesis can include more than one multi-layered structure, and/or can include one or more non-polyelectrolyte layers located between the multi-layered structures. In some embodiments, the non-polyelectrolyte layer(s) may be thicker than one or more of the layers in the multi-layered structure(s). In certain embodiments, a non-polyelectrolyte layer may exhibit better adhesion to the surface of a tubular structure of an endoprosthesis than a polyelectrolyte layer.

In certain embodiments, a multi-layered structure may include at least two positively charged layers that are formed of different materials (e.g., different polyelectrolytes) and/or at least two negatively charged layers that are formed of different materials (e.g., different polyelectrolytes).

In some other embodiments, one portion of the underlying structure may be coated with a multi-layered structure, while another portion of the underlying structure may not have any coatings on it, or may be coated with just one layer.

In certain embodiments, when it is desired to increase the permeability of the medical device to magnetic fields, charged layers of a multi-layer structure containing various polyelectrolytes can be interleaved with other layers that contain magnetic clusters. Examples of incorporating inorganic materials such as polyoxometalates in a multi-layered structure using a layer-by-layer method are described, for example, in Caruso et al., *Langmuir* (1998), 14, 3462-3465, and also in pending U.S. patent application Ser. No. 10/985,242, both of which are incorporated herein by reference in their entirety.

A multi-layered structure in conjunction with a fiber meshwork can also be applied to the underlying structures of numerous medical devices. For example, they can be applied to grafts, filterwires, valves, filters (e.g., vena cava filters), aneurysm coils, distal protection devices, guidewires, and other implantable devices. In some embodiments, a multi-layered structure can be applied to a catheter (e.g., a renal or vascular catheter such as a balloon catheter). In certain embodiments, a multi-layered structure can be applied to a balloon. In some embodiments, a multi-layered structure such as multi-layered structure can be applied to a coil (e.g., an aneurysm coil). Coils are described, for example, in Twyford, Jr. et al., U.S. Pat. No. 5,304,195.

In some embodiments, the multi-layered structure can include nanoparticles. The nanoparticles can, for example, enhance the mechanical properties (e.g., strength) of the multi-layered structure. The nanoparticles can have at least one dimension (e.g., the thickness for a nanoplate, the diameter for a nanosphere, a nanocylinder and a nanotube) that is less than 1,000 nanometers (e.g., less than 100 nanometers). Nanoplates can have at least one dimension that is less than 1,000 nanometers; nanofibers can have at least two orthogonal dimensions (e.g., the diameter for a cylindrical nanofiber) that are less than 1,000 nanometers; and other nanoparticles can have three orthogonal dimensions (e.g., the diameter for nanospheres) that may be less than 1,000 nanometers.

Forming Layer-by-layer Structures

In certain embodiments, charged layers containing various polyelectrolytes can be interspersed with other layers to form a multi-layer structure using a method in which the layers electrostatically self-assemble. In this method, the so-called layer by layer method, a first layer comprising a first material having a first surface charge is deposited on an underlying structure or substrate, followed by a second layer comprising a second material having a second surface charge that is opposite in sign to the surface charge of the first layer. Thus, the charge on the outer layer is reversed upon deposition of each sequential layer. Additional layers, for example of first and second materials, can then be alternatingly deposited on the substrate to build a multi-layered structure to a predetermined or targeted thickness. This method allows a multi-layer structure to be formed on an underlying structure directly and/or, for example, on a flexible sleeve (e.g., a polymer sleeve) carried by the underlying structure, as well as on a fiber meshwork of the present invention. The layer-by-layer structure thus formed is capable of controlling the disintegration of the underlying structure, while allowing the device to remain flexible and adaptable to the vessel in which the device is implanted. Layer-by-layer self-assembly is described, for example, in Liu et al., *Journal of Cluster Science*, Vol. 14, No. 3, 405-419, (2003); and Caruso et al., *Langmuir*, 14, 3462-3465, (1998). The substrate can be the underlying structure, or the fiber meshwork.

Accordingly, once a layer having a preselected charge is provided on the underlying structure or fiber meshwork, the layer can be coated with a layer of an oppositely charged material. After each application of a successive layer, the device can be washed to remove excess material. A multi-layer structure can be formed by repeated treatment with alternating, oppositely charged, materials, e.g., a positive polyelectrolyte and a negative polyoxometalate, as described in pending U.S. patent application Ser. No. 11/127,968, incorporated by reference herein. The respective layers self-assemble by electrostatic layer-by-layer deposition, thus forming a multi-layered structure over the underlying structure or the fiber meshwork of the device.

In another embodiment, the multi-layer structure is formed by exposing a selected charged substrate (e.g., the underlying structure of a stent, or a fiber meshwork) to solutions or suspensions that contain species of alternating net charge, such as solutions or suspensions that optionally contain charged magnetic clusters, charged therapeutic agents and/or nanoparticles. The concentration of the charged species within these solutions and suspensions, which can be dependent on the types of species being deposited, can range, for example, from about 0.01 mg/ml to about 30 mg/ml. The pH of these suspensions and solutions can be such that polyelectrolytes, optional magnetic clusters, and therapeutic agents and/or nanoparticles to be included within the layers maintain their charge. Buffer systems can be used to maintain the pH and thereby the charges of the respective species.

The solutions and suspensions containing the charged species can be applied to the charged substrate surface using a variety of methods. Examples of such methods include spraying methods, dipping methods, roll and brush coating methods, ink jet methods, spin coating methods, web coating methods, microstamping methods, and methods involving coating via mechanical suspension such as air suspension, as well as combinations of these methods. Layers can be applied over an underlying structure by immersing the entire structure into a solution or suspension containing the charged species, or by immersing half of the structure into the solution or suspension, flipping the structure through 180°, and immersing the other half of the substrate into the solution or suspension to complete the coating. In some embodiments, the substrate is rinsed after application of each charged species layer, for example, using a washing solution with a pH that maintains the charge of the outer layer.

In some embodiments, the substrate is itself charged. A fiber meshwork can therefore be composed of charged polymer molecules or, at least, carries a surface charge to facilitate deposition of a first layer of a layer-by-layer structure upon it. Examples of such polymers include PEI, polyamides, polyacrylic acid, carboxymethyl cellulose, chitosan, PEI, polyamides, and polystyrene. The last of these, polystyrene, can be dissolved in an organic solvent such as THF after the layer-by-layer coating is assembled, thereby giving rise to a hollow fiber that can be filled with one or more therapeutic agents. The extent of surface charge on the surface of a given material can be deduced by measuring the Zeta-potential of the material, using methods known to one of ordinary skill in the art.

Using the methods described herein, multiple layers of alternating charge can thereby be applied to the fiber meshwork, or to an underlying structure. The number of layers varies according to application. In some embodiments, at least 10 layers (e.g., at least 20 layers, at least 30 layers, at least 50 layers, at least 100 layers, at least 200 layers) and/or at most 300 layers (e.g., at most 200 layers, at most 100 layers, at most 50 layers, at most 30 layers, at most 20 layers) can be applied over the substrate.

The total thickness of a multi-layered structure built up by a layer-by-layer process can be a function of the materials (e.g., polyelectrolytes) used, and can range, for example, from 5 nanometers to 1,500 nanometers. In some embodiments, the total thickness of the multi-layered structure can be at least five nanometers (e.g., at least 10 nanometers; at least 50 nanometers; at least 100 nanometers; at least 500 nanometers; at least 1,000 nanometers; at least 1,500 nanometers; at least 2,000 nanometers; at least 5,000 nanometers; at least 10,000 nanometers; at least 20,000 nanometers; at least 30,000 nanometers) and/or at most 40,000 nanometers (e.g., at most 30,000 nanometers; at most 20,000 nanometers; at most 10,000 nanometers; at most 5,000 nanometers; at most 2,000 nanometers; at most 1,500 nanometers; at most 1,000 nanometers, at most 500 nanometers, at most 100 nanometers, at most 50 nanometers, at most 10 nanometers).

The number of layers and/or the total thickness of a multi-layered structure deposited on a fiber meshwork, or an underlying structure, can be determined empirically and can be a function of, for example, the compositions of the layers and the type of medical device. For example, for a given medical device, the number of layers, their sequences and compositions, and/or the total thickness of multi-layered structure can be varied and the effectiveness of the multi-layered structure can be tested. After an effective combination is determined, the same combination can be repeatedly applied to other such devices.

In some embodiments, the multi-layered structure can be formed on a substrate, removed from the substrate, and subsequently applied (e.g., with an adhesive) to an underlying structure or a fiber meshwork of a medical device according to the present invention. When separating the multi-layered structure from the substrate, the substrate can be removed by destroying it, for example, by melting, sublimation, combustion, or dissolution, or a combination thereof, to free the multi-layered structure. For example, a removable substrate made of dental waxes (such as those available from MDL Dental Products, Inc., Seattle, Wash., USA) or polyvinyl alcohol can be used. These materials can respectively melt at moderately elevated temperatures (e.g., 60° C.) and dissolve in hot water. Other methods of using a removable substrate are described in Sukhorukov et al., "Comparative Analysis of Hollow and Filled Polyelectrolyte Microcapsules Templated on Melamine Formaldehyde and Carbonate Cores" *Macromol. Chem. Phys.*, 205, 2004, 530-535; and U.S. patent application Ser. No. 10/849,742, both of which are incorporated herein by reference in their entirety.

Layers of a multi-layer structure may have the same thickness as one another or different thicknesses. In some embodiments, the thickness of a layer may depend on the molecular weight of the materials, such as polyelectrolyte(s), included in the layer, and/or the presence of other materials (e.g., nanoparticles) in the layer. For example, a layer comprising a relatively low molecular weight polyelectrolyte, such as low molecular weight heparin (e.g., heparin having a molecular weight of from about 1,000 Daltons to about 10,000 Daltons) may be relatively thin. In certain embodiments, the thickness of a layer may depend on the conditions (e.g., salt concentration and/or pH) during the deposition of the layer. In some embodiments, an individual layer and/or an individual layer may have a thickness of at least about 0.2 nanometer (e.g., at least about 0.5 nanometer, at least about 1.0 nanometer, at least about 5.0 nanometers, at least about 10 nanometers, at least about 50 nanometers, at least about 100 nanometers, at least about 300 nanometers), and/or at most about 500 nanometers (e.g., at most about 300 nanometers, at most about 100 nanometers, at most about 50 nanometers, at most about 10 nanometers, at most about five nanometers at most about one nanometer, or at most about 0.5 nanometer).

In certain embodiments different regions of the medical device are coated with multi-layer structures having different numbers of layers. In some embodiments, the biodisintegrable material in a region of the underlying structure that is coated with a relatively large number of layers may begin to disintegrate after, and/or more slowly than, the biodisintegrable material in a region that includes a relatively small number of polyelectrolyte layers. Thus, the polyelectrolyte layers on an underlying structure may be used to provide different disintegration rates of biodisintegrable material in different regions of the medical device. In some embodiments, an endoprosthesis can include an arrangement of polyelectrolyte layers that causes one or both of the ends of the endoprosthesis to start disintegrating before the middle of the endoprosthesis. This may limit the likelihood of the medical device breaking apart into two or more pieces during disintegration. Further examples of such devices are found in pending U.S. patent application Ser. No. 11/127,968.

Many embodiments of a medical device having different numbers of layers on one portion from another portion are possible. By "portion" is meant some non-vanishing part that is less than the whole. Thus, in some embodiments, one portion of a medical device includes a multi-layered structure with at least 10 layers (e.g., at least 20 layers, at least 30 layers, or at least 40 layers), and another portion of a medical device includes a multi-layered structure with at least 20 layers (e.g., at least 30 layers, at least 40 layers, or at least 50 layers). For example, one portion of a medical device may include a multi-layered structure with 10 layers and another portion of the medical device may include a multi-layered structure with 40 layers. In certain embodiments, a multi-layered structure on one portion of a medical device can include from five to 50 layers (e.g., from 10 to 30 layers) more than a multi-layered structure on another portion of the medical device.

In some embodiments, one or more portions of a medical device may not be coated with any layers at all.

In some embodiments, devices having portions with different numbers of layers on them can be formed by dipping one end (e.g., ⅔) of a device in one material, turning the device around, and dipping the other end (e.g., ⅔) of the device in another material, and repeating the process multiple times. The result is that the middle of the device (e.g., the middle ⅓ of it) receives more layers than either end of the device. In certain embodiments, devices having portions with different numbers of layers on them can be formed by other techniques, such as ink jet techniques, microstamping, spraying, roll coating, or brush coating.

The underlying structure or fiber meshwork can be pretreated prior to forming a multi-layer structure on it. For example, an underlying structure can be cleaned to remove surface contaminants, such as oil, that can affect the homogeneity of the multi-layered structure. The underlying structure or fiber meshwork can be cleaned, for example, in a solvent such as acetone, or in a mixture such as $H_2O_2/HCl$, $HCl/HNO_3$, $H_2SO_4/K_2Cr_2O_7$, $H_2O_2/NH_3$, and/or $NaOH/NaOCl$. The structure can also be pretreated with a solution including $10^{-2}$ M SDS/0.12 N HCl for 15 minutes at 100° C.

An embodiment of a method of making a device using a layer-by-layer technique includes pretreating an underlying structure for layer-by-layer deposition. Next, a charged layer, e.g., containing a polyelectrolyte, is applied to the underlying structure. A layer of opposite charge is then applied to the previously applied charged layer. The previous two steps can then be repeated to build a multi-layered structure of a desired thickness. In some embodiments, as described herein, multi-layered structure can further include one or more layers that contain a therapeutic agent, one or more layers that contain a radio-opaque material, and/or one or more layers capable of enhancing the mechanical properties of the underlying structure. These additional layers can be applied between layers of different charges in any combination.

In another example, the material can be provided with a positive charge by covalently attaching functional groups having a positive charge (e.g., amine, imine or other basic groups) or functional groups having a negative charge (e.g., carboxylic, phosphonic, phosphoric, sulfuric, sulfonic, or other acid groups) to it.

In yet another example, a surface charge can be provided by exposing the device to a charged amphiphilic substance. In certain embodiments, the amphiphilic substance includes at least one electrically charged group to provide the device surface with a net electrical charge. Therefore, the amphiphilic substances that are used herein can also be referred to as ionic amphiphilic substances.

Thus, a surface charge can be provided on a material by adsorbing cations (e.g., protamine sulfate, polyallylamine, polydiallyldimethylammonium species, polyethyleneimine, chitosan, gelatin, spermidine, and/or albumin) or by adsorbing anions (e.g., polyacrylic acid, sodium alginate, polystyrene sulfonate, eudragit, gelatin (an amphiphilic polymer that fits in both categories depending how it is being prepared), hyaluronic acid, carrageenan, chondroitin sulfate, and/or carboxymethylcellulose) to the surface of the material as a first charged layer or to impart a surface charge. As an example, poly(ethylene imine) (PEI, Aldrich, MW ~25 kD) can be dissolved in water in a concentration of about 0.5 g/L to apply a first coating. In some embodiments, more than one surface charge layer can be applied to provide complete coverage of the material. Application of surface charge layers is described in, e.g., "Multilayer on Solid Planar Substrates", *Multi-layer Thin Films, Sequential Assembly of Nanocomposite Materials*, Wiley-VCH ISBN 3-527-30440-1, Chapter 14; and "Surface-chemistry Technology for Microfluidics" Hau, Winky L. W. et al., *J. Micromech. Microeng.*, 13, 272-278, (2003).

The species for establishing a surface charge can be applied to the material by a variety of methods. Examples of such methods include spraying methods, dipping methods, roll and brush coating methods, methods involving coating via mechanical suspension such as air suspension, ink jet methods, spin coating methods, web coating methods and combinations of these processes. Dipping and spraying methods (without masking) can be employed, for example, to apply the species to an entire device. Roll coating, brush coating and ink jet printing can be employed, for example, to apply the species only to selected portions of the device (e.g., in the form of a pattern).

In an embodiment, the polymer from which the fiber meshwork is made is charged. Thus, an oppositely-charged layer can be easily deposited thereon.

Delivery of Therapeutic Agents

In embodiments, the multi-layered structure includes one or more layers that contain a therapeutic agent. As an example, one or more therapeutic agents can be disposed on or within the multi-layered structure giving the medical device a drug releasing function upon implantation. Therapeutic agents may be used singly or in combination.

Examples of therapeutic agents can be found at cols. 4-6 of U.S. Pat. No. 6,899,731 to Li et al., and at cols. 5-8 of U.S. Pat. No. 6,923,996 to Epstein et al., the disclosures of which are incorporated by reference in their entirety. It is to be understood that the therapeutic agents that can be used are not limited to those found herein.

Examples of therapeutic agents and methods of incorporating such agents into a multi-layer structure are described in U.S. patent application Ser. No. 10/849,742, filed May 20, 2004. U.S. Pat. No. 5,733,925, to Kunz et al., also provides general guidance for incorporating therapeutic agents into layers.

The fiber meshwork or a multi-layer structure may instead or additionally be used to deliver an antimicrobial agent, such as for the purpose of preventing or limiting local infection in the vicinity of the device. Exemplary antimicrobial agents have broad-spectrum activity and include triclosan, chlorhexidine, silver sulfadiazine, silver ions, benzalkonium chloride, and zinc pyrithione, as well as broad-spectrum antibiotics such as quinolones, fluoroquinolones, aminoglycosides and sulfonamides. Antiseptics such as iodine, methenamine, nitrofurantoin, validixic acid and other acidifying agents, including acids extracted from cranberry juice may also be used.

The therapeutic agent can be charged, either because it is itself a charged molecule or because it becomes charged upon, for example, a change in ambient pH or upon association with a charged species. Examples of charged therapeutic agents include small molecule and polymeric therapeutic agents containing ionically dissociable groups. In some embodiments in which the therapeutic agent does not possess one or more charged groups, it can nevertheless be provided with a charge, for example, through non-covalent association with a charged species. Examples of non-covalent associations include hydrogen bonding, electrostatic, van der Waals, and hydrophobic/lipophilic interactions. For instance, a therapeutic agent can be associated with an ionic amphiphilic substance.

In certain embodiments in which a charged therapeutic agent is used, one or more layers consisting of the charged therapeutic agent are deposited during the course of assembling the multi-layer structure. Thus, in some embodiments an entire layer may be composed of a therapeutic agent. For example, the therapeutic agent can itself be a polyelectrolyte (e.g., where the therapeutic agent is a polypeptide or a polynucleotide) and is thereby used to create one or more polyelectrolyte layers within the multi-layer structure. In other embodiments, the charged therapeutic agent is not a polyelectrolyte (e.g., it may be a charged small molecule drug), but one or more layers of the charged therapeutic agent can be substituted for one or more layers of the same charge (i.e., positive or negative) during the layer-by-layer assembly process.

A wide range of therapeutic agent loadings can be used. The amount of such loading can be readily determined by those of ordinary skill in the art, and will ultimately depend upon the condition to be treated, the nature of the therapeutic agent itself, the avenue by which the therapeutic-agent-loaded layer-by-layer structure or fiber meshwork is administered to the intended subject, and so forth. The loaded fiber meshwork, or multi-layered structure, may comprise, for example, from about 1 wt. % to about 70 wt. % therapeutic agent.

The amount of the therapeutic agent may be limited by the propensity of such agent to cause an undesirable localized or systemic toxic reaction and by the impairment of mechanical properties necessary for proper functioning of the device.

In still other embodiments, the therapeutic agent can be provided within charged nanocapsules, which are formed, for example, using methods such as those described in U.S.

Patent Application Publication No. 2005-0129727, entitled "Localized Drug Delivery Using Drug-Loaded Nanocapsules". In such embodiments, one or more layers of charged nanocapsules can be deposited during the course of the layer-by-layer assembly process.

In still other embodiments, the multi-layer structure is loaded with a therapeutic agent subsequent to its formation. For example, the porosity, and thus the permeability, of the multi-layer structure can be modified by adjusting the pH exposed to the structure, as described, for example, in Antipov, A. A., et al., "Polyelectrolyte multilayer capsule permeability control," *Colloids and Surfaces A: Physicochemical and Engineering Aspects*, 198-200, 535-541, (2002). A porous layer can absorb a therapeutic agent after the layer is in place.

Device Materials

The underlying structure of the medical device of the present invention is, in some embodiments, formed of a biocompatible material, such as the materials described herein. Specific examples of biocompatible materials from which the underlying structure can be formed are described in U.S. patent application Ser. No. 10/440,063, filed May 15, 2003; and U.S. Patent Application Publication Nos. 2003-0018380, 2002-0144757, and 2003-0077200. Still further examples of biocompatible materials are described, for example, in Weber et al., U.S. Patent Application Publication No. 2004/0230290 A1, published on Nov. 18, 2004; Craig et al., U.S. Patent Application Publication No. 2003/0018380 A1, published on Jan. 23, 2003; Craig et al., U.S. Patent Application Publication No. US 2002/0144757 A1, published on Oct. 10, 2002; and Craig et al., U.S. Patent Application Publication No. 2003/0077200 A1, published on Apr. 24, 2003.

The biocompatible material can be suitable for use in, for example, a balloon-expandable stent, a self-expandable stent, or a combination of both (see e.g., U.S. Pat. No. 5,366,504). A self-expandable stent can be formed of a continuous solid mass of a relatively elastic biocompatible material, such as a superelastic or pseudo-elastic metal alloy, for example, a Nitinol (e.g., 55% nickel, 45% titanium). A self-expanding stent has a mechanical memory such that it can return to a preformed shape after it has been compressed or deformed. The stent is initially configured in its final desired shape and is then contracted by deforming or constraining it using any of several methods known in the art. It remains in a contracted state until it is delivered to the target site where it is allowed to expand to its initial state. Examples of materials that can be used for a balloon-expandable stent include noble metals, radiopaque materials, stainless steel, and alloys comprising stainless steel and one or more radiopaque materials.

The underlying structure can be formed of a biodisintegrable material, such as a biodisintegrable metal, a biodisintegrable metal alloy, or a biodisintegrable non-metal. Biodisintegrable materials are described, for example, in U.S. Pat. No. 6,287,332 to Bolz; U.S. Patent Application Publication No. US 2002/0004060 A1 to Heublein; U.S. Pat. Nos. 5,587,507 and 6,475,477 to Kohn et al. Examples of biodisintegrable metals for use with the underlying structure include alkali metals, alkaline earth metals (e.g., magnesium), iron, zinc, and aluminum. Examples of biodisintegrable metal alloys include alkali metal alloys, alkaline earth metal alloys (e.g., magnesium alloys), iron alloys (e.g., alloys including iron and up to seven percent carbon), zinc alloys, and aluminum alloys.

In some embodiments, a biodisintegrable material from which the underlying structure is formed, can include at least one metallic component and at least one non-metallic component, or at least two different metallic components. In some embodiments, a biodisintegrable material can include at least one of the following: manganese, cobalt, nickel, chromium, copper, cadmium, lead, tin, thorium, zirconium, silver, gold, palladium, platinum, rhenium, silicon, calcium, lithium, aluminum, zinc, iron, carbon, and sulfur. In certain embodiments, a biodisintegrable material can include at least two of the following metals in proportions by weight of greater than about 1%: magnesium, titanium, zirconium, niobium, tantalum, zinc, or silicon, and lithium, sodium, potassium, calcium, iron, or manganese. In certain embodiments, the biodisintegrable material can include a first component selected from the group consisting of: magnesium, titanium, zirconium, niobium, tantalum, zinc, silicon, and another, different, component selected from the group consisting of: lithium, sodium, potassium, calcium, iron, manganese.

Examples of biodisintegrable non-metals include biodisintegrable polymers, such as polyiminocarbonates, polycarbonates, polyarylates, polylactides, or polyglycolic esters. In some embodiments, a biodisintegrable metal or metal alloy containing metals such as magnesium, iron, or zinc, can be sintered. In some embodiments, the biodisintegrable material can be a polymer, such as, without limitation, those described at cols. 8-9 of U.S. Pat. No. 6,918,869 to Shaw et al.

In still other embodiments, the biodisintegrable material can be a ceramic such as an alumina-based ceramic, or a glass-based ceramic such as Macor®.

The properties of the underlying structure depend upon the material from which it is formed. Magnesium, for example, has a relatively low mass attenuation factor, and the CT visibility of the region (e.g., a body lumen) in which a magnesium structure is located can be relatively high.

The underlying structure of a medical device for use as described herein can be manufactured, or can be obtained commercially. Methods of making medical devices such as stents are described in, for example, U.S. Pat. No. 5,780,807, and U.S. Patent Application Publication No. 2004-0000046-A1, both of which are incorporated herein by reference. Stents are also available, for example, from Boston Scientific Corporation, Natick, Mass., USA, and Maple Grove, Minn., USA.

Metallic materials from which the underlying structure is made may be made into filaments and then woven so that the underlying structure forms a regular network of metal mesh. Polymer filaments may also be used together with the metallic filaments to form a network. If the network is made of metal, the intersection between different filaments may formed by welding, twisting, bending, gluing, tying (with suture), heat sealing, or by any other manner known in the art.

As another example, although a stent may include a tubular structure that is formed entirely of a biodisintegrable material, in some embodiments, the tubular structure of a stent can include one or more biostable materials in addition to including one or more biodisintegrable materials. One or more polymers may be used (as described herein) to control the disintegration of one or more of the biodisintegrable regions of the stent. The polymers may be in the form of layers over the biodisintegrable and/or biostable regions of the stent or a fiber meshwork similarly disposed. Examples of biostable materials include stainless steel, tantalum, nickel-chrome, cobalt-chromium alloys such as Elgiloy® and Phynox®, Nitinol (e.g., 55% nickel, 45% titanium), and other alloys based on titanium, including nickel titanium alloys, thermo-memory alloy materials. Stents including biostable and biodisintegrable regions are described, for example, in U.S. patent application Ser. No. 11/004,009, filed on Dec. 3, 2004, and entitled "Medical Devices and Methods of Making the Same".

Devices, such as stents, may be formed from many known constructions such as cross-hatched or mesh filaments or interlocking loops.

Stents/Devices

The embodiments described herein may be used in conjunction with various medical devices, in particular endoprostheses. Exemplary medical devices are implantable or insertable medical devices, including catheters (for example, urinary catheters or vascular catheters such as balloon catheters), guide wires, balloons, filters (e.g., vena cava filters), stents of any desired shape and size (including coronary vascular stents, aortic stents, cerebral stents, urology stents such as urethral stents and ureteral stents, biliary stents, tracheal stents, gastrointestinal stents, peripheral vascular stents, neurology stents and esophageal stents), grafts such as stent grafts and vascular grafts, cerebral aneurysm filler coils (including GDC-Guglilmi detachable coils-and metal coils), filters, myocardial plugs, patches, pacemakers and pacemaker leads, heart valves, and biopsy devices. Indeed, embodiments herein can be suitably used with any underlying structure (which can be, for example, metallic, polymeric or ceramic, though typically metallic) which is coated with a fiber meshwork in accordance with methods herein and which is designed for use in a patient, either for procedural use or as an implant.

The medical devices may further include drug delivery medical devices for systemic treatment, or for treatment of any mammalian tissue or organ. Subjects can be mammalian subjects, such as human subjects. Non-limiting examples of tissues and organs for treatment include the heart, coronary or peripheral vascular system, lungs, trachea, esophagus, brain, liver, kidney, bladder, urethra and ureters, eye, intestines, stomach, colon, pancreas, ovary, prostate, gastrointestinal tract, biliary tract, urinary tract, skeletal muscle, smooth muscle, breast, cartilage, and bone.

In some embodiments, the medical device is used to temporarily treat a subject without permanently remaining in the body of the subject. For example, in some embodiments, the medical device can be used for a certain period of time (e.g., to support a lumen of a subject), and then can disintegrate after that period of time.

The underlying structure of the medical device can be generally tubular in shape and can be a part of a stent. Simple tubular structures having a single tube, or with complex structures, such as branched tubular structures, can be used.

Depending on specific application, stents can have a diameter of between, for example, 1 mm and 46 mm. In certain embodiments, a coronary stent can have an expanded diameter of from about 2 mm to about 6 mm. In some embodiments, a peripheral stent can have an expanded diameter of from about 4 mm to about 24 mm. In certain embodiments, a gastrointestinal and/or urology stent can have an expanded diameter of from about 6 mm to about 30 mm. In some embodiments, a neurology stent can have an expanded diameter of from about 1 mm to about 12 mm. An abdominal aortic aneurysm (AAA) stent and a thoracic aortic aneurysm (TAA) stent can have a diameter from about 20 mm to about 46 mm.

Stents can also be a part of a stent-graft or a covered stent. In other embodiments, stents can include and/or be attached to a biocompatible, non-porous or semi-porous polymer matrix made of polytetrafluoroethylene (PTFE), expanded PTFE, polyethylene, urethane, or polypropylene.

Stents can also be biodisintegrable, such as a biodisintegrable abdominal aortic aneurysm (AAA) stent, or a biodisintegrable vessel graft.

EXAMPLES

Example 1

Collagen-based Fiber Meshwork on a Stent

Collagen type I (Sigma-Aldrich (St. Louis, Mo.)) dissolves in 1,1,1,2,2,2-hexafluoro-2-propanol (HFIP). A solution was prepared making a 8% by weight solution of Collagen in HFIP. A stent (BSC, stainless steel, express stent, 16 mm length, 3.0 mm diameter), was crimped on a Teflon mandrel having diameter 3.0 mm, with a fine 10 micron gold wire (California Fine Wire, 338 So. Fourth Street, Grover Beach, Calif. 93433-0199) placed in between the stent and the mandrel such that there was electrical contact between the stent and the gold wire. The gold wire was grounded.

A nozzle with Syringe was placed at a distance of 7 cm from the stent surface and connected to a syringe pump (type SP101i, World Precision Instruments, Liegnitzer Str.15, D-10999 Berlin, Germany), and a high voltage supply (Type CS2091, High Voltage Power Solutions, Inc. (HVPSI), Dallas, Tex. 75370). The mandrel was rotated at 5 Hz during the spraying process and moved along the axis in a cyclic movement at 12 Hz with an amplitude of 2 mm. The spraying was done at the following settings (18 kV, 0.02 ml/min, 10 seconds on cycle). This resulted in a 90% porous fibrin structure being 10 micrometer thick covering the stent. The collagen nanofiber network spun in this way was crosslinked by glutaraldehyde vapor at room temperature for 12 hours (Sigma-Aldrich (St. Louis, Mo.)).

Example 2

Polyetherimide-based Fiber Meshwork on a Stent

Polyetherimide (PEI) was purchased from Aldrich Co. (St. Louis, Mo.)), and Biopol™, polyhydroxybutyrate-valerate (PHBV) was purchased from Monsanto Company (800 North Lindbergh, St. Louis, Mo. 63167). Both components were mixed in chloroform making solutions having 23 wt. % PEI and 21 wt. % PHBV. These solutions were mixed to a ratio of $^{75}/_{25}$ (PEI/PHBV)

A stent (Boston SciMed Corporation, stainless steel, express stent, 16 mm length, 3.0 mm diameter), was crimped on a Teflon mandrel diameter 3.0 mm with a fine 10 micron gold wire (California Fine Wire, 338 So. Fourth Street, Grover Beach, Calif. 93433-0199) placed in between the stent and the mandrel, such that there was electrical contact between the stent and the gold wire. The gold wire was grounded.

A nozzle with syringe was placed at a distance of 15 cm from the stent surface and connected to a syringe pump (type SP101i, World Precision Instruments, Liegnitzer Str.15, D-10999 Berlin, Germany), and a high voltage supply (Type CS2091, High Voltage Power Solutions, Inc. (HVPSI), High Voltage Power Solutions, Inc., Dallas, Tex. 75370). The mandrel was rotated at 5 Hz during the spraying process and moved along the axis in a cyclic movement at 12 Hz with an amplitude of 2 mm. The spraying was carried out at the following settings: 15 kV, 0.05 ml/min, 15 seconds on cycle. The stent sprayed in this way was thermally treated for 90 minutes at 210° C. in a nitrogen environment to decompose the PHBV component and leave behind a fiber meshwork made of porous PEI fibers.

The fibers created in this way were coated with a layer of Heparin via a polyelectrolyte self-assembly process. Heparin in sodium salt form, from Bioiberica (Barcelona, Spain) is negatively charged and binds readily to the positively charged PEI surface when the stent with fiber meshwork is dipped for 10 minutes in an aqueous (2 mg/ml) heparin solution followed drying with a stream of nitrogen.

The PEI fiber meshwork created in this way can also be used to deliver drug-filled liposome capsules (e.g., as described in Vermette et al., "Immobilized liposome layers for drug delivery applications: inhibition of angiogenesis", *J. Controlled Release*, 80:179-195 (2002), incorporated herein by reference in its entirety) or other polyelectrolyte capsules filled with various drugs. Leaving the stent with the electro-spun network on the Teflon mandrel while attaching the capsules will assure that they only attach to the outside and that, in use, they are therefore all trapped in between the stent and the wall of the vessel or body lumen.

Example 3

Collagen-based Fiber Meshwork Modified with Polyelectrolyte Layers

In another embodiment, instead of using PEI fibers as in Example 2, the collagen fibers as discussed in Example 1 can also be coated with additional polyelectrolyte layers, but using only non-polymeric biological material such as collagen and alternating hyaluronic acid or heparin elements (see e.g., Zhang, et al., "Natural polyelectrolyte films based on layer-by-layer deposition of collagen and hyaluronic acid", *Biomaterials*, 26:3353-3361, (2005)). To those layers again, capsules are bound using polyelectrolyte constructions.

All non-patent literature publications, patent applications, patent application publications, and patents, referred to in the instant application are incorporated herein by reference in their entirety.

Other embodiments are to be found within the appended claims.

What is claimed is:

1. A medical device for implantation into an organism, comprising:
   an underlying structure comprising a metal framework, wherein the underlying structure is biodisintegrable; and
   a fiber meshwork disposed upon the underlying structure, wherein the fiber meshwork comprises nano-fibers or micro-fibers, wherein the fiber meshwork is configured to ensure steady biodisintegration of the underlying structure over a first period of time inside the organism, wherein the fiber meshwork additionally effects controlled release of a pharmaceutically active agent absorbed therein over a second period of time inside the organism, wherein the first period of time is less than the second period of time.

2. The medical device of claim 1 wherein the framework is made of a metal selected from the group consisting of: alkali metals, alkaline earth metals, iron, zinc, and aluminum.

3. The medical device of claim 2 wherein the metal is magnesium.

4. A The medical device of claim 1,
   wherein the metal is iron.

5. The medical device of claim 1, wherein the framework comprises a metal alloy.

6. The medical device of claim 5, wherein the framework comprises a magnesium alloy.

7. A The medical device of claim 1, comprising:
   wherein the framework comprises an iron alloy.

8. The medical device of claim 1, wherein the framework comprises a first metal selected from the group consisting of: magnesium, titanium, zirconium, niobium, tantalum, zinc, and silicon, and a second metal selected from the group consisting of lithium, sodium, potassium, calcium, iron, and manganese.

9. The medical device of claim 1 wherein the fiber meshwork comprises a polymeric material.

10. The medical device of claim 1 wherein the fiber meshwork comprises two or more non-contiguous fibers.

11. The medical device of claim 1 wherein the fiber meshwork comprises an electro-spun polymeric material.

12. The medical device of claim 11 wherein the fiber meshwork is electro-spun by FFESS.

13. The medical device of claim 1 wherein the fiber meshwork comprises one or more fibers, wherein each of said one or more fibers has a diameter in the range 50 nm-500 nm.

14. The medical device of claim 13 wherein the fiber meshwork comprises at least two fibers, including a first fiber of a first type of material, and a second fiber of a second type of material.

15. The medical device of claim 14 wherein the first type of material has a first pharmaceutically active ingredient absorbed within it, and the second type of material has a second pharmaceutically active ingredient absorbed within it.

16. The medical device of claim 1 wherein the fiber meshwork comprises one or more fibers, wherein each of said one or more fibers has a diameter <1 μm.

17. The medical device of claim 16 wherein each of said one or more fibers has a uniform diameter along its length.

18. The medical device of claim 1, wherein the fiber meshwork comprises a composition selected from the group consisting of: poly(D,L-lactide-co-glycolide);
   magnesium; iron, or zinc.

19. The medical device of claim 1 further comprising a layer-by-layer coating situated on the fiber meshwork.

20. The medical device of claim 19, wherein the layer-by-layer coating comprises a first layer of a first polyelectrolyte, and a second layer of a second polyelectrolyte.

21. The medical device of claim 20, wherein the first polyelectrolyte is positively charged and the second polyelectrolyte is negatively charged, or vice versa.

22. The medical device of claim 19, wherein the layer-by-layer coating comprises at least 10 layers.

23. The medical device of claim 19, wherein the layer-by-layer coating comprises at most 300 layers.

24. The medical device of claim 19, wherein the layer-by-layer coating further comprises a therapeutic agent.

25. The medical device of claim 19, wherein the layer-by-layer coating further comprises nanoparticles.

26. The medical device of claim 1, wherein the underlying structure is generally tubular in shape.

27. The medical device of claim 26 wherein the first ring is made of a first material and wherein the second ring is made of a second material, and wherein the first material and the second material are different from a material of which the fiber meshwork is comprised.

28. The medical device of claim 1, wherein the underlying structure comprises a first ring and a second ring, wherein the first ring and the second ring are connected to one another by the fiber meshwork.

29. The medical device of claim 28 wherein the first material and the second material are each independently selected from the group consisting of: nitinol, magnesium, and steel.

30. The medical device of claim 1 wherein the first period of time is between about 60 days and about 1,000 days.

31. The medical device of claim 1 wherein the first period of time is between about 120 days and about 750 days.

32. The medical device of claim 1 wherein the first period of time is between about 180 days and about 600 days.

33. The medical device of claim 1 wherein the biodisintegration comprises a mass reduction of at least about 50% of the structure.

34. The medical device of claim 1 wherein the second period of time is between about 60 days and about 1,000 days.

35. The medical device of claim 1 wherein the second period of time is between about 120 days and about 750 days.

36. The medical device of claim 1 wherein the second period of time is between about 180 days and about 600 days.

37. The medical device according to claim 1, further comprising a multi-layer structure disposed upon the fiber meshwork.

38. The medical device according to claim 37 wherein the multi-layer structure comprises alternating layers formed of molecules having opposite charges to one another.

39. The medical device of claim 1, wherein the device is an endoprosthesis.

* * * * *

UNITED STATES PATENT AND TRADEMARK OFFICE
CERTIFICATE OF CORRECTION

| | | |
|---|---|---|
| PATENT NO. | : 8,048,150 B2 | Page 1 of 1 |
| APPLICATION NO. | : 11/403344 | |
| DATED | : November 1, 2011 | |
| INVENTOR(S) | : Jan Weber, James Q. Feng and Liliana Atanasoska | |

It is certified that error appears in the above-identified patent and that said Letters Patent is hereby corrected as shown below:

1.) Column 29, Claim 4, Line 58: delete "A The" and insert --The--.

2.) Column 29, Claim 7, Line 64: delete "A The" and insert --The--.

3.) Column 29, Claim 7, Line 64: delete "claim 1, comprising:" and insert --claim 1--.

4.) Column 30, Claim 26, Line 50: delete "claim 1," and insert --claim 1--.

5.) Column 30, Claim 28, Line 57: delete "claim 1," and insert --claim 1--.

Signed and Sealed this
Third Day of January, 2012

David J. Kappos
*Director of the United States Patent and Trademark Office*